US006670358B2

(12) United States Patent
Bacon et al.

(10) Patent No.: US 6,670,358 B2
(45) Date of Patent: Dec. 30, 2003

(54) SUBSTITUTED THIOACETAMIDES

(75) Inventors: Edward R. Bacon, Audubon, PA (US); Sankar Chatterjee, Wynnewood, PA (US); Derek Dunn, Coatesville, PA (US); John P. Mallamo, Glenmoore, PA (US); Matthew S. Miller, Newtown, PA (US); Rabindranath Tripathy, Landenberg, PA (US); Jeffry L. Vaught, Glenmoore, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 10/014,645

(22) Filed: Oct. 26, 2001

(65) Prior Publication Data

US 2002/0183334 A1 Dec. 5, 2002

Related U.S. Application Data

(63) Continuation-in-part of application No. 09/855,228, filed on May 15, 2001, now Pat. No. 6,492,396.
(60) Provisional application No. 60/204,789, filed on May 16, 2000, and provisional application No. 60/268,283, filed on Feb. 13, 2001.

(51) Int. Cl.⁷ .................. C07D 213/02; A61K 31/44
(52) U.S. Cl. .............. 514/231.2; 514/357; 514/365; 514/374; 514/423; 514/440; 514/454; 514/617; 544/106; 546/336; 548/202; 548/235; 548/570; 549/31; 549/385; 564/161

(58) Field of Search .............. 564/161; 514/617, 514/231.2, 357, 365, 374, 423, 440, 454; 544/106; 546/336; 548/202, 235, 570; 549/31, 385

(56) References Cited

U.S. PATENT DOCUMENTS 4,489,095 A   12/1984   Lafon ................. 424/315

FOREIGN PATENT DOCUMENTS

WO   WO 93/06096   *   4/1993   ..... C07D/311/82
WO   WO 01/87930       11/2001

OTHER PUBLICATIONS

Dostert et al, Chemical Abstracts, vol. 82, No. 1, Abstract 16608h, p. 477, Jan. 6, 1975.*
Saenz et al, Journal of Pharmaceutical Sciences, vol. 61, No. 6, pp. 978–980, Jun. 1972.*
Portevin, B. et al., *J. Med. Chem.*, 1996, 39, 2379–2391.

* cited by examiner

*Primary Examiner*—Zinna Northington Davis
(74) *Attorney, Agent, or Firm*—Robert T. Hrubiec; Eric K. Voelk

(57) ABSTRACT

The present invention is directed to chemical compositions of substituted thioacetamides, processes for the preparation thereof and uses of the compositions in the treatment of diseases.

29 Claims, 2 Drawing Sheets

SUBSTITUTED THIOACETAMIDES

REFERENCE TO RELATED APPLICATIONS

The present application is a continuation-in-part of application Ser. No. 09/855,228, filed May 15, 2001, now U.S. Pat. No. 6,492,396, which claims priority to U.S. Provisional application Serial No. 60/204,789, filed May 16, 2000 and U.S. provisional application Serial No. 60/268,283, filed Feb. 13, 2001. The disclosure of each of these applications is hereby incorporated herein by reference in their entireties.

FIELD OF THE INVENTION

The present invention is related to chemical compositions, processes for the preparation thereof and uses of the composition. Particularly, the present invention relates to compositions that include substituted thioacetamides, and their use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl) acetamide, or 2-[(diphenylmethyl) sulfinyl] acetamide, is a synthetic acetamide derivative with wake-promoting activity, the structure of which has been described in French Patent No. 78 05 510 and in U.S. Pat. No. 4,177,290 ('290), and which has been approved by the United States Food and Drug Administration for use in the treatment of excessive daytime sleepiness associated with narcolepsy. Modafinil has been tested for treatment of several behavioral conditions in combination with various agents including apomorphine, amphetamine, reserpine, oxotremorine, hypnotics, yohimbine, 5-hydroxytryptophan, and monoamine oxidase inhibitors, as described in the cited patents. A method of preparation of a racemic mixture is described in the '290 patent and a method of preparation of a levorotatory isomer is described in U.S. Pat. No. 4,927,855 (both incorporated herein by reference). The levorotatory isomer is reported to be useful for treatment of hypersomnia, depression, Alzheimer's disease and to have activity towards the symptoms of dementia and loss of memory, especially in the elderly.

The primary pharmacological activity of modafinil is to promote wakefulness. Modafinil promotes wakefulness in rats (Touret et al., 1995; Edgar and Seidel, 1997), cats (Lin et al., 1992), canines (Shelton et al., 1995) and non-human primates (Hernant et al, 1991) as well as in models mimicking clinical situations, such as sleep apnea (English bulldog sleep disordered breathing model) (Panckeri et al, 1996) and narcolepsy (narcoleptic canine) (Shelton et al, 1995).

Modafinil has also been described as an agent with activity in the central nervous system, and as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). U.S. Pat. No. 5,618,845 describes modafinil preparations of a defined particle size less than about 200 microns. In addition, modafinil may be used in the treatment of eating disorders, or to promote weight gain or stimulate appetite in humans or animals (U.S. Provisional Patent Application No. 60/150,071, incorporated herein by reference), or in the treatment of attention deficit hyperactivity disorder (ADHD), or fatigue, especially fatigue associated with multiple sclerosis (U.S. Provisional Patent Application No. 60/149,612, incorporated herein by reference).

Several published patent applications describe derivative forms of modafinil and the use of modafinil derivatives in the treatment of various disorders. For example, PCT publication WO 99/25329 describes analogs of modafinil in which the phenyl groups are substituted with a F, Cl, Br, $CF_3$, $NO_2$, $NH_2$, $C_1$–$C_4$ alkyl, $C_1$–$C_4$ alkoxy, or methylenedioxy, and in which the amide is substituted with OH, $C_1$–$C_4$ alkyl, $C_1$–$C_4$ hydroxyalkyl, or a $C_1$–$C_4$ hydrocarbon radical. These compositions are described as being useful for treating drug-induced sleepiness, especially sleepiness associated with administration of morphine to cancer patients.

Similarly, U.S. Pat. No. 4,066,686 describes benzhydrylsulphinyl derivatives, including modafinil derivatives with an extended alkyl chain between the sulfinyl and carbonyl groups and where $NR_3R_4$ is NHOH. These compounds are described as being useful in therapy for treating disturbances of the central nervous system.

PCT publication WO 95/01333 describes modafinil derivatives that are useful for modifying feeding behavior. The modifications to modafinil described include a chloro group at the 3 position of one of the phenyl groups, and a pyridyl substituted for the second phenyl, substitution of one or two methyl groups for hydrogens at the 2-carbon position, the amide hydrogens may be substituted with one or two groups selected from H, a pyridyl-methyl or ethyl groups, and further where the sulfur may not be oxidized.

PCT publication WO 95/01171 also describes modified modafinil compounds that are said to be useful for modifying eating behavior. The described compounds include substitutions of 4-fluoro-, 3-fluoro-, and 4 chloro- in a first phenyl group and 4-fluoro- or 3-fluoro-substitutions in the second phenyl. Also described are substitutions in which the amide contains substitutions with an OH or isopropyl group.

Terauchi, H, et al. described nicotinamide derivatives useful as ATP-ase inhibitors (Terauchi, H, et al, *J. Med. Chem.*, 1997, 40, 313–321). In particular, several N-alkyl substituted 2-(Benzhydrylsulfinyl) nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* 15th (Meeting Date 1997) 343–344, 1999 (preparation of a xanthenyl derivative of Ellman's Reagent, useful as a reagent in peptide synthesis); Han, Y.; Barany, G. *J. Org. Chem.*, 1997, 62, 3841–3848 (preparation of S-xanthenyl protected cysteine derivatives, useful as a reagent in peptide synthesis); and El-Sakka, I. A., et al. *Arch. Pharm. (Weinheim)*, 1994, 327, 133–135 (thiaxanthenol derivatives of thioglycolic acid).

Thus, there is a need for novel classes of compounds that possess beneficial properties. It has been discovered that a class of compounds, referred to herein as substituted thioacetamides, are useful as agents for treating or preventing diseases or disorders, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder, enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction. The present invention is directed to these, as well as other, important ends.

SUMMARY OF THE INVENTION

One aspect of the present invention provides, in part, various novel substituted thioacetamides. Other aspects of the invention also include their pharmaceutical compositions, methods of their preparation, and use of the compounds in the treatment of diseases.

In one aspect of the invention, there are provided compounds of formula (I-A):

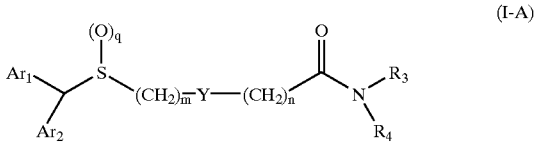

(I-A)

Constituent members and preferred embodiments are disclosed in detail infra.

In another aspect of the invention, there are provided compounds of formula (I):

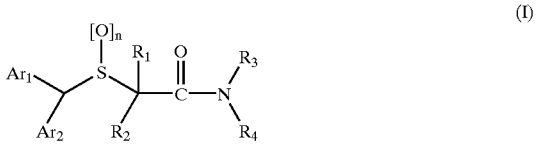

(I)

Constituent members and preferred embodiments are disclosed in detail infra.

Another object of the present invention is to provide compounds of formula (II-A):

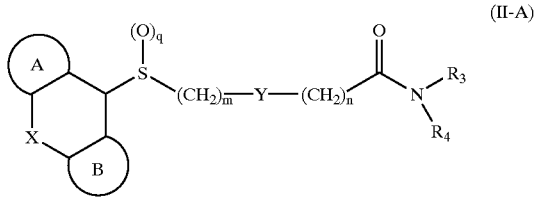

(II-A)

Constituent members and preferred embodiments are disclosed in detail infra.

An additional object of the present invention is to provide compounds of formula (II):

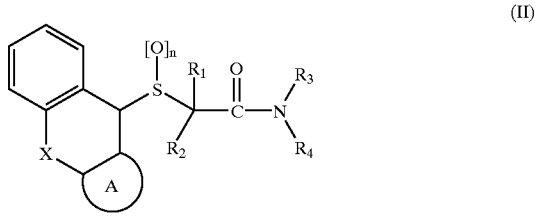

(II)

Constituent members and preferred embodiments are disclosed in detail infra.

Another object of the present invention is to provide methods of treating or preventing diseases or disorders, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder, enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

These and other objects, features and advantages of the substituted thioacetamides will be disclosed in the following detailed description of the patent disclosure.

DETAILED DESCRIPTION OF THE INVENTION

Figure 1:
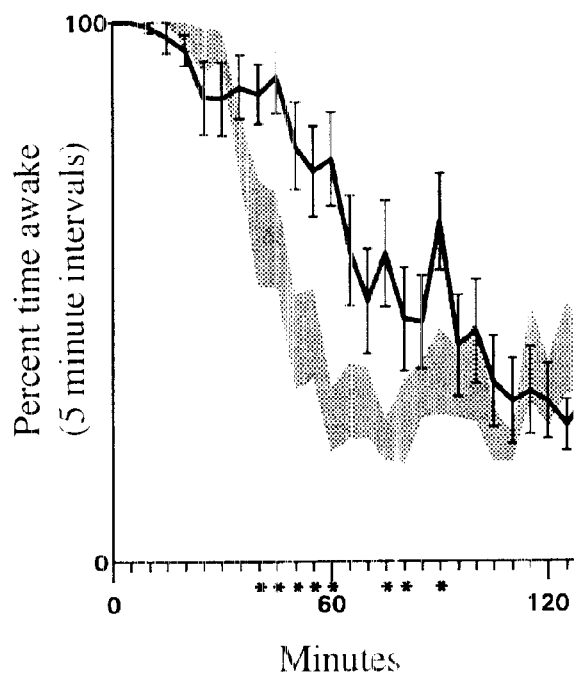
FIG. 1 is a graph of data indicating EEG-determined wakefulness in rats treated with Compound I-9 (100 mg/kg, ip; solid line) or methylcellulose vehicle (stippled line). Wakefulness is quantified in 5-minute bins. N=13 rats/group. *$p<0.05$ vs. vehicle treated animals.

In one embodiment, the present invention provides novel compounds of formula (I-A):

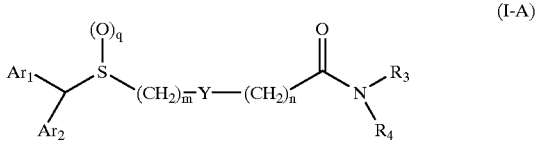

(I-A)

wherein:
$Ar_1$ and $Ar_2$ are each independently selected from $C_6$–$C_{10}$ aryl or heteroaryl;
wherein each of $Ar_1$ or $Ar_2$ may be independently optionally substituted with 1–3 substituents independently selected from:

a) H, $C_6$–$C_{10}$ aryl, heteroaryl, F, Cl, Br, I, —CN, —$CF_3$, —$NO_2$, —OH, —$OR_7$, —$O(CH_2)_pNR_9R_{10}$, —OC(=O)$R_7$, —OC(=O)$NR_9R_{10}$, —$O(CH_2)_pOR_8$, —$CH_2OR_8$, —$NR_9R_{10}$, —$NR_8S(=O)_2R_7$, —$NR_8C(=O)R_7$, or —$NR_8C(=S)R_7$;

b) —$CH_2OR_{11}$;

c) —$NR_8C(=O)NR_9R_{10}$, —$NR_8C(=S)NR_9R_{10}$, —$CO_2R_{12}$, —C(=O)$R_{13}$, —C(=O)$NR_9R_{10}$, —C(=S)$NR_9R_{10}$, —CH=$NOR_{12}$, —CH=$NR_7$, —$(CH_2)_pNR_9R_{10}$, —$(CH_2)_pNHR_{11}$, —CH=$NNR_{12}R_{12A}$, —C(=$NR_8$)$NR_{8A}R_{8B}$—$NR_8C(=NH)R_{8A}$, —$NR_8C(=NH)NR_{8A}R_{8B}$,

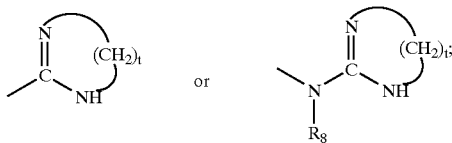

or d) —$S(O)_yR_7$, —$(CH_2)_pS(O)_yR_7$, —$CH_2S(O)_yR_7$; and e) $C_1$–$C_8$ alkyl, $C_2$–$C_8$ alkenyl, or $C_2$–$C_8$ alkynyl, where:
 1) each alkyl, alkenyl, or alkynyl group is unsubstituted; or
 2) each alkyl, alkenyl or alkynyl group is independently substituted with 1 to 3 groups independently selected from $C_6$–$C_{10}$ aryl, heteroaryl, F, Cl, Br, I, $CF_3$, —CN, —$NO_2$, —OH, —$OR_7$, —$CH_2OR_8$, —$NR_9R_{10}$, —O—$(CH_2)_p$—OH, —S—$(CH_2)_p$—OH, —$X_1(CH_2)_pOR_7$, $X_1(CH_2)_pNR_9R_{10}$, —$X_1(CH_2)_pC(=O)NR_9R_{10}$, —$X_1(CH_2)_pC(=S)NR_9R_{10}$, —$X_1(CH_2)_pOC(=O)NR_9R_{10}$, —$X_1(CH_2)_pCO_2R_8$, —$X_1(CH_2)_pS(O)_yR_7$, —$X_1(CH_2)_pNR_8C(=O)NR_9R_{10}$, —C(=O)$R_3$, —$CO_2R_{12}$, —OC(=O)$R_7$, —C(=O)$NR_9R_{10}$, —OC(=O)$NR_{12}R_{12A}$, O-tetrahydropyranyl, —C(=S)$NR_9R_{10}$, —CH=$NNR_{12}R_{12A}$, —CH=$NOR_{12}$, —CH=$NR_7$, —CH=NNHCH(N=NH)$NH_2$, —$NR_8CO_2R_7$, —$NR_8C(=O)NR_9R_{10}$, —$NR_8C(=S)NR_9R_{10}$, —NHC(=NH)$NH_2$, —$NR_8C(=O)R_7$, —$NR_8C(=S)R_7$, —$NR_8S(=O)_2R_7$, —$S(O)_yR_7$, —$S(=O)_2NR_{12}R_{12A}$, —$P(=O)(OR_8)_2$, —$OR_{11}$, and a $C_5$–$C_7$ monosaccharide where each hydroxyl group of the monosaccharide is independently either unsubstituted or is replaced by H, $C_1$–$C_4$ alkyl, $C_1$–$C_4$ alkoxy, or —O—C(=O)$R_7$;

$X_1$ is —O—, —S—, —N($R_8$)—;

Y is selected from $C_1$–$C_4$ alkylene, $C_6$–$C_{10}$ arylene, heteroarylene, $C_3$–$C_8$ cycloalkylene, heterocyclylene, —O—, —N($R_8$)—, —S(O)$_y$, —$CR_{8A}$=$CR_{8B}$—, —CH=CH—CH($R_8$)—, —CH($R_8$)—CH=CH—, or —C≡C—; with the proviso that when Y is —O—, —N($R_8$)—, or —S(O)$_y$, m and n cannot be 0; $R_3$ and $R_4$ are the same or different and are each selected from H, $C_1$–$C_6$ alkyl, —OH, and —CH($R_6$)—CONR$_{8A}R_{8B}$, provided that $R_3$ and $R_4$ are not both OH; or $R_3$ and $R_4$, together with the nitrogen to which they are attached, form a 3–7 member heterocyclic ring;

$R_3$ and $R_4$ are the same or different and are each selected from H, $C_1$–$C_6$ alkyl, —OH, and —CH($R_6$)—CONR$_{8A}R_{8B}$, provided that $R_3$ and $R_4$ are not both OH; or $R_3$ and $R_4$, together with the nitrogen to which they are attached, form a 3–7 member heterocyclic ring;

$R_6$ is H, $C_1$–$C_4$ alkyl or the side chain of an a-amino acid;
$R_7$ is $C_1$–$C_6$ alkyl, $C_6$–$C_{10}$ aryl, or heteroaryl;

$R_8$, $R_{8A}$ and $R_{8B}$ are each independently H, $C_1$–$C_4$ alkyl, or $C_6$–$C_{10}$ aryl;

$R_9$ and $R_{10}$ are independently selected from H, $C_1$–$C_4$ alkyl, and $C_6$–$C_{10}$ aryl; or $R_9$ and $R_{10}$ together with the nitrogen to which they are attached, form a 3–7 member heterocyclic ring;

$R_{11}$ is the residue of an amino acid after the hydroxyl group of the carboxyl group is removed;

$R_{12}$ and $R_{12A}$ are each independently selected from H, $C_1$–$C_6$ alkyl, cycloalkyl, $C_6$–$C_{10}$ aryl, and heteroaryl; or $R_{12}$ and $R_{12A}$, together with the nitrogen to which they are attached, form a 5–7 member heterocyclic ring;

$R_{13}$ is H, $C_1$–$C_6$ alkyl, cycloalkyl, $C_6$–$C_{10}$ aryl, heteroaryl, —C(=O)$R_7$, —C(=O)$NR_9R_{10}$, or —C(=S)$NR_9R_{10}$;

m is 0, 1, 2 or 3;
n is 0, 1, 2 or 3;
p is from 1, 2, 3, or 4;
q is 0, 1, or 2;
t is 2, 3, or 4;
y is 0, 1 or 2;

with the proviso that when $Ar_1$ is phenyl and $Ar_2$ is phenyl or pyridyl, then Y cannot be $C_1$–$C_4$ alkylene;

with the further proviso that when $Ar_1$ and $Ar_2$ are phenyl, q=1, m and n=0, Y is

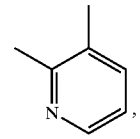

and $R_3$ is H, then $R_4$ is not $C_1$–$C_6$ alkyl;

and the stereoisomeric forms, mixtures of stereoisomeric forms, or pharmaceutically acceptable salt and ester forms thereof.

In an additional embodiment of the invention, there are provided compounds of formula (I):

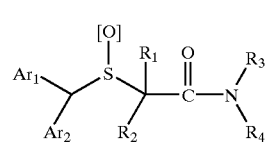

(I)

wherein $Ar_1$ and $Ar_2$ are the same or different and are each selected from thiophene, isothiazole, phenyl, pyridyl, oxazole, isoxazole, thiazole, imidazole, and other five or six membered heterocycles comprising 1–3 atoms of —N—, —O—, or —S—, provided that $Ar_1$ and $Ar_2$ are not both phenyl and when $Ar_1$ is phenyl, $Ar_2$ is not pyridyl; $R_1$—$R_4$ are the same or different and are each selected from H, lower alkyl, —OH, —CH($R_6$)—CONR$_{6A}R_{6B}$, or any of $R_1$—$R_4$ can be taken together to form a 3–7 member carbocyclic or heterocyclic ring, provided that $R_3$ and $R_4$ are not both OH; $R_{6A}$ and $R_{6B}$ are independently H or lower alkyl; and n is 0, 1, or 2; and in addition, each of $Ar_1$ or $Ar_2$ may be independently optionally substituted with one or more substituents independently selected from:

a) H, aryl, heterocyclyl, F, Cl, Br, I, —CN, —$CF_3$, —$NO_2$, —OH, —$OR_7$, —$O(CH_2)_pNR_9R_{10}$, —OC(=O)$R_7$, —OC(=O)$NR_9R_{10}$, —$O(CH_2)_pOR_8$, —$CH_2OR_8$, —$NR_9R_{10}$, —$NR_8S(=O)_2R_7$, —$NR_8C(=O)R_7$, or —$NR_8C(=S)R_7$;

b) —$CH_2OR_{11}$, where $R_{11}$ is the residue of an amino acid after the hydroxyl group of the carboxyl group is removed;

c) —$NR_8C(=O)NR_9R_{10}$, —$NR_8C(=S)NR_9R_{10}$, —$CO_2R_{12}$, —$C(=O)R_{12}$, —$C(=O)NR_9R_{10}$, —$C(=S)NR_9R_{10}$, —$CH=NOR_{12}$, —$CH=NR_7$, —$(CH_2)_pNR_9R_{10}$, —$(CH_2)_pNHR_{11}$, or —$CH=NNR_{12}R_{12A}$, where $R_{12}$ and $R_{12A}$ are the same or different and each are independently selected from H, alkyl of 1 to 4 carbons, —OH, alkoxy of 1 to 4 carbons, —$OC(=O)R_7$, —$OC(=O)NR_9R_{10}$, —$OC(=S)NR_9R_{10}$, —$O(CH_2)_pNR_9R_{10}$, —$O(CH_2)_pOR_8$, substituted or unsubstituted arylalkyl having from 6 to 10 carbons, and substituted or unsubstituted heterocyclylalkyl;

d) —$S(O)_yR_{12}$, —$(CH_2)_pS(O)_yR_7$, —$CH_2S(O)_yR_{11}$ where y is 0, 1 or 2; and e) alkyl of 1 to 8 carbons, alkenyl of 2 to 8 carbons, or alkynyl of 2 to 8 carbons, where:
  1) each alkyl, alkenyl, or alkynyl group is unsubstituted; or
  2) each alkyl, alkenyl or alkynyl group is substituted with 1 to 3 groups selected from aryl of 6 to 10 carbons, heterocyclyl, arylalkoxy, heterocycloalkoxy, hydroxylalkoxy, alkyloxyalkoxy, hydroxyalkylthio, alkoxy-alkylthio, F, Cl, Br, I, —CN, —$NO_2$, —OH, —$OR_7$, —$X_2(CH_2)_pNR_9R_{10}$, —$X_2(CH_2)_pC(=O)NR_9R_{10}$, —$X_2(CH_2)_pC(=S)NR_9R_{10}$, —$X_2(CH_2)_pOC(=O)NR_9R_{10}$, —$X_2(CH_2)_pCO_2R_7$, —$X_2(CH_2)_pS(O)_yR_7$, —$X_2(CH_2)_pNR_8C(=O)NR_9R_{10}$, —$OC(=O)R_7$, —$OC(=O)NHR_{12}$, O-tetrahydropyranyl, —$NR_9R_{10}$, —$NR_8CO_2R_7$, —$NR_8C(=O)NR_9R_{10}$, —$NR_8C(=S)NR_9R_{10}$, —$NHC(=NH)NH_2$, —$NR_8C(=O)R_7$, —$NR_8C(=S)R_7$, —$NR_8S(=O)_2R_7$, —$S(O)_yR_7$, —$CO_2R_{12}$, —$C(=O)NR_9R_{10}$, —$C(=S)NR_9R_{10}$, —$C(=O)R_{12}$, —$CH_2OR_8$, —$CH=NNR_{12}R_{12A}$, —$CH=NOR_{12}$, —$CH=NR_7$, —$CH=NNHCH(N=NH)NH_2$, —$S(=O)_2NR_{12}R_{12A}$, —$P(=O)(OR_8)_2$, —$OR_{11}$, and a monosaccharide of 5 to 7 carbons where each hydroxyl group of the monosaccharide is independently either unsubstituted or is replaced by H, alkyl of 1 to 4 carbons, alkylcarbonyloxy of 2 to 5 carbons, or alkoxy of 1 to 4 carbons, where $X_2$ is O, S, or $NR_8$; where $R_7$ is substituted or unsubstituted alkyl, substituted or unsubstituted aryl, or substituted or unsubstituted heterocyclyl;

$R_8$ is H or alkyl having from 1 to 4 carbons;

p is from 1 to 4; and where either
  1) $R_9$ and $R_{10}$ are each independently H, unsubstituted alkyl of 1 to 4 carbons, or substituted alkyl; or
  2) $R_9$ and $R_{10}$ together form a linking group of the formula —$(CH_2)_2$—$X_1$—$(CH_2)_2$—, wherein $X_1$ is selected from —O—, —S—, and —$CH_2$—;

and the stereoisomeric forms, mixtures of stereoisomeric forms, or pharmaceutically acceptable salt and ester forms thereof.

In a preferred embodiment of the invention, there are provided compounds of formula (I) wherein $Ar_1$ and $Ar_2$ are the same or different and are each selected from thiophene, isothiazole, phenyl, oxazole, isoxazole, thiazole, imidazole, or other five or six membered heterocycles comprising 1–3 atoms of —N—, —O—, or —S—, provided that $Ar_1$ and $Ar_2$ are not both phenyl; $R_1$—$R_4$ are the same or different and are each selected from H, lower alkyl, —OH, —CH($R_6$)—$CONR_{6A}R_{6B}$, or any of $R_1$—$R_4$ can be taken together to form a 3–7 member carbocyclic or heterocyclic ring, provided that $R_3$ and $R_4$ are not both OH; $R_{6A}$ and $R_{6B}$ are independently H or lower alkyl; and n is 0, 1, or 2; and in addition, each of $Ar_1$ or $Ar_2$ may be independently optionally substituted with one or more substituents independently selected from:

a) H, aryl, heterocyclyl, F, Cl, Br, I, —CN, —$CF_3$, —$NO_2$, —OH, —$OR_7$, —$O(CH_2)_pNR_9R_{10}$, —$OC(=O)R_7$, —$OC(=O)NR_9R_{10}$, —$O(CH_2)_pOR_8$, —$CH_2OR_8$, —$NR_9R_{10}$, —$NR_8S(=O)_2R_7$, —$NR_8C(=O)R_7$, or —$NR_8C(=S)R_7$;

b) —$CH_2OR_{11}$, where $R_{11}$ is the residue of an amino acid after the hydroxyl group of the carboxyl group is removed;

c) —$NR_8C(=O)NR_9R_{10}$, —$NR_8C(=S)NR_9R_{10}$, —$CO_2R_{12}$, —$C(=O)R_{12}$, —$C(=O)NR_9R_{10}$, —$C(=S)NR_9R_{10}$, —$CH=NOR_{12}$, —$CH=NR_7$, —$(CH_2)_pNR_9R_{10}$, —$(CH_2)_pNHR_{11}$, or —$CH=NNR_{12}R_{12A}$, where $R_{12}$ and $R_{12A}$ are the same or different and each are independently selected from H, alkyl of 1 to 4 carbons, —OH, alkoxy of 1 to 4 carbons, —$OC(=O)R_7$, —$OC(=O)NR_9R_{10}$, —$OC(=S)NR_9R_{10}$, —$O(CH_2)_pNR_9R_{10}$, —$O(CH_2)_pOR_8$, substituted or unsubstituted arylalkyl having from 6 to 10 carbons, and substituted or unsubstituted heterocyclylalkyl;

d) —$S(O)_yR_{12}$, —$(CH_2)_pS(O)_yR_7$, —$CH_2S(O)_yR_{11}$ where y is 0, 1 or 2; and e) alkyl of 1 to 8 carbons, alkenyl of 2 to 8 carbons, or alkynyl of 2 to 8 carbons, where:
  1) each alkyl, alkenyl, or alkynyl group is unsubstituted; or
  2) each alkyl, alkenyl or alkynyl group is substituted with 1 to 3 groups selected from aryl of 6 to 10 carbons, heterocyclyl, arylalkoxy, heterocycloalkoxy, hydroxylalkoxy, alkyloxyalkoxy, hydroxyalkylthio, alkoxy-alkylthio, F, Cl, Br, I, —CN, —$NO_2$, —OH, —$OR_7$, —$X_2(CH_2)_pNR_9R_{10}$, —$X_2(CH_2)_pC(=O)NR_9R_{10}$, —$X_2(CH_2)_pC(=S)NR_9R_{10}$, —$X_2(CH_2)_pOC(=O)NR_9R_{10}$, —$X_2(CH_2)_pCO_2R_7$, —$X_2(CH_2)_pS(O)_yR_7$, —$X_2(CH_2)_pNR_8C(=O)NR_9R_{10}$, —$OC(=O)R_7$, —$OC(=O)NHR_{12}$, O-tetrahydropyranyl, —$NR_9R_{10}$, —$NR_8CO_2R_7$, —$NR_8C(=O)NR_9R_{10}$, —$NR_8C(=S)NR_9R_{10}$, —$NHC(=NH)NH_2$, —$NR_8C(=O)R_7$, —$NR_8C(=S)R_7$, —$NR_8S(=O)_2R_7$, —$S(O)_yR_7$, —$CO_2R_{12}$, —$C(=O)NR_9R_{10}$, —$C(=S)NR_9R_{10}$, —$C(=O)R_{12}$, —$CH_2OR_8$, —$CH=NNR_{12}R_{12A}$, —$CH=NOR_{12}$, —$CH=NR_7$, —$CH=NNHCH(N=NH)NH_2$, —$S(=O)_2NR_{12}R_{12A}$, —$P(=O)(OR_8)_2$, —$OR_{11}$, and a monosaccharide of 5 to 7 carbons where each hydroxyl group of the monosaccharide is independently either unsubstituted or is replaced by H, alkyl of 1 to 4 carbons, alkylcarbonyloxy of 2 to 5 carbons, or alkoxy of 1 to 4 carbons, where $X_2$ is O, S, or $NR_8$; where $R_7$ is substituted or unsubstituted alkyl, substituted or unsubstituted aryl, or substituted or unsubstituted heterocyclyl;

$R_8$ is H or alkyl having from 1 to 4 carbons;

p is from 1 to 4; and where either
  1) $R_9$ and $R_{10}$ are each independently H, unsubstituted alkyl of 1 to 4 carbons, or substituted alkyl; or
  2) $R_9$ and $R_{10}$ together form a linking group of the formula —$(CH_2)_2$—$X_1$—$(CH_2)_2$—, wherein $X_1$ is selected from —O—, —S—, and —$CH_2$—;

and the stereoisomeric forms, mixtures of stereoisomeric forms, or pharmaceutically acceptable salt and ester forms thereof.

In another embodiment of the invention, there is provided novel compounds of the formula (II-A):

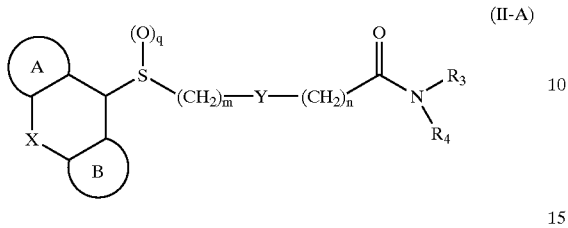

(II-A)

wherein

X is a bond, $-CH_2CH_2-$, $-O-$, $-S(O)_y-$, $-N(R_8)-$, $-CHN(R_8)-$, $-CH=CH-$, $-CH_2-CH=CH-$, $C(=O)$, $-C(R_8)=N-$, $-N=C(R_8)-$, $-C(=O)-N(R_8)-$, or $-NR_8-C(=O)-$;

Rings A and B, together with the carbon atoms to which they are attached, are each independently selected from:
  a) a 6-membered aromatic carbocyclic ring in which from 1 to 3 carbon atoms may be replaced by hetero atoms selected from oxygen, nitrogen and sulfur; and
  b) a 5-membered aromatic carbocyclic ring in which either:
    i) one carbon atom is replaced with an oxygen, nitrogen, or sulfur atom;
    ii) two carbon atoms are replaced with a sulfur and a nitrogen atom, an oxygen and a nitrogen atom, or two nitrogen atoms; or
    iii) three carbon atoms are replaced with three nitrogen atoms, one oxygen and two nitrogen atoms, or one sulfur and two nitrogen atoms;

wherein Ring A and Ring B may each independently be substituted with 1–3 substituents selected from:
  a) H, $C_6$–$C_{10}$ aryl, heteroaryl, F, Cl, Br, I, $-CN$, $-CF_3$, $-NO_2$, $-OH$, $-OR_7$, $-O(CH_2)_pNR_9R_{10}$, $-OC(=O)R_7$, $-OC(=O)NR_9R_{10}$, $-O(CH_2)_pOR_8$, $-CH_2OR_8$, $-NR_9R_{10}$, $-NR_8S(=O)_2R_7$, $-NR_8C(=O)R_7$, or $-NR_8C(=S)R_7$;
  b) $-CH_2OR_{11}$;
  c) $-NR_8C(=O)NR_8R_{10}$, $-NR_8C(=S)NR_9R_{10}$, $-CO_2R_{12}$, $-C(=O)R_{13}$, $-C(=O)NR_9R_{10}$, $-C(=S)NR_9R_{10}$, $-CH=NOR_{12}$, $-CH=NR_7$, $-(CH_2)_pNR_9R_{10}$, $-(CH_2)_pNHR_{11}$, $-CH=NNR_{12}R_{12A}$, $-C(=NR_8)NR_{8A}R_{8B}$, $-NR_8C(=NH)R_{8A}$, $-NR_8C(=NH)NR_{8A}R_{8B}$,

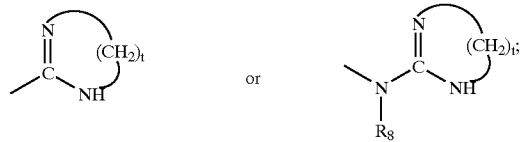

d) $-S(O)_yR_7$, $-(CH_2)_pS(O)_yR_7$, $-CH_2S(O)_yR_7$; and
  e) $C_1$–$C_8$ alkyl, $C_2$–$C_8$ alkenyl, or $C_2$–$C_8$ alkynyl, where:
    1) each alkyl, alkenyl, or alkynyl group is unsubstituted; or
    2) each alkyl, alkenyl or alkynyl group is independently substituted with 1 to 3 groups independently selected from $C_6$–$C_{10}$ aryl, heteroaryl, F, Cl, Br, I, $CF_3$, $-CN$, $-NO_2$, $-OH$, $-OR_7$, $-CH_2OR_8$, $-NR_9R_{10}$, $-O-(CH_2)_p-OH$, $-S-(CH_2)_p-OH$, $-X_1(CH_2)_pOR_7$, $X_1(CH_2)_pNR_9R_{10}$, $-X_1(CH_2)_pC(=O)NR_9R_{10}$, $-X_1(CH_2)_pC(=S)NR_9R_{10}$, $-X_1(CH_2)_pOC(=O)NR_9R_{10}$, $-X_1(CH_2)_pCO_2R_8$, $-X_1(CH_2)_pS(O)_yR_7$, $-X_1(CH_2)_pNR_8C(=O)NR_9R_{10}$, $-C(=O)R_{13}$, $-CO_2R_{12}$, $-OC(=O)R_7$, $-C(=O)NR_9R_{10}$, $-OC(=O)NR_{12}R_{12A}$, O-tetrahydropyranyl, $-C(=S)NR_9R_{10}$, $-CH=NNR_{12}R_{12A}$, $-CH=NOR_{12}$, $-CH=NR_7$, $-CH=NNHCH(N=NH)NH_2$, $-NR_8CO_2R_7$, $-NR_8C(=O)NR_9R_{10}$, $-NR_8C(=S)NR_9R_{10}$, $-NHC(=NH)NH_2$, $-NR_8C(=O)R_7$, $-NR_8C(=S)R_7$, $-NR_8S(=O)_2R_7$, $-S(O)_yR_7$, $-S(=O)_2NR_{12}R_{12A}$, $-P(=O)(OR_8)_2$, $-OR_{11}$, and a $C_5$–$C_7$ monosaccharide where each hydroxyl group of the monosaccharide is independently either unsubstituted or is replaced by H, $C_1$–$C_4$ alkyl, $C_1$–$C_4$ alkoxy, or $-O-C(=O)R_7$; $R_3$ and $R_4$ are the same or different and are each selected from H, $C_1$–$C_6$ alkyl, $-OH$, $-CH(R_6)-CONR_{8A}R_{8B}$, provided that $R_3$ and $R_4$ are not both OH, or $R_3$ and $R_4$, together with the nitrogen to which they are attached, form a 3–7 member heterocyclic ring;

$R_3$ and $R_4$ are the same or different and are each selected from H, $C_1$–$C_6$ alkyl, $-OH$, and $-CH(R_6)-CONR_{8A}R_{8B}$, provided that $R_3$ and $R_4$ are not both OH; or $R_3$ and $R_4$, together with the nitrogen to which they are attached, form a 3–7 member heterocyclic ring;

$R_6$ is H, $C_1$–$C_4$ alkyl or the side chain of an a-amino acid;
$R_7$ is $C_1$–$C_6$ alkyl, $C_6$–$C_{10}$ aryl, or heteroaryl;
$R_8$, $R_{8A}$ and $R_{8B}$ are each independently H, $C_1$–$C_4$ alkyl, or $C_6$–$C_{10}$ aryl;
$R_9$ and $R_{10}$ are independently selected from H, $C_1$–$C_4$ alkyl, and $C_6$–$C_{10}$ aryl; or $R_9$ and $R_{10}$ together with the nitrogen to which they are attached, form a 3–7 member heterocyclic ring;
$R_{11}$ is the residue of an amino acid after the hydroxyl group of the carboxyl group is removed;
$R_{12}$ and $R_{12A}$ are each independently selected from H, $C_1$–$C_6$ alkyl, cycloalkyl, $C_6$–$C_{10}$ aryl, and heteroaryl; or $R_{12}$ and $R_{12A}$, together with the nitrogen to which they are attached, form a 5–7 member heterocyclic ring;
$R_{13}$ is H, $C_1$–$C_6$ alkyl, cycloalkyl, $C_6$–$C_{10}$ aryl, heteroaryl, $-C(=O)R_7$, $-C(=O)NR_9R_{10}$, or $-C(=S)NR_9R_{10}$;
$X_1$ is $-O-$, $-S-$, $-N(R_8)-$;
Y is selected from $C_1$–$C_4$ alkylene, $C_6$–$C_{10}$ arylene, heteroarylene, $C_3$–$C_8$ cycloalkylene, heterocyclylene, $-O-$, $-N(R_8)-$, $-S(O)_y-$, $-CR_{8A}=CR_{8B}-$, $-CH=CH-CH(R_8)-$, $-CH(R_8)-CH=CH-$, or $-C\equiv C-$; with the proviso that when Y is $-O-$, $-N(R_8)-$, or $-S(O)_y$, m and n cannot be 0;
m is 0, 1, 2 or 3;
n is 0, 1, 2 or 3;
p is from 1 to 4;
q is 0, 1, 2;
t is 2, 3, or 4;
y is 0, 1 or 2;
and the stereoisomeric forms, mixtures of stereoisomeric forms, or pharmaceutically acceptable salt and ester forms thereof.

In a further embodiment, there are provided compounds of formula (II):

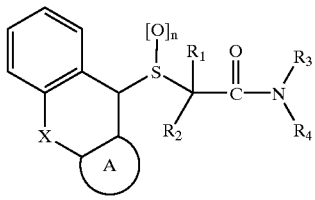

(II)

where X is —(CH$_2$)$_m$—, —O—, —S(O)$_n$—, —N(R$_5$)—, —CH=CH—, or —CH$_2$—CH=CH—; m is 0, 1, 2 or 3; n is 0, 1 or 2; R$_1$–R$_4$ are the same or different and are each selected from H, lower alkyl, —OH, —CH(R$_6$)—CONR$_7$R$_8$, or any of R$_1$–R$_4$ can be taken together to form a 3–7 member carbocyclic or heterocyclic ring; R$_5$ is H, lower alkyl, or —OH; R$_6$, R$_7$ and R$_8$ is H or lower alkyl; and ring A, together with the carbon atoms to which it is attached is selected from:
a) a 6-membered carbocyclic ring in which from 1 to 3 carbon atoms may be replaced by hetero atoms selected from oxygen, nitrogen and sulfur; and
b) a 5-membered carbocyclic ring in which either:
  i) one carbon atom may be replaced with an oxygen, nitrogen, or sulfur atom;
  ii) two carbon atoms may be replaced with a sulfur and a nitrogen atom, an oxygen and a nitrogen atom, or two nitrogen atoms; or
  iii) three carbon atoms may be replaced with three nitrogen atoms, one oxygen and two nitrogen atoms, or one sulfur and two nitrogen atoms;
and the stereoisomeric forms, mixtures of stereoisomeric forms, or pharmaceutically acceptable salt and ester forms thereof.

As with any group of structurally related compounds which possess a particular utility, certain groups and configurations are preferred for the compounds of the present invention in their end-use application.

In some embodiments of formula (I-A) or (II-A), Y≡C(R$_1$)(R$_2$), wherein R$_1$ and R$_2$ are each independently selected from H or C$_1$–C$_6$ alkyl; and optionally, either R$_1$ or R$_2$ can combine with either R$_3$ or R$_4$ to form a 5–7 membered heterocyclic ring. In some particular embodiments, R$_1$ combines with R$_3$ to form compounds (III) and (IV):

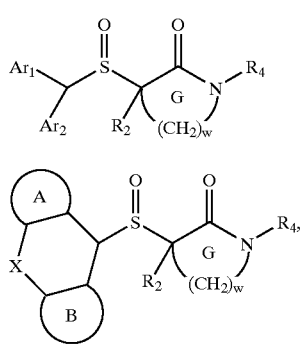

wherein w is 2, 3, or 4.

In certain embodiments of formula (I-A), Ar$_1$ and Ar$_2$ are each independently selected from a five or six membered heteroaryl comprising 1–3 atoms of —N—, —O—, or —S—. Preferably, q=1. In preferred embodiments, Ar$_1$ and Ar$_2$ are each independently selected from thienyl, isothiazolyl, pyridyl, oxazolyl, isoxazolyl, thiazolyl, and imidazolyl, and more preferably, Ar$_1$ and Ar$_2$ are thienyl, and particularly Ar$_1$ and Ar$_2$ are 3-thienyl. In other preferred embodiments, Y is —O—, —S(O)$_y$—, or —N(R$_8$)—. In another preferred embodiment, Y is C$_1$–C$_4$ alkylene. In an additional embodiment, Y is —CR$_{8A}$=CR$_{8B}$—, —CH=CH—CH(R$_8$)—, —CH(R$_8$)—CH=CH—, or —C≡C—. In certain preferred embodiments, Y is C$_6$–C$_{10}$ arylene or heteroarylene, and preferably, m=0 or 1 and n=0 or 1. More preferably, Y is

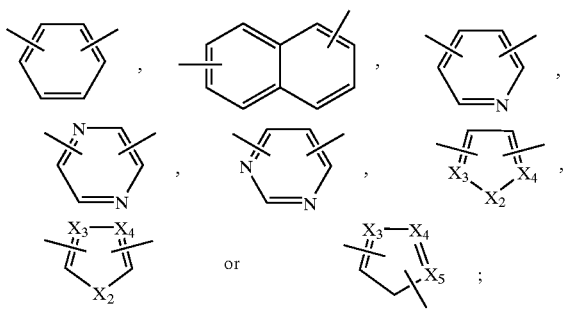

wherein X$_2$ is —CH$_2$—, —O—, —S(O)$_y$—, or —N(R$_8$)—; and X$_3$, X$_4$, and X$_5$ are each independently selected from —CH—, or —N—. Most preferably, Y is phenylene. In another more preferred embodiment, Y is

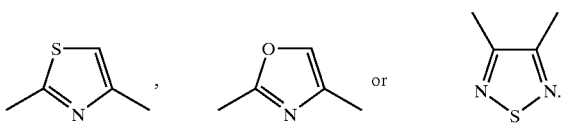

In yet another embodiment, Y is furanylene. In further preferred embodiments, Y is C$_3$–C$_8$ cycloalkylene or heterocyclylene. Preferably, Y is

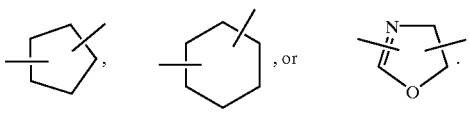

In other embodiments of formula (I-A), Ar$_1$ is phenyl and Ar$_2$ is a five or six membered heteroaryl comprising 1–3 atoms of —N—, —O—, or —S—. Preferably, q=1. In other preferred embodiments, Ar$_1$ and Ar$_2$ are each independently phenyl, thienyl, isothiazolyl, pyridyl, oxazolyl, isoxazolyl, thiazolyl, and imidazolyl. In further preferred embodiments, Ar$_1$ is phenyl and Ar$_2$ is thienyl, isothiazolyl, pyridyl, oxazolyl, isoxazolyl, thiazolyl, and imidazolyl, and more preferably, Ar$_1$ is phenyl and Ar$_2$ is thienyl, and particularly, Ar$_2$ is 3-thienyl. In other preferred embodiments, Y is —O—, —S(O)$_y$—, or —N(R$_8$)—. In another preferred embodiment, Y is C$_1$–C$_4$ alkylene. In an additional embodiment, Y is —CR$_{8A}$=CR$_{8B}$—, —CH=CH—CH(R$_8$)—, —CH(R$_8$)—CH=CH—, or —C≡C—. In certain preferred embodiments, Y is C$_6$–C$_{10}$ arylene or heteroarylene, and preferably, m=0 or 1 and n=0 or 1. More preferably, Y is

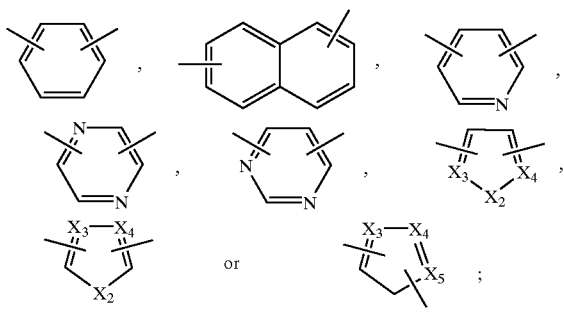

wherein $X_2$ is —$CH_2$—, —O—, —$S(O)_y$—, or —$N(R_8)$—; and $X_3$, $X_4$, and $X_5$ are each independently selected from —CH—, or —N—. Most preferably, Y is phenylene. In another more preferred embodiment, Y is

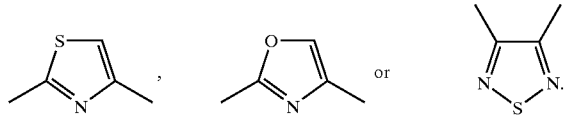

In yet another embodiment, Y is furanylene. In further preferred embodiments, Y is $C_3$-$C_8$ cycloalkylene or heterocyclylene. Preferably, Y is

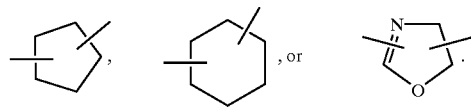

In another embodiment of formula (I-A), $Ar_1$ and $Ar_2$ is phenyl. Preferably, q=1. In other preferred embodiments, Y is —O—, —$S(O)_y$—, or —$N(R_8)$—. In another preferred embodiment, Y is $C_1$-$C_4$ alkylene. In an additional embodiment, Y is —$CR_{8A}$=$CR_{8B}$—, —CH=CH—CH($R_8$)—, —CH($R_8$)—CH=CH—, or —C≡C—. In certain preferred embodiments, Y is $C_6$-$C_{10}$ arylene or heteroarylene, and preferably, m=0 or 1 and n=0 or 1. More preferably, Y is

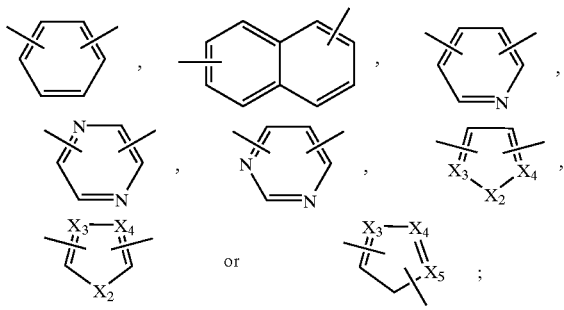

wherein $X_2$ is —$CH_2$—, —O—, —$S(O)_y$—, or —$N(R_8)$—; and $X_3$, $X_4$, and $X_5$ are each independently selected from —CH—, or —N—. Most preferably, Y is phenylene. In another more preferred embodiment, Y is

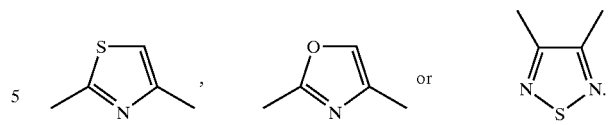

In yet another embodiment, Y is furanylene. In further preferred embodiments, Y is $C_3$-$C_8$ cycloalkylene or heterocyclylene. Preferably, Y is

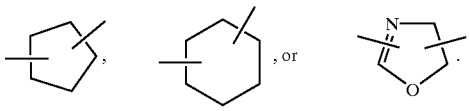

In an additional embodiment of formula (I-A), Y is —O—, —$S(O)_y$—, —$N(R_8)$—, $C_1$-$C_4$ alkylene, —$CR_{8A}$=$CR_{8B}$—, —CH=CH—CH($R_8$)—, —CH($R_8$)—CH=CH—, —C≡C—,

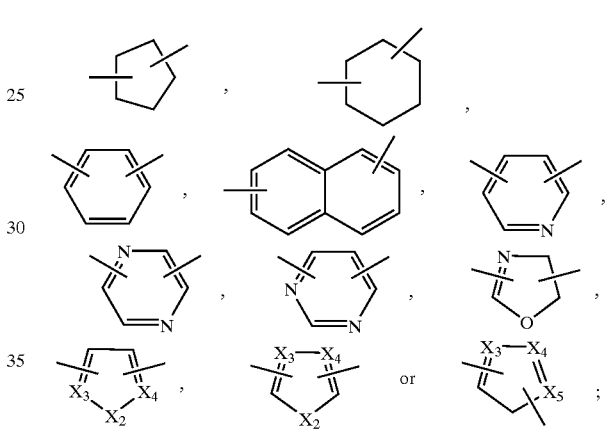

wherein $X_2$ is —$CH_2$—, —O—, —$S(O)_y$—, or —$N(R_8)$—; and $X_3$, $X_4$, and $X_5$ are each independently selected from —CH—, or —N—. In other preferred embodiments, Y is —O—, —$S(O)_y$—, or —$N(R_8)$—. In another preferred embodiment, Y is $C_1$-$C_4$ alkylene. In an additional embodiment, Y is —$CR_{8A}$=$CR_{8B}$—, —CH=CH—CH($R_8$)—, —CH($R_8$)—CH=CH—, or —C≡C—. In certain preferred embodiments, Y is $C_6$-$C_{10}$ arylene or heteroarylene, and preferably, m=0 or 1 and n=0 or 1. More preferably, Y is

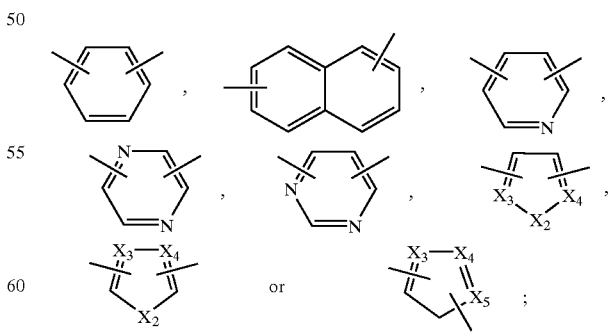

wherein $X_2$ is —$CH_2$—, —O—, —$S(O)_y$—, or —$N(R_8)$—; and $X_3$, $X_4$, and $X_5$ are each independently selected from —CH—, or —N—. Most preferably, Y is phenylene. In another more preferred embodiment, Y is

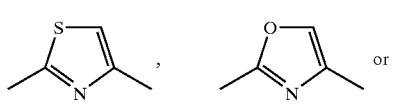 or 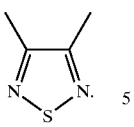

In yet another embodiment, Y is furanylene. In further preferred embodiments, Y is $C_3$–$C_8$ cycloalkylene or heterocyclylene. Preferably, Y is

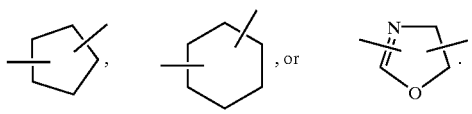

In yet another embodiment of formula (I-A), q=1.

In a further embodiment of formula (I-A), $Ar_1$ and $Ar_2$ are each independently selected from phenyl and thienyl, and q=1. Preferably $Ar_1$ and $Ar_2$ are each independently selected from phenyl and 3-thienyl, and q=1. In other preferred embodiments, Y is —O—, —S(O)$_y$—, or —N($R_8$)—. In another preferred embodiment, Y is $C_1$–$C_4$ alkylene. In an additional embodiment, Y is —CR$_{8A}$=CR$_{8B}$—, —CH=CH—CH($R_8$)—, —CH($R_8$)—CH=CH—, or —C≡C—. In certain preferred embodiments, Y is $C_6$–$C_{10}$ arylene or heteroarylene, and preferably, m=0 or 1 and n=0 or 1. More preferably, Y is

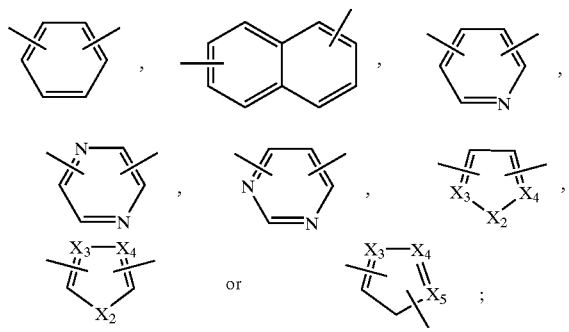

wherein $X_2$ is —CH$_2$—, —O—, —S(O)$_y$—, or —N($R_8$)—; and $X_3$, $X_4$, and $X_5$ are each independently selected from —CH—, or —N—. Most preferably, Y is phenylene. In another more preferred embodiment, Y is

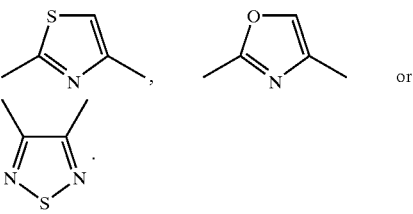

In yet another embodiment, Y is furanylene. In further preferred embodiments, Y is $C_3$–$C_8$ cycloalkylene or heterocyclylene. Preferably, Y is

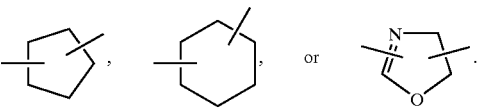

Preferred embodiments of formula (I-A) are compounds wherein $Ar_1$ and $Ar_2$ are the same or different and are each selected from thiophene, isothiazole, phenyl, pyridyl, oxazole, isoxazole, thiazole, imidazole, provided that $Ar_1$ and $Ar_2$ are both not phenyl and when $Ar_1$ is phenyl, $Ar_2$ is not pyridyl.

Preferred embodiments of formula (I) are compounds wherein $Ar_1$ and $Ar_2$ are the same or different and are each selected from thiophene, isothiazole, phenyl, oxazole, isoxazole, thiazole, imidazole, provided that $Ar_1$ and $Ar_2$ are both not phenyl. Other preferred embodiments are those where $Ar_1$ and $Ar_2$ are each independently substituted.

Additional preferred embodiments of formula (I) are given below:
1) Compounds in which $Ar_1$, $Ar_2$ or both are thiophene;
2) Compounds in which $Ar_1$, $Ar_2$ or both are isothiazole;
3) Compounds in which $Ar_1$, $Ar_2$ or both are pyridyl;
4) Compounds in which $Ar_1$, $Ar_2$ or both are oxazole;
5) Compounds in which $Ar_1$, $Ar_2$ or both are isoxazole;
6) Compounds in which $Ar_1$, $Ar_2$ or both are thiazole;
7) Compounds in which $Ar_1$, $Ar_2$ or both are imidazole,
8) Compounds in which $Ar_1$ is phenyl and $Ar_2$ is thiophene.

In a preferred embodiment of the of formula (I-A), there are provided compounds as represented in Table 1:

TABLE 1

| No. | $Ar_1$ | $Ar_2$ | Y | m | n | $NR_3R_4$ |
|---|---|---|---|---|---|---|
| I-1 | 3-Thienyl | 3-Thienyl | —CH$_2$— | 1 | 0 | NH$_2$ |
| I-2 | 3-Thienyl | 3-Thienyl | —CH$_2$— | 1 | 0 | NMe$_2$ |
| I-3 | 3-Thienyl | 3-Thienyl | —CH$_2$— | 2 | 1 | NH$_2$ |
| I-4 | 3-Thienyl | 3-Thienyl | —CH$_2$— | 1 | 0 | NHCH(CH$_3$)—CONH$_2$ |
| I-5 | 3-Thienyl | 3-Thienyl | —C(CH$_3$)$_2$— | 1 | 0 | NH$_2$ |
| I-6 | 3-Thienyl | 3-Thienyl | 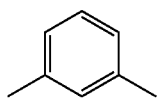 | 1 | 0 | NH$_2$ |

TABLE 1-continued

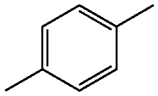

| No. | Ar$_1$ | Ar$_2$ | Y | m | n | NR$_3$R$_4$ |
|---|---|---|---|---|---|---|
| I-7 | Ph | 3-Thienyl |  | 1 | 0 | NH$_2$ |
| I-8 | Ph | 3-Thienyl | —CH$_2$— | 2 | 1 | NH$_2$ |
| I-9 | 3-Thienyl | 3-Thienyl | —CH$_2$— | 0 | 0 | NH$_2$ |
| I-10 | 3-Thienyl | 3-Thienyl | —CH$_2$— | 0 | 0 | NH(C$_3$H$_7$) |
| I-11 | 3-Thienyl | 3-Thienyl | —CH$_2$— | 0 | 0 | N(CH$_3$)$_2$ |
| I-12 | 3-Thienyl | 3-Thienyl | —CH$_2$— | 0 | 0 | N(CH$_2$CH$_3$)$_2$ |
| I-13 | 3-Thienyl | 3-Thienyl | —CH$_2$— | 0 | 0 | morpholino |
| I-14 | 3-Isothiazolyl | 3-Isothiazolyl | —CH$_2$— | 0 | 0 | NH$_2$ |
| I-15 | 4-Thiazolyl | 4-Thiazolyl | —CH$_2$— | 0 | 0 | NH$_2$ |
| I-16 | 2-Thiazolyl | 2-Thiazolyl | —CH$_2$— | 0 | 0 | NH$_2$ |
| I-17 | 3-Isoxazolyl | 3-Isoxazolyl | —CH$_2$— | 0 | 0 | NH$_2$ |
| I-18 | 4-Oxazolyl | 4-Oxazolyl | —CH$_2$— | 0 | 0 | NH$_2$ |
| I-19 | 2-Oxazolyl | 2-Oxazolyl | —CH$_2$— | 0 | 0 | NH$_2$ |
| I-20 | 4-Imidazolyl | 4-Imidazolyl | —CH$_2$— | 0 | 0 | NH$_2$ |
| I-21 | 2-Imidazolyl | 2-Imidazolyl | —CH$_2$— | 0 | 0 | NH$_2$ |
| I-22 | Phenyl | 3-Thienyl | —CH$_2$— | 0 | 0 | NH$_2$ |
| I-23 | 2-Pyridyl | 2-Pyridyl | —CH$_2$— | 0 | 0 | NH$_2$ |
| I-24 | 3-Pyridyl | 3-Pyridyl | —CH$_2$— | 0 | 0 | NH$_2$ |
| I-25 | 4-Pyridyl | 4-Pyridyl | —CH$_2$— | 0 | 0 | NH$_2$ |
| I-26 | 3-Thienyl | 3-Thienyl | —CH$_2$— | 0 | 0 | NH(CH$_2$)$_2$OH |
| I-27 | 3-Thienyl | 3-Thienyl | —CH$_2$— | 0 | 0 | NH(CH$_2$)$_2$-N-piperidyl |
| I-28 | 3-Thienyl | 3-Thienyl | —CH$_2$— | 0 | 0 | NH(CH$_2$)$_2$-N-morpholinoyl |
| I-29 | 3-Thienyl | 3-Thienyl | —CH$_2$— | 0 | 0 | NH(CH$_3$) |
| I-30 | 3-Thienyl | 3-Thienyl | —CH$_2$— | 0 | 0 | NH(CH$_2$-[2-pyridyl]) |
| I-31 | 3-Thienyl | 3-Thienyl | —CH$_2$— | 0 | 0 | NH(CH$_2$-[3-pyridyl]) |
| I-32 | 3-Thienyl | 3-Thienyl | —CH$_2$— | 0 | 0 | NH(CH$_2$-[4-pyridyl]) |
| I-33 | 3-Thienyl | 3-Thienyl | —CH$_2$— | 0 | 0 |  |
| I-34 | 3-Thienyl | 3-Thienyl | —CH$_2$— | 0 | 0 | 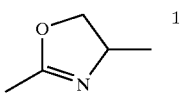 |
| I-35 | 3-Thienyl | 3-Thienyl | 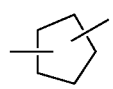 | 1 | 0 | NH$_2$ |
| I-36 | Phenyl | 3-Thienyl | —CH$_2$— | 1 | 0 | NH$_2$ |
| I-37 | 2-Thiazolyl | Phenyl | —CH$_2$— | 0 | 0 | NH$_2$ |
| I-38 | 2-Thiazolyl | 2-Thienyl | —CH$_2$— | 0 | 0 | NH$_2$ |

In certain preferred embodiments of the present invention, there are provided compounds of formula (II) or (II-A) where q=1.

In another embodiment of formula (II-A), X is a bond, —CH$_2$CH$_2$—, —O—, —N(CH$_3$)—, or —CH=CH—, and preferably X is a bond.

In certain embodiments of formula (II-A), Y is —O—, —S(O)$_y$, —N(R$_8$)—, C$_1$-C$_4$ alkylene, —CR$_{8A}$=CR$_{8B}$—, —CH=CH—CH(R$_8$)—, —CH(R$_8$)—CH=CH—, —C≡C—,

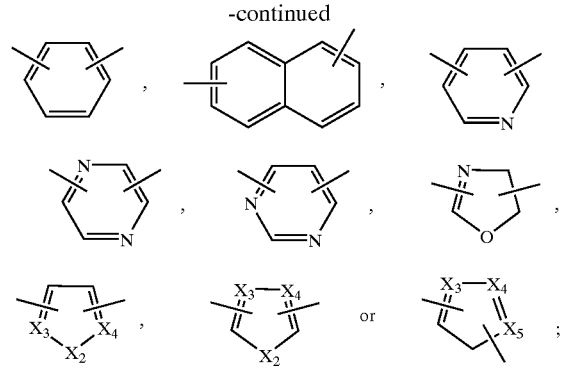

wherein $X_2$ is —$CH_2$—, —O—, —$S(O)_y$—, or —$N(R_8)$—; and $X_3$, $X_4$, and $X_5$ are each independently selected from —CH—, or —N—. In other preferred embodiments, Y is —O—, —$S(O)_y$—, or —$N(R_8)$—. In another preferred embodiment, Y is $C_1$–$C_4$ alkylene. In an additional embodiment, Y is —$CR_{8A}$=$CR_{8B}$—, —CH=CH—CH($R_8$)—, —CH($R_8$)—CH=CH—, or —C≡C—. In certain preferred embodiments, Y is $C_6$–$C_{10}$ arylene or heteroarylene, and preferably, m=0 or 1 and n=0 or 1. More preferably, Y is

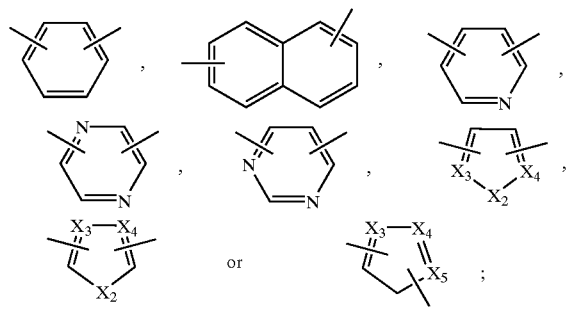

wherein $X_2$ is —$CH_2$—, —O—, —$S(O)_y$—, or —$N(R_8)$—; and $X_3$, $X_4$, and $X_5$ are each independently selected from —CH—, or —N—. Most preferably, Y is phenylene. In another more preferred embodiment, Y is

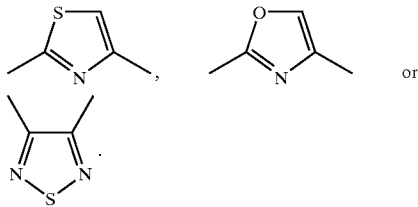

In further preferred embodiments, Y is $C_3$–$C_8$ cycloalkylene or heterocyclylene. Preferably, Y is

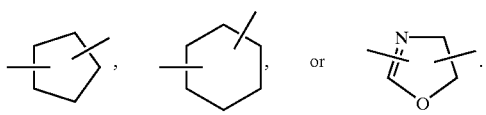

In additional embodiments of formula (II-A), rings A and B, together with the carbon atoms to which they are attached, are each independently selected from phenylene, thienylene, isothiazolylene, pyridylene, oxazolylene, isoxazolylene, thiazolylene, imidazolylene. In a preferred embodiment, ring A is phenylene, and more preferably, rings A and B are phenylene. In another preferred embodiment, rings A and B are thienylene, and more preferably, rings A and B are 2,3-thienylene. In preferred embodiments, q=1. In further preferred embodiments, ring A is phenylene and ring B is 2,3-thienylene. In other preferred embodiments, X is a bond, —$CH_2CH_2$—, —O—, —$N(CH_3)$—, or —CH=CH—. In a more preferred embodiment, Y is —O—, —$S(O)_y$—, —$N(R_8)$—, $C_1$–$C_4$ alkylene, —$CR_{8A}$=$CR_{8B}$—, —CH=CH—CH($R_8$)—, —CH($R_8$)—CH=CH—, —C≡C—,

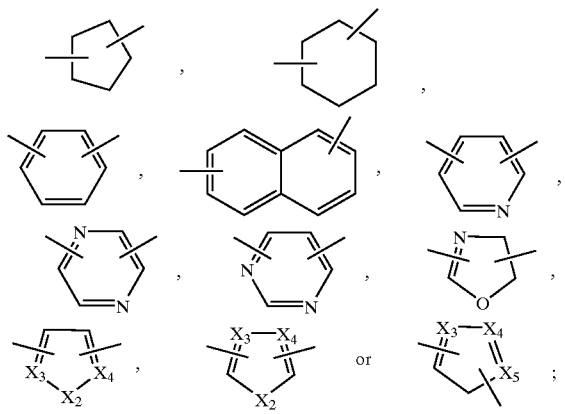

wherein $X_2$ is —$CH_2$—, —O—, —$S(O)_y$—, or —$N(R_8)$—, and $X_3$, $X_4$, and $X_5$ are each independently selected from —CH—, or —N—. In other preferred embodiments, Y is —O—, —$S(O)_y$—, or —$N(R_8)$—. In another preferred embodiment, Y is $C_1$–$C_4$ alkylene. In an additional embodiment, Y is —$CR_{8A}$=$CR_{8B}$—, —CH=CH—CH($R_8$)—, —CH($R_8$)—CH=CH—, or —C≡C—. In certain preferred embodiments, Y is $C_6$–$C_{10}$ arylene or heteroarylene, and preferably, m=0 or 1 and n=0 or 1. More preferably, Y is

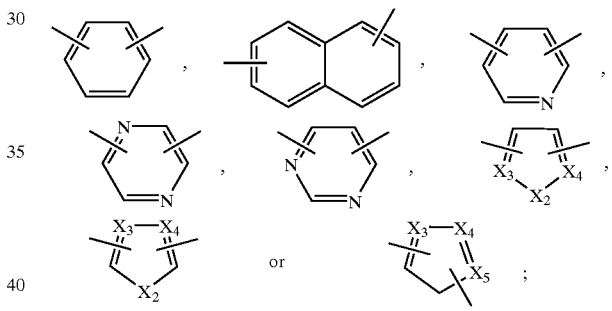

wherein $X_2$ is —$CH_2$—, —O—, —$S(O)_y$—, or —$N(R_8)$—; and $X_3$, $X_4$, and $X_5$ are each independently selected from —CH—, or —N—. Most preferably, Y is phenylene. In another more preferred embodiment, Y is

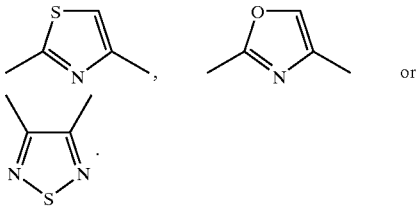

In further preferred embodiments, Y is $C_3$-$C_8$ cycloalkylene or heterocyclylene. Preferably, Y is

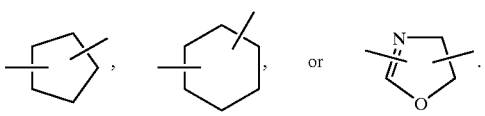

In an especially preferred embodiment, X is a bond, and Y is —$CH_2$— and n=0.

Preferred embodiments of formula (II) are compounds wherein ring A is selected from thiophene, isothiazole, phenyl, oxazole, isoxazole, thiazole, and imidazole. Other preferred embodiments are those where the benzo ring and ring A are each independently substituted.

Other preferred embodiments of formula (II) are given below:

1) Compounds in which A is benzo and X is a bond, i.e. —$(CH_2)_m$—, where m=0;
2) Compounds in which A is benzo and X is —O—;
3) Compounds in which A is benzo and X is —$NCH_3$;
4) Compounds in which A is benzo and X is —S—; and
5) Compounds in which $R_3$ and $R_4$ are taken together with the nitrogen to which they are attached to form a morpholine ring.

In a particularly preferred embodiment of formula (II-A), there are provided compounds as represented in Table 2:

TABLE 2

(II-A)

| No. | A | B | X | Y | m | n | $NR_3R_4$ |
|---|---|---|---|---|---|---|---|
| II-1 | Bnezo | Benzo | bond | —$CH_2$— | 1 | 0 | $NH_2$ |
| II-2 | Benzo | Benzo | bond | —$CH_2$— | 1 | 0 | $NMe_2$ |
| II-3 | Benzo | Benzo | bond | —$CH_2$— | 1 | 1 | $NH_2$ |
| II-4 | Benzo | Benzo | bond | —$CH_2$— | 1 | 0 | $NHCH(CH_3)$—$CONH_2$ |
| II-5 | Benzo | Benzo | bond | —$CH_2$— | 1 | 0 | morpholino |
| II-6 | Benzo | Benzo | bond | —$CH_2$— | 2 | 1 | $NH_2$ |
| II-7 | Benzo | Benzo | bond | —$CH_2$— | 2 | 1 | $NMe_2$ |
| II-8 | Benzo | Benzo | bond | —$CH(CH_3)$— | 1 | 0 | $NH_2$ |
| II-9 | Benzo | Benzo | bond | —$CH_2$— | 0 | 0 | $NHCH(CH_3)$—$CONH_2$ |
| II-10 | Benzo | Benzo | bond | *m-phenylene* | 1 | 0 | $NH_2$ |
| II-11 | Benzo | Benzo | bond | —$C(CH_3)_2$— | 1 | 0 | $NH_2$ |
| II-12 | Benzo | Benzo | bond | *p-phenylene* | 1 | 0 | $NH_2$ |
| II-13 | Benzo | Benzo | —$CH_2CH_2$— | —$CH_2$— | 1 | 0 | $NH_2$ |
| II-14 | Benzo | Benzo | —$CH_2CH_2$— | —$CH(CH_3)$— | 1 | 0 | $NH_2$ |
| II-15 | Benzo | Benzo | bond | *4,5-dihydrooxazole* | 1 | 0 | $NH_2$ |
| II-16 | Benzo | Benzo | bond | *thiazole* | 1 | 0 | $NH_2$ |
| II-17 | Benzo | Benzo | bond | *thiazole* | 1 | 0 | $NMe_2$ |
| II-18 | Benzo | Benzo | —CH=CH— | —$CH_2$— | 2 | 1 | $NH_2$ |
| II-19 | Benzo | Benzo | —CH=CH— | —$C(CH_3)_2$— | 1 | 0 | $NH_2$ |
| II-20 | Benzo | Benzo | —O— | —$CH_2$— | 2 | 1 | $NH_2$ |
| II-21 | Benzo | Benzo | —O— | —$CH(CH_3)$— | 1 | 0 | $NH_2$ |
| II-22 | 2,3-Thieno | 2,3-Thieno | bond | —$CH_2$— | 0 | 0 | $NH_2$ |
| II-23 | Benzo | Benzo | bond | —$CH_2$— | 0 | 0 | $NH_2$ |
| II-24 | Benzo | Benzo | bond | —$CH_2$— | 0 | 0 | $NHCH(CH_3)$—$CONMe_2$ |
| II-25 | Benzo | Benzo | —$CH_2CH_2$— | —$CH_2$— | 0 | 0 | $NH_2$ |
| II-26 | Benzo | Benzo | —$CH_2CH_2$— | —$CH_2$— | 0 | 0 | $N(CH_3)_2$ |
| II-27 | Benzo | Benzo | —O— | —$CH_2$— | 0 | 0 | $NH_2$ |

TABLE 2-continued

(II-A)

| No. | A | B | X | Y | m | n | NR₃R₄ |
|---|---|---|---|---|---|---|---|
| II-28 | Benzo | Benzo | —N(CH₃)— | —CH₂— | 0 | 0 | NH₂ |
| II-29 | Benzo | Benzo | —S— | —CH₂— | 0 | 0 | NH₂ |
| II-30 | Benzo | Benzo | bond | —CH₂— | 0 | 0 | NH(CH₃) |
| II-31 | Benzo | Benzo | bond | —CH₂— | 0 | 0 | NH(CH₂CH₂—NH[t-Boc]) |
| II-32 | Benzo | Benzo | bond | —CH₂— | 0 | 0 | NH(CH₂-[2-pyridyl]) |
| II-33 | Benzo | Benzo | bond | —CH₂— | 0 | 0 | NH(CH₂-[3-pyridyl]) |
| II-34 | Benzo | Benzo | bond | —CH₂— | 0 | 0 | NH(CH₂CH₂OH) |
| II-35 | Benzo | Benzo | bond | —CH₂— | 0 | 0 | N(CH₃)₂ |
| II-36 | Benzo | Benzo | bond | —CH₂— | 0 | 0 | 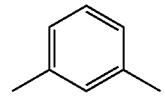 |
| II-37 | Benzo | Benzo | —CH=CH— | —CH₂— | 0 | 0 | NH₂ |
| II-38 | Benzo | Benzo | bond | 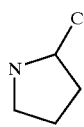 | 1 | 0 | N(CH₃)₂ |
| II-39 | Benzo | Benzo | bond | —CH₂— | 0 | 0 | NHOH |
| II-40 | Benzo | Benzo | bond | —CH₂— | 0 | 0 | NHCH₂CONH₂ |
| II-41 | Benzo | Benzo | bond | —CH₂— | 0 | 0 | NH(CH₂)₂—CONH₂ |
| II-42 | Benzo | Benzo | bond | —CH₂— | 0 | 0 | NH(CH₂)₂F |
| II-43 | Benzo | Benzo | bond | —CH₂— | 0 | 0 | NEt₂ |
| II-44 | Benzo | Benzo | bond | —CH₂— | 0 | 0 | NH—(R)—CH(CH₃)CONH₂ |
| II-45 | Benzo | Benzo | bond | —CH₂— | 0 | 0 | NH—(R)—CH(CH₃)—C₆H₅ |
| II-46 | Benzo | Benzo | bond | —CH₂— | 0 | 0 | NH—(S)—CH(CH₃)—CH₂OH |
| II-47 | Benzo | Benzo | bond | —CH₂— | 0 | 0 | NH—(S)—CH(CH₃)—CO₂Me |
| II-48 | Benzo | Benzo | bond | —CH₂— | 0 | 0 | NH—(S)—CH(CH₃)CONH₂ |
| II-49 | Benzo | Benzo | bond | —CH₂— | 0 | 0 | NH—(S)—CH(CH₃)CONH₂ |
| II-50 | Benzo | Benzo | bond | —CH₂— | 0 | 0 | NH—(S)—CH(CH₃)CONMe₂ |
| II-51 | Benzo | Benzo | bond | —CH₂— | 0 | 0 | NH—(S)—CH(CH₂OH)CONH₂ |
| II-52 | Benzo | Benzo | bond | —CH₂— | 0 | 0 | NH—(S)—CH[CH(OH)CH₃]CONH₂ |
| II-53 | Benzo | Benzo | bond | —CH₂— | 0 | 0 | 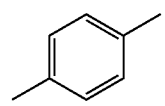 |
| II-54 | Benzo | Benzo | bond | —CH(CH₃)— | 0 | 0 | NH₂ |
| II-55 | Benzo | Benzo | —O— | —CH₂— | 1 | 0 | NH₂ |
| II-56 | Benzo | Benzo | —O— | —CH₂— | 0 | 0 | N(CH₃)₂ |
| II-57 | Benzo | Benzo | —O— | —CH₂— | 0 | 0 | NH—(S)—CH(CH₃)CONH₂ |
| II-58 | Benzo | Benzo | —CH₂CH₂— | —CH₂CH₂— | 0 | 0 | NH₂ |
| II-59 | Benzo | Benzo | —CH₂CH₂— | —CH(CH₃)— | 1 | 0 | NH₂ |
| II-60 | Benzo | Benzo | bond | 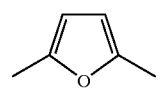 | 0 | 0 | NH₂ |
| II-61 | Benzo | Benzo | —CH=CH— | —C(CH₃)₂— | 1 | 0 | NH₂ |
| II-62 | Benzo | Benzo | —CH₂CH₂— | —CH₂— | 1 | 0 | NH—CH(CH₃)CONH₂ |
| II-63 | Benzo | Benzo | —CH₂CH₂— | —CH₂— | 1 | 0 | morpholino |
| II-64 | Benzo | Benzo | bond |  | 1 | 0 | NH₂ |
| II-65 | Benzo | Benzo | bond | —CH=CH— | 0 | 0 | NH₂ |

TABLE 2-continued (II-A)

| No. | A | B | X | Y | m | n | NR₃R₄ |
|---|---|---|---|---|---|---|---|
| II-66 | 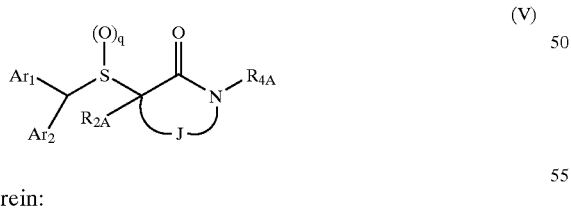 | Benzo | bond | —CH₂— | 0 | 0 | NH₂ |

For example, compounds II-1 and II-22 have the following structures:

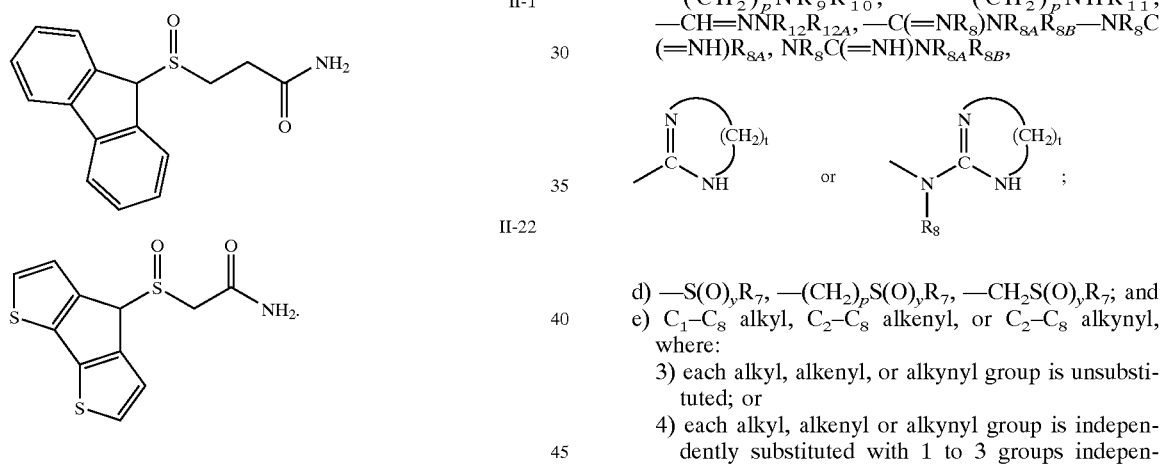

In additional embodiments of the present invention, there are provided compounds of formula (V):

(V)

wherein:
$Ar_1$ and $Ar_2$ are each independently selected from $C_6$–$C_{10}$ aryl or heteroaryl;
  wherein each of $Ar_1$ or $Ar_2$ may be independently optionally substituted with 1–3 substituents independently selected from:
  a) H, $C_6$–$C_{10}$ aryl, heteroaryl, F, Cl, Br, I, —CN, —CF₃, —NO₂, —OH, —OR₇, —O(CH₂)$_p$NR₉R₁₀, —OC(=O)R₇, —OC(=O)NR₉R₁₀, —O(CH₂)$_p$OR₈, —CH₂OR₈, —NR₉R₁₀, —NR₈S(=O)₂R₇, —NR₈C(=O)R₇, or —NR₈C(=S)R₇;
  b) —CH₂OR₁₁;
  c) —NR₈C(=O)NR₉R₁₀, —NR₈C(=S)NR₉R₁₀, —CO₂R₁₂, —C(=O)R₁₃, —C(=O)NR₉R₁₀, —C(=S)NR₉R₁₀, —CH=NOR₁₂, —CH=NR₇, —(CH₂)$_p$NR₉R₁₀, —(CH₂)$_p$NHR₁₁, —CH=NNR₁₂R₁₂A, —C(=NR₈)NR₈AR₈B—NR₈C(=NH)R₈A, NR₈C(=NH)NR₈AR₈B, d) —S(O)$_y$R₇, —(CH₂)$_p$S(O)$_y$R₇, —CH₂S(O)$_y$R₇; and
  e) $C_1$–$C_8$ alkyl, $C_2$–$C_8$ alkenyl, or $C_2$–$C_8$ alkynyl, where:
    3) each alkyl, alkenyl, or alkynyl group is unsubstituted; or
    4) each alkyl, alkenyl or alkynyl group is independently substituted with 1 to 3 groups independently selected from $C_6$–$C_{10}$ aryl, heteroaryl, F, Cl, Br, I, CF₃, —CN, —NO₂, —OH, —OR₇, —CH₂OR₈, —NR₉R₁₀, —O—(CH₂)$_p$—OH, —S—(CH₂)$_p$—OH, —X₁(CH₂)$_p$OR₇, X₁(CH₂)$_p$NR₉R₁₀, —X₁(CH₂)$_p$C(=O)NR₉R₁₀, —X₁(CH₂)$_p$C(=S)NR₉R₁₀, —X₁(CH₂)$_p$OC(=O)NR₉R₁₀, —X₁(CH₂)$_p$CO₂R₈, —X₁(CH₂)$_p$S(O)$_y$R₇, —X₁(CH₂)$_p$NR₈C(=O)NR₉R₁₀, —C(=O)R₁₃, —CO₂R₁₂, —OC(=O)R₇, —C(=O)NR₉R₁₀, —OC(=O)NR₁₂R₁₂A, O-tetrahydropyranyl, —C(=S)NR₉R₁₀, —CH=NNR₁₂R₁₂A, —CH=NOR₁₂, —CH=NR₇, —CH=NNHCH(N=NH)NH₂, —NR₈CO₂R₇, —NR₈C(=O)NR₉R₁₀, —NR₈C(=S)NR₉R₁₀, —NHC(=NH)NH₂, —NR₈C(=O)R₇, —NR₈C(=S)R₇, —NR₈S(=O)₂R₇, —S(O)$_y$R₇, —S(=O)₂NR₁₂R₁₂A, —P(=O)(OR₈)₂, —OR₁₁, and a $C_5$–$C_7$ monosaccharide where each hydroxyl group of the monosaccharide is independently either unsubstituted or is replaced by H, $C_1$–$C_4$ alkyl, $C_1$–$C_4$ alkoxy, or —O—C(=O)R₇;

$X_1$ is —O—, —S—, —N($R_8$)—;
J is $C_2$–$C_4$ alkylene or Q—CO—;
Q is $C_1$–$C_3$ alkylene;
$R_{2A}$ is H, $C_1$–$C_6$ alkyl, aryl or heteroaryl;
$R_{4A}$ is H, $C_1$–$C_6$ alkyl, aryl or heteroaryl;
$R_7$ is $C_1$–$C_6$ alkyl, $C_6$–$C_{10}$ aryl, or heteroaryl;
$R_8$, $R_{8A}$ and $R_{8B}$ are each independently H, $C_1$–$C_4$ alkyl, or $C_6$–$C_{10}$ aryl;
$R_9$ and $R_{10}$ are independently selected from H, $C_1$–$C_4$ alkyl, and $C_6$–$C_{10}$ aryl; or $R_9$ and $R_{10}$ together with the nitrogen to which they are attached, form a 3–7 member heterocyclic ring;
$R_{11}$ is the residue of an amino acid after the hydroxyl group of the carboxyl group is removed;
$R_{12}$ and $R_{12A}$ are each independently selected from H, $C_1$–$C_6$ alkyl, cycloalkyl, $C_6$–$C_{10}$ aryl, and heteroaryl; or $R_{12}$ and $R_{12A}$, together with the nitrogen to which they are attached, form a 5–7 member heterocyclic ring;
$R_{13}$ is H, $C_1$–$C_6$ alkyl, cycloalkyl, $C_6$–$C_{10}$ aryl, heteroaryl, —C(=O)$R_7$, —C(=O)NR$_9$R$_{10}$, or —C(=S)NR$_8$R$_{10}$;
p is from 1, 2, 3, or 4;
q is 0, 1, or 2;
t is 2, 3, or 4;
y is 0, 1 or 2;
and the stereoisomeric forms, mixtures of stereoisomeric forms, or pharmaceutically acceptable salt and ester forms thereof.

In particular embodiments of formula (V), $Ar_1$ and $Ar_2$ are each independently phenyl or thienyl, preferably both are phenyl; q is preferably 1; when J is $C_2$–$C_4$ alkylene, it is preferably $C_2$ alkylene or $C_3$ alkylene; $R_{2A}$ is preferably H, $C_1$–$C_6$ alkyl and $R_{4A}$ is preferably phenyl, thienyl or pyridyl, and more preferably, $R_{4A}$ is phenyl.

In another particular embodiment of formula (V), there are provided compounds where q is 1; and J is Q—CO to form a compound of formula (VI):

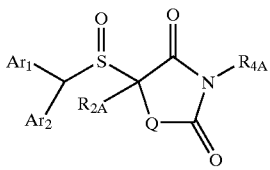

(VI)

wherein Q is $C_1$–$C_3$ alkylene. In certain embodiments, $Ar_1$ and $Ar_2$ are each independently phenyl or thienyl, preferably both are phenyl; and Q is C, alkylene or $C_2$ alkylene. Certain preferred embodiments of formula (VI) are provided in Table 2A:

TABLE 2A

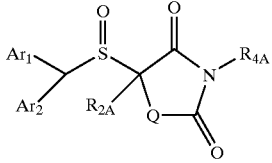

(VI)

| No. | $Ar_1$ | $Ar_2$ | $R_{2A}$ | Q | $R_{4A}$ |
|---|---|---|---|---|---|
| VI-1 | Phenyl | Phenyl | H | $CH_2$ | H |
| VI-2 | Phenyl | Phenyl | H | $CH_2$ | $CH_3$ |
| VI-3 | Phenyl | Phenyl | H | $CH_2$ | $(CH_2)_2$OMe |

TABLE 2A-continued

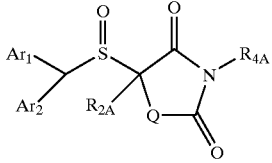

(VI)

| No. | $Ar_1$ | $Ar_2$ | $R_{2A}$ | Q | $R_{4A}$ |
|---|---|---|---|---|---|
| VI-4 | Phenyl | Phenyl | H | $CH_2$ | $(CH_2)_2$OH |
| VI-5 | Phenyl | Phenyl | H | $CH_2$ | (S)—CH(CH$_3$)CH$_2$OH |
| VI-6 | 4-Fluorophenyl | 4-Fluorophenyl | H | $CH_2$ | $CH_3$ |
| VI-7 | 3-Thienyl | 3-Thienyl | H | $CH_2$ | H |
| VI-8 | 3-Thienyl | Phenyl | H | $CH_2$ | H |
| VI-9 | Phenyl | Phenyl | H | $(CH_2)_2$ | H |

In additional embodiments of the present invention, there are provided compounds of formula (VII):

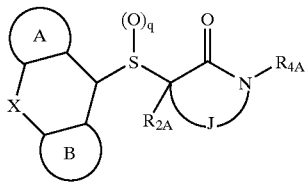

(VII)

wherein
X is a bond, —CH$_2$CH$_2$—, —O—, —S(O)$_y$—, —N(R$_8$)—, —CHN(R$_8$)—, —CH=CH—, —CH$_2$—CH=CH—, C(=O), —C(R$_8$)=N—, —N=C(R$_8$)—, —C(=O)—N(R$_8$)—, or —NR$_8$—C(=O)—;

Rings A and B, together with the carbon atoms to which they are attached, are each independently selected from:
a) a 6-membered aromatic carbocyclic ring in which from 1 to 3 carbon atoms may be replaced by hetero atoms selected from oxygen, nitrogen and sulfur; and
b) a 5-membered aromatic carbocyclic ring in which either:
  i) one carbon atom is replaced with an oxygen, nitrogen, or sulfur atom;
  ii) two carbon atoms are replaced with a sulfur and a nitrogen atom, an oxygen and a nitrogen atom, or two nitrogen atoms; or
  iii) three carbon atoms are replaced with three nitrogen atoms, one oxygen and two nitrogen atoms, or one sulfur and two nitrogen atoms;

wherein Ring A and Ring B may each independently be substituted with 1–3 substituents selected from:
a) H, $C_6$–$C_{10}$ aryl, heteroaryl, F, Cl, Br, I, —CN, —CF$_3$, —NO$_2$, —OH, —OR$_7$, —O(CH$_2$)$_p$NR$_9$R$_{10}$, —OC(=O)R$_7$, —OC(=O)NR$_9$R$_{10}$, —O(CH$_2$)$_p$OR$_8$, —CH$_2$OR$_8$, —NR$_9$R$_{10}$, —NR$_8$S(=O)$_2$R$_7$, —NR$_8$C(=O)R$_7$, or —NR$_8$C(=S)R$_7$;
b) —CH$_2$OR$_{11}$;
c) —NR$_8$C(=O)NR$_9$R$_{10}$, —NR$_8$C(=S)NR$_9$R$_{10}$, —CO$_2$R$_{12}$, —C(=O)R$_{13}$, —C(=O)NR$_9$R$_{10}$, —C(=S)NR$_9$R$_{10}$, —CH=NOR$_{12}$, —CH=NR$_7$, —(CH$_2$)$_p$NR$_9$R$_{10}$, —(CH$_2$)$_p$NHR$_{11}$, —CH=NNR$_{12}$R$_{12A}$, —C(=NR$_8$)NR$_{8A}$R$_{8B}$—NR$_8$C(=NH)R$_{8A}$, —NR$_8$C(=NH)NR$_{8A}$R$_{8B}$,

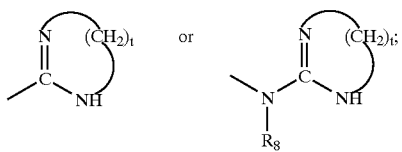

d) —S(O)$_y$R$_7$, —(CH$_2$)$_p$S(O)$_y$R$_7$, —CH$_2$S(O)$_y$R$_7$; and
e) C$_1$–C$_8$ alkyl, C$_2$–C$_8$ alkenyl, or C$_2$–C$_8$ alkynyl, where:
  1) each alkyl, alkenyl, or alkynyl group is unsubstituted; or
  2) each alkyl, alkenyl or alkynyl group is independently substituted with 1 to 3 groups independently selected from C$_6$–C$_{10}$ aryl, heteroaryl, F, Cl, Br, I, CF$_3$, —CN, —NO$_2$, —OH, —OR$_7$, —CH$_2$OR$_8$, —NR$_9$R$_{10}$, —O—(CH$_2$)$_p$—OH, —S—(CH$_2$)$_p$—OH, —X$_1$(CH$_2$)$_p$OR$_7$, X$_1$(CH$_2$)$_p$NR$_9$R$_{10}$, —X$_1$(CH$_2$)$_p$C(=O)NR$_9$R$_{10}$, —X$_1$(CH$_2$)$_p$C(=S)NR$_9$R$_{10}$, —X$_1$(CH$_2$)$_p$OC(=O)NR$_9$R$_{10}$, —X, (CH$_2$)$_p$CO$_2$R$_8$, —X$_1$(CH$_2$)$_p$S(O)$_y$R$_7$, —X$_1$(CH$_2$)$_p$NR$_8$C(=O)NR$_9$R$_{10}$, —C(=O)R$_{13}$, —CO$_2$R$_{12}$, —OC(=O)R$_7$, —C(=O)NR$_9$R$_{10}$, —OC(=O)NR$_{12}$R$_{12A}$, O-tetrahydropyranyl, —C(=S)NR$_9$R$_{10}$, —CH=NNR$_{12}$R$_{12A}$, —CH=NOR$_{12}$, —CH=NR$_7$, —CH=NNHCH(N=NH)NH$_2$, —NR$_8$CO$_2$R$_7$, —NR$_8$C(=O)NR$_9$R$_{10}$, —NR$_8$C(=S)NR$_9$R$_{10}$, —NHC(=NH)NH$_2$, —NR$_8$C(=O)R$_7$, —NR$_8$C(=S)R$_7$, —NR$_8$S(=O)$_2$R$_7$, —S(O)$_y$R$_7$, —S(=O)$_2$NR$_{12}$R$_{12A}$, —P(=O)(OR$_8$)$_2$, —OR$_{11}$, and a C$_5$–C$_7$ monosaccharide where each hydroxyl group of the monosaccharide is independently either unsubstituted or is replaced by H, C$_1$–C$_4$ alkyl, C$_1$–C$_4$ alkoxy, or —O—C(=O)R$_7$;

J is C$_2$–C$_4$ alkylene or Q—CO—;
Q is C$_1$–C$_3$ alkylene;
R$_{2A}$ is H, C$_1$–C$_6$ alkyl, aryl or heteroaryl;
R$_{4A}$ is H, C$_1$–C$_6$ alkyl, aryl or heteroaryl;
R$_7$ is C$_1$–C$_6$ alkyl, C$_6$–C$_{10}$ aryl, or heteroaryl;
R$_8$, R$_{8A}$ and R$_{8B}$ are each independently H, C$_1$–C$_4$ alkyl, or C$_6$–C$_{10}$ aryl;
R$_9$ and R$_{10}$ are independently selected from H, C$_1$–C$_4$ alkyl, and C$_6$–C$_{10}$ aryl; or R$_9$ and R$_{10}$ together with the nitrogen to which they are attached, form a 3–7 member heterocyclic ring;
R$_{11}$ is the residue of an amino acid after the hydroxyl group of the carboxyl group is removed;
R$_{12}$ and R$_{12A}$ are each independently selected from H, C$_1$–C$_6$ alkyl, cycloalkyl, C$_6$–C$_{10}$ aryl, and heteroaryl; or R$_{12}$ and R$_{12A}$, together with the nitrogen to which they are attached, form a 5–7 member heterocyclic ring;
R$_{13}$ is H, C$_1$–C$_6$ alkyl, cycloalkyl, C$_6$–C$_{10}$ aryl, heteroaryl, —C(=O)R$_7$, —C(=O)NR$_9$R$_{10}$, or —C(=S)NR$_9$R$_{10}$;
X$_1$ is —O—, —S—, —N(R)—;
p is from 1 to 4;
q is 0, 1, or 2;
t is 2, 3, or 4;
y is 0, 1 or 2;
and the stereoisomeric forms, mixtures of stereoisomeric forms, or pharmaceutically acceptable salt and ester forms thereof.

In particular embodiments of formula (VII), rings A and B are each independently benzo or thieno, preferably both are benzo; q is preferably 1; when J is C$_2$–C$_4$ alkylene, it is preferably C$_2$ alkylene or C$_3$ alkylene; R$_{2A}$ is preferably H, C$_1$–C$_6$ alkyl and R$_{4A}$ is preferably phenyl, thienyl or pyridyl, and more preferably, R$_{4A}$ is phenyl. A preferred embodiment is a compound of formula (VII-1):

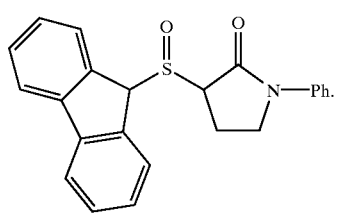

(VII-1)

In another particular embodiment of formula (VII), there are provided compounds where q is 1; and J is Q—CO— to form a compound of formula (VIII):

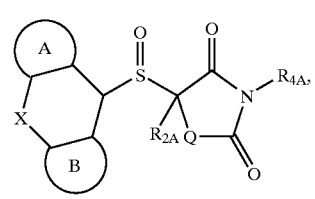

(VII)

wherein Q is C$_1$–C$_3$ alkylene. In certain embodiments, rings A and B are both preferably benzo; X is preferably a bond or —O—; and Q is Cl alkylene or C$_2$ alkylene. Certain preferred embodiments of formula (VIII) are provided in Table 2B:

TABLE 2B (VIII)

| No. | A | B | X | R$_{2A}$ | Q | R$_{4A}$ |
|---|---|---|---|---|---|---|
| VIII-1 | Benzo | Benzo | bond | H | CH$_2$ | H |
| VIII-2 | Benzo | Benzo | bond | H | CH$_2$ | Me |
| VIII-3 | Benzo | Benzo | bond | H | CH$_2$ | (CH$_2$)$_2$OMe |
| VIII-4 | Benzo | Benzo | bond | H | CH$_2$ | (CH$_2$)$_2$OH |
| VIII-5 | Benzo | Benzo | bond | H | CH$_2$ | CH(CH$_3$)CH$_2$OH |
| VIII-6 | Benzo | Benzo | bond | H | CH$_2$ | OH |
| VIII-7 | Benzo | Benzo | bond | H | CH$_2$ | CH$_2$-(4-methoxyphenyl) |
| VIII-8 | Benzo | Benzo | bond | H | CH$_2$ | Ph |
| VIII-9 | Benzo | Benzo | bond | H | (CH$_2$)$_2$ | H |

Definitions

As used herein, the term "alkyl" refers to a substituted or unsubstituted, branched or straight hydrocarbon chain of 1 to 8 carbon atoms, which is formed by the removal of one hydrogen atom. In certain preferred embodiments, the alkyl group contains from 1 to 6 carbon atoms. In other preferred embodiments, the alkyl group contains from 1 to 4 carbon atoms. A designation such as "$C_1$–$C_4$ alkyl" refers to an alkyl radical containing from 1 to 4 carbon atoms. Examples include methyl, ethyl, n-propyl, isopropyl, n-butyl, isobutyl, sec-butyl, t-butyl, pentyl, 2-methylpentyl, hexyl, 2-methylhexyl, 2,3-dimethylhexyl, heptyl, octyl, etc.

As used herein, the term "lower alkyl," refers to a $C_1$ to $C_6$ saturated straight chain, branched, or cyclic hydrocarbon, which are optionally substituted. Lower alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl and the like.

As used herein, "alkenyl" refers to a substituted or unsubstituted, straight or branched hydrocarbon chain containing from 2 to 8 carbon atoms having one or more carbon—carbon double bonds which may occur in any stable point along the chain, and which is formed by removal of one hydrogen atom. A designation "$C_2$–$C_8$ alkenyl" refers to an alkenyl radical containing from 2 to 8 carbon atoms. Examples include ethenyl, propenyl, isopropenyl, 2,4-pentadienyl, etc.

As used herein, "alkynyl" refers to a substituted or unsubstituted, straight or branched hydrocarbon radical containing from 2 to 8 carbon atoms, having one or more carbon—carbon triple bonds which may occur in any stable point along the chain, and which is formed by removal of one hydrogen atom. A designation "$C_2$-Cg alkynyl" refers to an alkynyl radical containing from 2 to 8 carbon atoms. Examples include ethynyl, propynyl, isopropynyl, 3,5-hexadiynyl, etc.

As used herein, "carbocycle" or "carbocyclic" refer to a substituted or unsubstituted, stable monocyclic or bicyclic hydrocarbon ring which is saturated, partially unsaturated or unsaturated, and contains from 3 to 10 carbon atoms. Accordingly the carbocyclic group may be aromatic or non-aromatic. The bonds connecting the endocyclic carbon atoms of a carbocyclic group may be single, double, triple, or part of a fused aromatic moiety. Carbocycles are intended to include the "cycloalkyl" and "aryl" compounds defined herein.

As used herein, the term "cycloalkyl" refers to a substituted or unsubstituted hydrocarbon ring of 3 to 7 carbon atoms formed by the removal of one hydrogen atom. A designation such as "$C_5$–$C_7$ cycloalkyl" refers to a cycloalkyl radical containing from 5 to 7 carbon atoms. Examples include cyclopropyl, cyclopentyl, cyclohexyl, cycloheptyl, etc.

As used herein, the terms "heterocycle" or "heterocyclic" refer to a substituted or unsubstituted, saturated, partially unsaturated or unsaturated, stable 3 to 10 membered monocyclic or bicyclic ring wherein at least one member of the ring is a hetero atom. Accordingly the heterocyclic group may be aromatic or non-aromatic. Typically, heteroatoms include, but are not limited to, oxygen, nitrogen, sulfur, selenium, and phosphorus atoms. Preferable heteroatoms are oxygen, nitrogen and sulfur. The nitrogen and sulfur heteroatoms may be optionally oxidized, and the nitrogen may be optionally substituted in non-aromatic rings. The bonds connecting the endocyclic atoms of a heterocyclic group may be single, double, triple, or part of a fused aromatic moiety. Heterocycles are intended to include "heterocyclyl" and "heteroaryl" compounds defined herein.

As used herein, "heterocyclyl" refers to a substituted or unsubstituted, saturated, or partially unsaturated, stable 3 to 7 membered heterocyclic ring which is formed by removal of one hydrogen atom. Examples include epoxyethyl, pyrrolidyl, pyrazolidinyl, piperidyl, pyranyl, oxazolinyl, morpholino, morpholinyl, piperazinyl, etc.

Examples of heterocycles include, but are not limited to, 2-pyrrolidinyl, 2H-pyrrolyl, 4-piperidinyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl, and tetrazole. Suitable heterocycles are also disclosed in *The Handbook of Chemistry and Physics*, 76th Edition, CRC Press, Inc., 1995–1996, pages 2–25 to 2–26, the disclosure of which is hereby incorporated by reference.

Preferred heterocyclic groups formed with a nitrogen atom include, but are not limited to, pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups.

Preferred heterocyclic groups formed with an oxygen atom include, but are not limited to, furan, tetrahydrofuran, pyran, benzofurans, isobenzofurans, and tetrahydropyran groups. Preferred heterocyclic groups formed with a sulfur atom include, but are not limited to, thiophene, thianaphthene, tetrahydrothiophene, tetrahydrothiapyran, and benzothiophenes.

Preferred aromatic heterocyclic groups include, but are not limited to, pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups.

As used herein, the term "substituted" refers to replacement of one or more hydrogen atoms on an indicated group with a selected group referred to herein as a "substituent", provided that the substituted atom's valency is not exceeded, and that the substitution results in a stable compound. A substituted group has 1 to 5, preferably 1 to 3, and more preferably 1, independently selected substituents. Preferred substituents include, but are not limited to F, Cl, Br, I, OH, OR, $NH_2$, $NR_2$, NHOH, $NO_2$, CN, $CF_3$, $CF_2CF_3$, $C_1$–$C_6$ alkyl, $C_2$–$C_6$ alkenyl, $C_2$–$C_6$ alkynyl, $C_1$–$C_6$ alkoxy, $C_3$–$C_7$ cycloalkyl, heterocyclyl, $C_6$–$C_{10}$ aryl, heteroaryl, arylalkyl, C(=O)R, COOH, $CO_2$R, O—C(=O)R, C(=O)NRR', NRC(=O)R', $NRCO_2$R', OC(=O)NRR', —NRC(=O) NRR', —NRC(=S)NRR', and —$SO_2$NRR', wherein R and R' are each independently hydrogen, $C_1$–$C_6$ alkyl, or $C_6$–$C_{10}$ aryl.

As used herein, the term "aryl" refers to a substituted or unsubstituted, aromatic carbocyclic ring containing from 6 to 10 carbon atoms, which is formed by removal of one hydrogen atom. Examples include phenyl, naphthyl, indenyl, etc.

As used herein, the term "heteroaryl" refers to a substituted or unsubstituted 5 to 10 membered aromatic heterocyclic ring, which is formed by removal of one hydrogen atom. Examples include pyrrolyl, pyridyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, etc.

As used herein, the term "alkylene" refers to a substituted or unsubstituted, branched or straight chained hydrocarbon of 1 to 8 carbon atoms, which is formed by the removal of two hydrogen atoms. A designation such as "$C_1$–$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "cycloalkylene" refers to substituted or unsubstituted carbocyclic ring of 3 to 8 carbon atoms, which is formed by removal of two hydrogen atoms. A designation such as "$C_3$–$C_8$ cycloalkylene" refers to an cycloalkylene radical containing from 3 to 8 carbon atoms. Examples include cyclopropylene (—$C_3H_4$—), cyclopentylene (—$C_5H_8$—), cyclohexylene (—$C_6H_{10}$—), etc.

As used herein, the term "heterocyclylene" refers to a substituted or unsubstituted, saturated, or partially unsaturated, stable 3 to 7 membered heterocyclic ring, which is formed by removal of two hydrogen atoms. Examples include epoxyethylene, pyrrolidylene, pyrrolidylidene, pyrazolidinylene, piperidylene, pyranylene, morpholinylidene, etc.

As used herein, the term "arylene" refers to a substituted or unsubstituted aromatic carbocyclic ring containing from 6 to 10 carbon atoms, which is formed by removal of two hydrogen atoms. Examples include phenylene (—$C_6H_4$—), naphthylene (—$C_{10}H_6$—), etc. The "phenylene" group has the following structure:

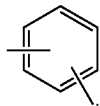

As used herein, the term "heteroarylene" refers to a substituted or unsubstituted 5 to 10 membered aromatic heterocyclic ring formed by removal of two hydrogen atoms. Examples include the heteroarylene groups which correspond to the respective heteroaryl compounds described above, and in particular, include thienylene (—$C_4H_2S$—), pyridylene (—$C_5H_3N$—), pyrimidinylene (—$C_3H_2N_2$—), quinolinylene (—$C_9H_5N$—), thiazolylene (—$C_3HNS$—), etc. The "thienylene" group has the following structure:

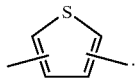

The "pyridylene" group has the following structure:

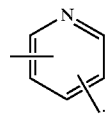

As used herein, the term "alkoxy" refers to an oxygen radical substituted with an alkyl group. Preferably, the alkoxy group contains from 1 to 6 carbon atoms. A designation such as "$C_1$–$C_4$ alkoxy" refers to an alkoxy containing from 1 to 4 carbon atoms. Examples include methoxy, ethoxy, n-propoxy, isopropoxy, n-butoxy, isobutoxy, sec-butoxy, t-butoxy, etc.

As used herein, the term "arylalkyl" refers to an aryl-substituted alkyl group and includes benzyl, bromobenzyl, diphenylmethyl, triphenylmethyl, phenylethyl, diphenylethyl, etc.

As used herein, "$C_5$–$C_7$ monosaccharide" refers to simple sugars of the formula $(CH_2O)_n$ wherein n=5–7. The monosaccharides can be straight-chain or ring systems, and can include a saccharose unit of the formula —CH(OH)—C(=O)—. Examples include erythrose, threose, ribose, arabinose, xylose, lyxose, allose, altrose, glucose, mannose, gulose, idose, galactose, talose, erythulose, ribulose, xyulose, psicose, fructose, sorbose, tagatose, erythropentulose, threopentulose, glycerotetrulose, glucopyranose, fructofuranose, etc.

As used herein, the term "amino acid" refers to a molecule containing both an amino group and a carboxyl group. Embodiments of amino acids include α-amino, β-amino, γ-amino acids. The α-amino acids have a general formula HOOC—CH(side chain)-$NH_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as (3-alanine, γ-aminobutyric acid, homocysteine, etc.), rare (such as 4-hydroxyproline, 5-hydroxylysine, 3-methylhistidine, etc.) and non-protein (such as citrulline, ornithine, canavanine, etc.) amino acids. Non-naturally occurring amino acids are well-known in the art, and include analogs of natural amino acids. See Lehninger, A. L. *Biochemistry*, $2^{nd}$ ed.; Worth Publishers: New York, 1975; 71–77, the disclosure of which is incorporated herein by reference. Non-naturally occurring amino acids also include α-amino acids wherein the side chains are replaced with synthetic derivatives. Representative side chains of naturally occurring and non-naturally occurring α-amino acids are shown below in Table A.

TABLE A

| | |
|---|---|
| $CH_3$— | HS—$CH_2$— |
| HO—$CH_2$— | $HO_2C$—CH($NH_2$)—$CH_2$—S—S—$CH_2$— |
| $C_6H_5$—$CH_2$— | $CH_3$—$CH_2$— |
| HO—$C_6H_4$—$CH_2$— | $CH_3$—S—$CH_2$—$CH_2$— |

TABLE A-continued

| | |
|---|---|
| 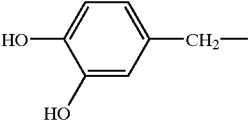 | $CH_3$—$CH_2$—S—$CH_2$—$CH_2$—<br>HO—$CH_2$—$CH_2$— |
| 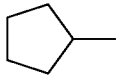 | |
| 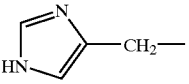 | $CH_3$—CH(OH)—<br>$HO_2C$—$CH_2$—NHC(=O)—$CH_2$—<br><br>$HO_2C$—$CH_2$—$CH_2$—<br>$NH_2C$(=O)—$CH_2$—$CH_2$— |
| 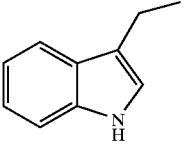 | $(CH_3)_2$—CH—<br>$(CH_3)_2$—CH—$CH_2$—<br>$CH_3$—$CH_2$—$CH_2$— |
| 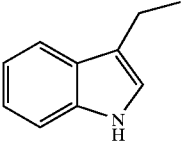 | $H_2N$—$CH_2$—$CH_2$—$CH_2$—<br>$H_2N$—C(=NH)—NH—$CH_2$—$CH_2$—$CH_2$—<br>$H_2N$—C(=O)—NH—$CH_2$—$CH_2$—$CH_2$— |
| 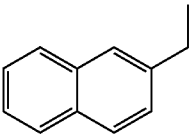 | $CH_3$—$CH_2$—CH($CH_3$)—<br>$CH_3$—$CH_2$—$CH_2$—$CH_2$—<br>$H_2N$—$CH_2$—$CH_2$—$CH_2$—$CH_2$— |

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, sulfuric, sulfamic, phosphoric, nitric and the like; and the salts prepared from organic acids such as acetic, propionic, succinic, tartaric, citric, glutamic, benzoic, salicylic, toluenesulfonic, oxalic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference.

As used herein, "prodrug" is intended to include any covalently bonded carriers which release the active parent drug according to the compounds of the present invention in vivo when such prodrug is administered to a mammalian subject. Since prodrugs are known to enhance numerous desirable qualities of pharmaceuticals (e.g., solubility, bioavailability, manufacturing, etc.), the compounds of the present invention may be delivered in prodrug form. Thus, the present invention contemplates prodrugs of the claimed compounds, compositions containing the same, and methods of delivering the same. Prodrugs of a compound of the present invention may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, cycloalkyl, aryl, and alkylaryl esters such as methyl, ethyl, cyclopropyl, phenyl, benzyl, and phenethyl esters, etc.

The present invention provides a method of treating diseases and conditions in a subject in need thereof comprising administering to said subject a therapeutically effective amount of a compound of formula (I), (I-A), (II), or (II-A). For example, the compounds of formula (I), (I-A), (II), or (II-A) can be used in the treatment of sleepiness, preferably sleepiness associated with narcolepsy, promotion of wakefulness, treatment of Parkinson's disease, cerebral ischemia, stroke, sleep apneas, eating disorders, preferably eating disorders associated with a disease, in particular, wherein the disease is anorexia nervosa, stimulation of appetite and weight gain, treatment of attention deficit hyperactivity disorder, enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), (I-A), (II), or (II-A) which is required to achieve the desired biological effect will vary depending upon a number of factors, including the dosage of the drug to be administered, the chemical characteristics (e.g., hydrophobicity) of the compounds employed, the potency of the compounds, the type of disease, the diseased state of the patient, and the route of administration. In general terms, the compounds of this invention may be provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. A preferred daily dose for adult humans includes about 25, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from about 0.1 to 100 mg/kg of body weight. By way of general guidance, unit doses for humans range from about 0.1 mg to about 1000 mg per day. Preferably the unit dose range is from about 1 to about 500 mg administered one to four times a day, and even more preferably from about 10 mg to about 300 mg, two times a day. In an alternate method of describing an effective dose, a preferred oral unit dose is one that is necessary to achieve a blood serum level of about 0.05 to 20 $\mu$g/ml, and more preferably, of about 1 to about 20 $\mu$g/ml in a subject.

Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches.

The compositions may conveniently be administered in unit dosage form and may be prepared by any of the methods well known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000. Pharmaceutically compatible binding agents, and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrants such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or nonaqueous solutions, suspensions, and emulsions. The liquid compositions may also include binders, buffers, preservatives, chelating agents, sweetening, flavoring and coloring agents, and the like. Nonaqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The compounds of the current invention can be employed as the sole active ingredient in a pharmaceutical composition. Alternatively, they can be used in combination or combined with other pharmaceutical agents associated with other disease states. In particular, the compounds of formula (I), (I-A), (II), or (II-A) can be combined with agents that are useful for the treatment of impaired cognition associated with various disease states including, but not limited to, age, trauma, stress or transient impairment due to chemical imbalance or toxicity, hypersomnia, depression, Alzheimer's Disease, non-Alzheimer's dementias, including Lewy body dementia, vascular dementia and Binswanger's dementia, schizophrenia, and the like. The present invention would encompass, therefore, combinations of the compounds of the current invention with eburnane analogs, heterocyclic inducers of tyrosine hydroxylase, 3,4-diphenyl chromans, tacrine metabolites, aza-cyclic compounds, polyamine compounds, or thiamine; nonanticholinergic antidepressants such as benzodiazepines; phenothiazines aliphatic such as chlorpromazine; piperidines such as thioridazine; piperazines such as trifluoperazine, fluphenazine and perphenazine; dibenzoxazepines such as loxapine; dihydroindolones such as molindone; thioxanthenes such as thiothixene; butyrophenones such as haloperidol; diphenylbutyl-piperidines such as pimozide; dibenzodiazepine such as clozapine; benzisoxazole such as risperidone; thienobenzodiazepine such as olanzapine; dibenzothiazepine such as quetiapine; imidazolidinone such as sertindole, benzisothiazolyl-piperazine such as ziprasidone, and the like.

Synthesis

The compounds of the present invention may be prepared in a number of ways well known to those skilled in the art. The compounds can be synthesized, for example, by the methods described below, or variations thereon as appreciated by the skilled artisan. The appropriate modifications and substitutions being readily apparent and well known or readily obtainable from the scientific literature to those skilled in the art.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present on the compounds of the present invention may contain protecting groups during the course of synthesis. For example, the amino acid side chain substituents of the compounds of formula (I), (I-A), (II), or (II-A) can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl ("Cbz") group, the tert-butyloxycarbonyl ("Boc") group, and the tosyl (p-toluensulfonyl, "Tos") group. Other preferred protecting groups according to the invention may be found in Greene, T. W. and Wuts, P. G. M., *Protective Groups in Organic Synthesis* 2d. Ed., Wiley & Sons, 1991.

Compounds of the present invention may be prepared as outlined in the following schemes. The reagents and starting materials are commercially available, or readily synthesized by well-known techniques by one of ordinary skill in the arts. All substituents, unless otherwise indicated, are as previously defined.

A general synthetic procedure is set forth in Scheme A for preparing the compounds of formula (I) [wherein Y=C($R_1$)($R_2$) and m, n=0] or (I-A):

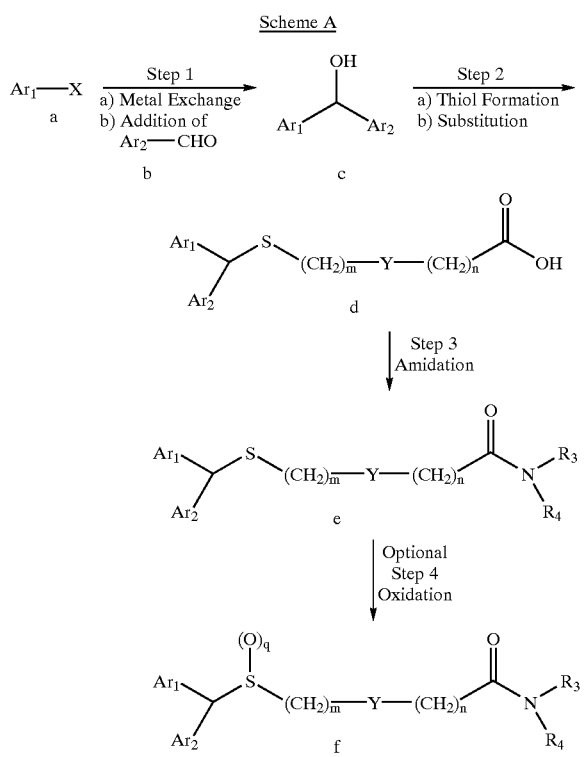

Scheme A

Scheme A, Step 1: Synthesis of Compounds of General Structure c:

In step 1a, the appropriate aryl halide a undergoes a metal exchange reaction with an organometallic compound to give the corresponding metalloaryl compound. For example, an appropriate haloaromatic or haloheteroaromatic (compound a) is reacted with an appropriate alkyl lithium compound in an aprotic solvent at a temperature −78° C. An appropriate haloaromatic or haloheteroaromatic compound is one where $Ar_1$ is as defined in the final product. An appropriate alkyl lithium compound is one that effects a metal-halogen exchange.

In step 1b, an appropriate aryl aldehyde b is added to the previously formed metalloaryl compound to give desired di-aryl alcohol c. For example, an appropriate aromatic aldehyde or heteroaromatic aldehyde (compound b) in an aprotic solvent is added to reaction product of step 1a. An appropriate heteroaromatic aldehyde is one where $Ar_2$ is as defined in the final product. Upon completion, the reaction mixture is quenched by an appropriate quenching agent and the product, compound c, is isolated by conventional methods commonly employed by those skilled in the art.

For example, a cooled (−70° C. to −78° C.) solution of an appropriate haloaromatic or haloheteroaromatic (compound a) in dry ether is reacted with n-butyllithium (1.1 eqv). After stirring for an additional period of time to allow the completion of halogen-metal exchange reaction, the next reactant, an appropriate heteroaromatic aldehyde (compound b) in ether is slowly be added to the reaction flask. Stirring is continued for an additional 2–3 h at the low temperature. The cooling bath is removed and the reaction mixture is slowly allowed to come to ambient temperature, followed by quenching, preferably by a saturated $NH_4Cl$ solution. The mixture is extracted into an organic solvent (ether or ethyl acetate). The organic layer is washed with brine, dried ($MgSO_4$ or $Na_2SO_4$) and concentrated to give a crude product. Purification is achieved by employing known purification techniques (preferably by column chromatography and/or recrystallization) to provide pure compounds c. The method is an adaptation from a procedure previously described by Gronowitz, S.; Eriksson, B. *Arkiv Kemi* 1963, 335, incorporated herein by reference in its entirety. Alternatively, this class of compounds wherein $Ar_1$ is the same as $Ar_2$ may be generated by treatment of two equivalents of an appropriate haloheteroaromatic with two equivalents of n-butyllithium, followed by one equivalent of ethyl formate as described by Nenajdenko, V. G.; Baraznenok, I. L.; Balenkova, E. S. *J. Org. Chem.* 1998, 6132, incorporated herein by reference in its entirety.

Scheme A, Step 2: Synthesis of Compounds of General Structure d:

In step 2a, the alcohol moiety of compound c is converted to the corresponding thiol. The thiol, in step 2b, undergoes a substitution reaction with an appropriate halogen-substituted alkylcarboxylic acid of structure Br-$(CH_2)_m$—Y—$(CH_2)_n$, —COOH, to generate compound d. For example, di-aryl alcohol c is reacted with thiourea in presence of an acid to convert it to a thiouronium moiety that is subsequently hydrolyzed in the presence of an alkaline base and reacted with the appropriate halogen-substituted alkylcarboxylic acid to generate compound d (step 2b). An appropriate acid derivative is one in which m, n, Y are as defined in the final product.

For example, in step 2a, an appropriate amount of thiourea is taken into 48% HBr and water. The mixture is warmed (preferably to 60–70° C.), followed by addition of compound c. The temperature of the reaction mixture is elevated (preferably to 90–95° C.) and the stirring is continued for an additional period of time for completion of the reaction. The reaction mixture is cooled to room temperature (in some cases, an ice-bath might be needed) and the precipitated solid should be filtered and thoroughly washed with water.

In step 2b, the wet solid from the previous step is taken into additional water and treated with an aqueous base, preferably sodium hydroxide solution. The mixture is warmed (preferably to 70–80° C., but in some cases a higher temperature might be needed) and to it an appropriate amount of halogen-substituted alkylcarboxylic acid derivative in water (or in some cases, an alcoholic solvent) is added. The reaction mixture is maintained at an elevated temperature (preferably 100–110° C.) for an appropriate period of time, cooled, taken into water and washed with an organic solvent (preferably ether). The basic aqueous layer is acidified with an inorganic acid solution (e.g. aqueous HCl solution). The aqueous (acidic) solution is then extracted several times into an organic solvent (e.g. ether or ethyl acetate). The combined organic layer is washed with brine, dried ($MgSO_4$ or $Na_2SO_4$) and concentrated to give the crude product that may be used directly in the next step. However, purification could be achieved by employing known purification techniques (e.g. recrystallization) to provide pure compound d.

The method is an adaptation from a procedure previously described in U.S. Pat. No. 4,177,290, incorporated by reference herein in its entirety.

Scheme A, Step 3: Synthesis of Compounds of General Structure e:

In step 3a, the carboxylic acid is converted into appropriate acid derivative, which is then reacted with an appropriate amine to give compound e. For example in step 3a, compound d can be converted to the corresponding acid chloride, or the corresponding activated ester. The acid chloride can be obtained by reacting compound d with thionyl chloride in an aromatic hydrocarbon solvent in refluxing condition. Alternatively, the activated ester can be obtained by use of various agents known in the art, such as 2-(1H-Benzotriazol-1-yl)-1,1,3,3-tetramethyluronium tetrafluoroborate ("TBTU"), N-methylmorpholine ("NMM") and dimethyl formamide ("DMF"). In step 3b, the product of step 3a is reacted with an appropriate amine of structure $NHR_3R_4$ to give the desired compound e. An appropriate amine is one which correlates to $R_3$ and $R_4$ as defined in the final product.

For example, a solution of an appropriate carboxylic acid (compound d) in either benzene or toluene is brought to reflux temperature and to it is slowly added an appropriate amount of thionyl chloride. The mixture is refluxed until the disappearance of starting material (as evidenced by analytical techniques), cooled and solvent removed. The resulting residue is taken into an appropriate organic solvent (preferably tetrahydrofuran or methylene chloride) and treated with ammonia gas (or 28% aqueous ammonia hydroxide solution) or an appropriate amine. The reaction mixture is then partitioned between water and an organic solvent (preferably ethyl acetate). The separated organic layer is washed with water, dilute acid, dilute base and brine, dried over a drying agent (e.g. $MgSO_4$ or $Na_2SO_4$) and concentrated to give the crude product that may be purified by column chromatography and/or recrystallization to produce compound e.

Scheme A, Optional Step 4: Synthesis of Compounds of General Structure f:

Compounds of structure e may optionally be oxidized to generate compounds of structure f. Thus, compound f is prepared by reacting compound e in an appropriate solvent with an appropriate oxidizing agent. An appropriate oxidizing agent is one that oxidizes the sulfide group of compound e. The corresponding product is isolated and purified by methods well known in the art.

For example, to a cooled (−15° C. to −25° C.) solution of compound e in an organic solvent (preferably methylene chloride or chloroform), an appropriate oxidizing agent (e.g. m-chloroperoxybenzoic acid ["m-CPBA"], 1 equivalent) in the same solvent is slowly added. Stirring is continued at low temperature until the disappearance of the starting material, as evidenced by various analytical techniques. The reaction mixture is then thoroughly washed with a saturated sodium bicarbonate solution, water and brine, respectively, dried over a drying agent (e.g. $MgSO_4$ or $Na_2SO_4$) and concentrated. The desired product (compound f) is purified, if needed, by employing known purification techniques (preferably by column chromatography and/or recrystallization). In some cases, the oxidation is performed by employing 50% $H_2O_2$ in glacial acetic acid solvent.

A general synthetic procedure is set forth in Scheme B for preparing the compounds of formula (II) [wherein ring A is phenylene; $Y=C(R_1)(R_2)$ and m, n=0] and (II-A):

Scheme B

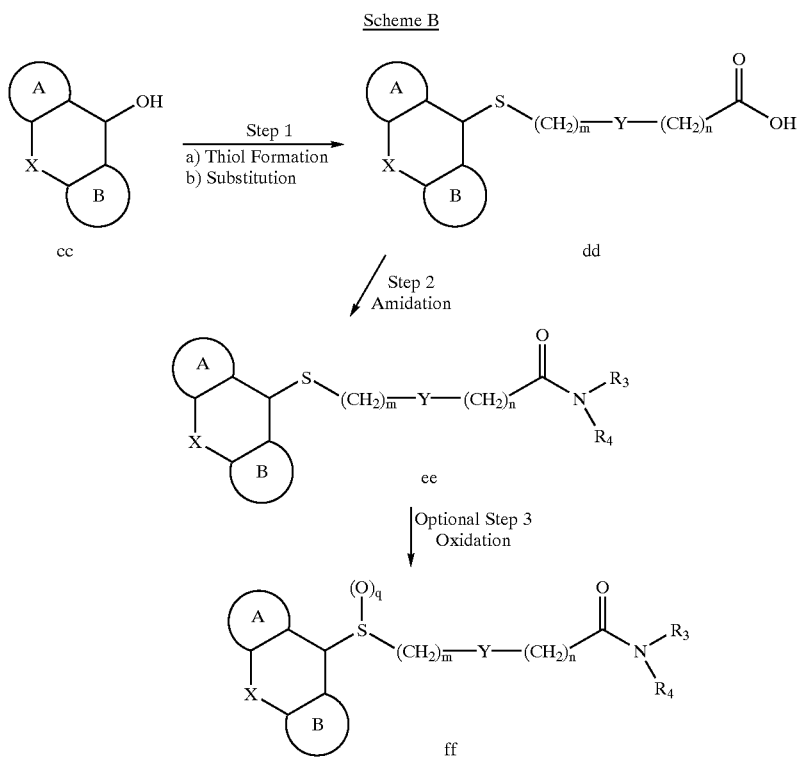

Scheme B, Steps 1, 2, and 3: Synthesis of Compounds of General Structure dd, ee and ff.

The synthetic steps in Scheme B involve the same multistep general method described in Scheme A, wherein Scheme B, steps 1–3 corresponds to Scheme A, steps 2–4, respectively.

A general synthetic procedure is set forth in Scheme C for preparing the compounds of formula (I-A), wherein n=0 and Y is

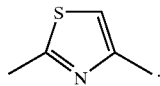

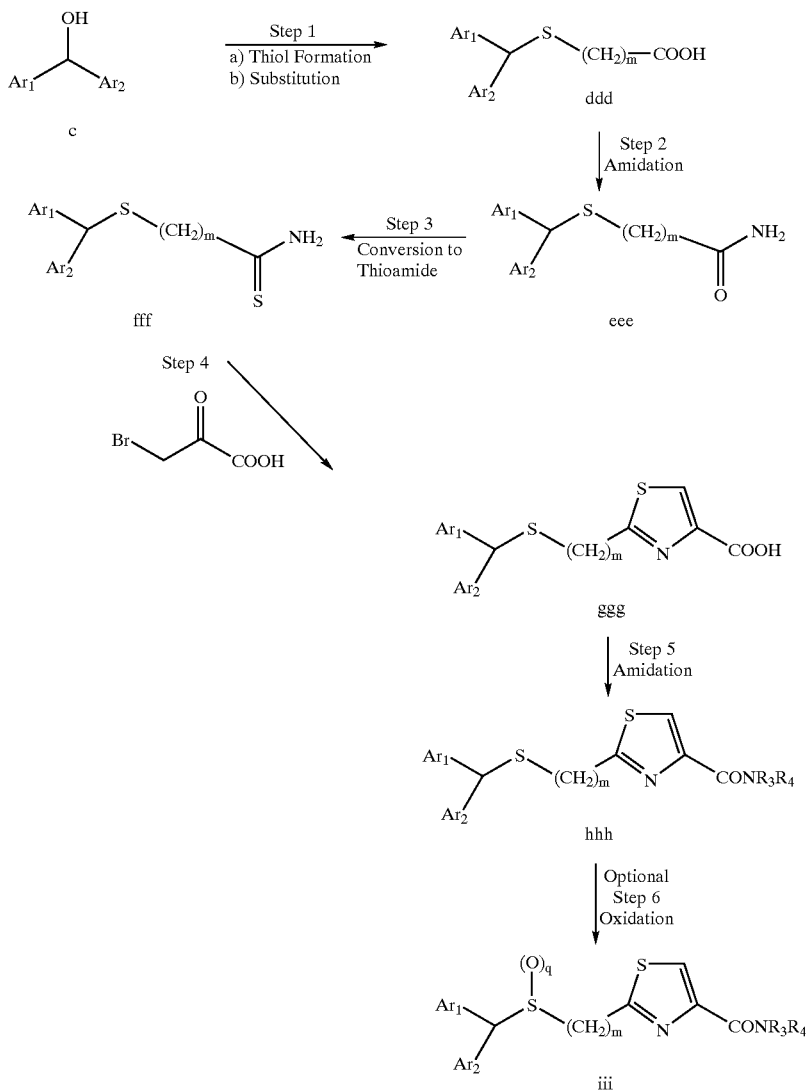

Scheme C, Steps 1 and 2: Synthesis of Compounds of General Structure ddd and eee.

The synthetic steps in Scheme C, steps 1 and 2 involve the same multistep general method described in Scheme A, steps 2–3, respectively to give compounds of structure eee.

Scheme C, Step 3: Synthesis of Compounds of General Structure fff.

The amide moiety in compound eee is converted to corresponding thioamide moiety fff with an appropriate sulfur-transfer reagent. For example, a mixture of compound eee and Lawesson's reagent (1.05 eqv) in a suitable solvent (dimethoxyethane or tetrahydrofuran) is heated to reflux until the disappearance of the starting material. After cooling, the desired product (compound fff) is obtained by employing known purification techniques (preferably by column chromatography and/or recrystallization).

Scheme C, Step 4: Synthesis of Compounds of General Structure ggg.

The thioamide moiety in compound fff is cyclized to the corresponding thiazole moiety. For example, a mixture of compound fff and an appropriate bromomethyl ketone (1.1 eqv) in a suitable solvent (e.g. ethanol) is heated to reflux until the disappearance of the starting material. After cooling, the desired product (compound ggg) is obtained by employing known purification techniques (preferably by column chromatography and/or recrystallization).

Scheme C, Steps 5–6: Synthesis of Compounds of General Structure hhh and iii.

The synthetic steps in Scheme C, steps 5 and 6 involve the same multistep general method described in Scheme A, steps 3 and 4, respectively to give compounds of structure hhh and iii.

A general synthetic procedure is set forth in Scheme D for preparing the compounds of formula (II-A), wherein n=0 and Y is

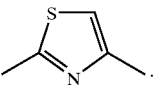

Scheme D

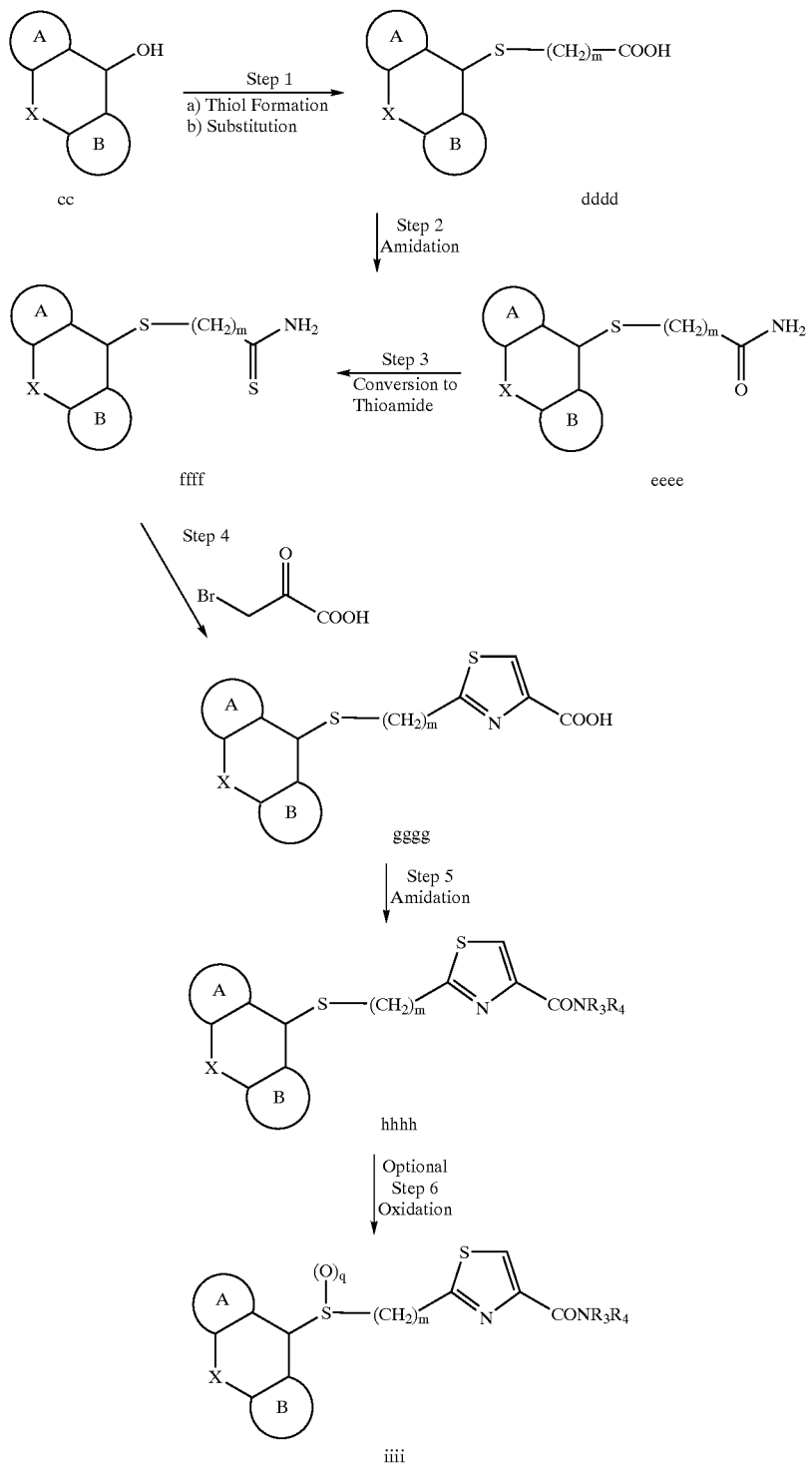

Scheme D, Steps 1–6: Synthesis of Compounds of General Structure hhhh and iiii.

The synthetic steps in Scheme D involve the same multistep general method described in Scheme C to give compounds of structure hhhh and optionally, iiii.

A synthetic procedure is set forth in Reaction Scheme E for preparing compounds of formula (I) or (I-A) wherein $R_1$ or $R_2$ can be taken together with either $R_3$ or $R_4$ to form a 3–7 member heterocyclic ring. The subsequently formed ring is represented in Scheme E by "G". In the present scheme, $R_1$ is taken together with $R_3$ to form heterocyclic ring "G". It is understood that $R_1$ may be also be taken with $R_4$ to form ring "G", or $R_2$ may be also be taken with $R_3$ to form ring "G", or $R_2$ may be also be taken with $R_4$ to form ring "G". The reagents and starting materials are commercially available, or readily synthesized by well-known techniques by one of ordinary skill in the arts. In Reaction Scheme E, all substituents, unless otherwise indicated, are as previously defined.

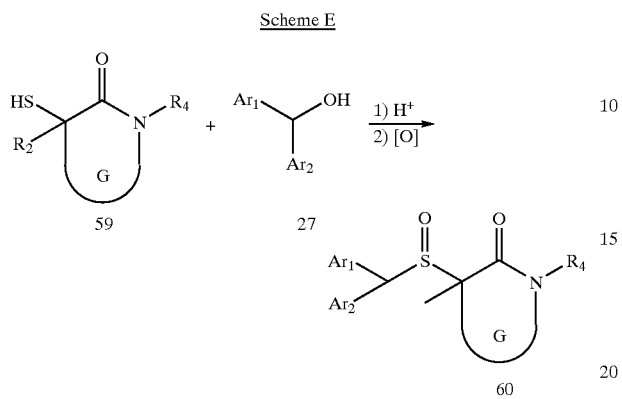

Scheme E

Scheme E, Steps 1 and 2: Synthesis of Compounds of General Structure 60, Containing Compounds of Formula (I) Wherein Either $R_1$ or $R_2$ are taken together with either $R_3$ or $R_4$ to Form a 3–7 Member Heterocyclic Ring "G".

In the first step, an appropriate mercaptolactam 59 is reacted with an appropriate diarylmethanol, compound 27, in the presence of a weak acid, in order to affect nucleophilic displacement at the methanol carbon to form the corresponding thioether. The appropriate mercaptolactam 59 and appropriate diaryl- or diheteroarylmethanol, 27 are ones in which $Ar_1$, $Ar_2$, $R_2$ and $R_4$ are as defined in the final product.

In the second step, the thioether formed in the first step is optionally oxidized with an appropriate oxidizing agent to provide compound 60. An appropriate oxidizing agent is one that oxidizes the thioether to its corresponding sulfoxide or sulfone.

A synthetic procedure is set forth in Reaction Scheme F for preparing compounds of formula (II-A), wherein $R_1$ or $R_2$ can be taken together with either $R_3$ or $R_4$ to form a 3–7 member heterocyclic ring. A similar procedure may be utilized to prepare the corresponding compounds of formula (II-A). The subsequently formed ring is represented in Scheme E by "G". In the present scheme, $R_1$ is taken together with $R_3$ to form heterocyclic ring "G". It is understood that $R_1$ may be also be taken with $R_4$ to form ring "G", or $R_2$ may be also be taken with $R_3$ to form ring "G", or $R_2$ may be also be taken with $R_4$ to form ring "0". The reagents and starting materials are commercially available, or readily synthesized by well-known techniques by one of ordinary skill in the arts. In Reaction Scheme F, all substituents, unless otherwise indicated, are as previously defined.

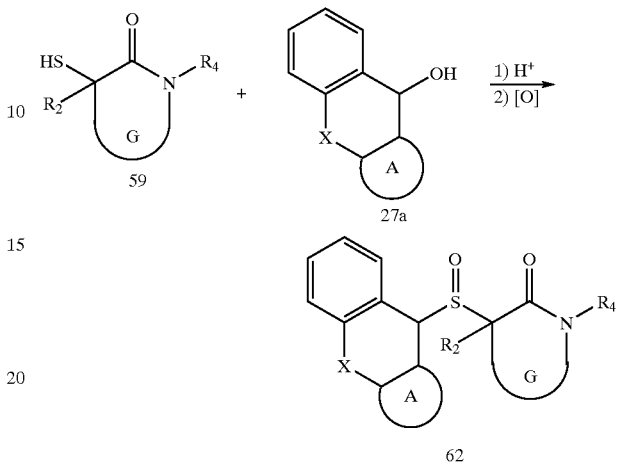

Scheme F

Scheme F, steps 1 and 2: Synthesis of Compounds of General Structure 62, Containing Compounds of Formula (II-A) Wherein Either $R_1$ or $R_2$ are taken together with Either $R_3$ or $R_4$ to Form a 3–7 Member Heterocyclic Ring "G".

In the first step, an appropriate mercaptolactam 59 is reacted with an appropriate diaryl- or diheteroarylmethanol, 27a, in the presence of a weak acid, in order to affect nucleophilic displacement at the methanol carbon to form the corresponding thioether. The appropriate mercaptolactam 61 and appropriate diaryl- or diheteroarylmethanol, 27a are ones in which A, X, $R_2$ and $R_4$ are as defined in the final product.

In the second step, the thioether formed in the first step is optionally oxidized with an appropriate oxidizing agent to provide compound 62. An appropriate oxidizing agent is one that oxidizes the thioether to its corresponding sulfoxide or sulfone.

EXAMPLES

Other features of the invention will become apparent in the course of the following descriptions of exemplary embodiments. These examples are given for illustration of the invention and are not intended to be limiting thereof. The following Examples 1–6 were synthesized according to Scheme 1.

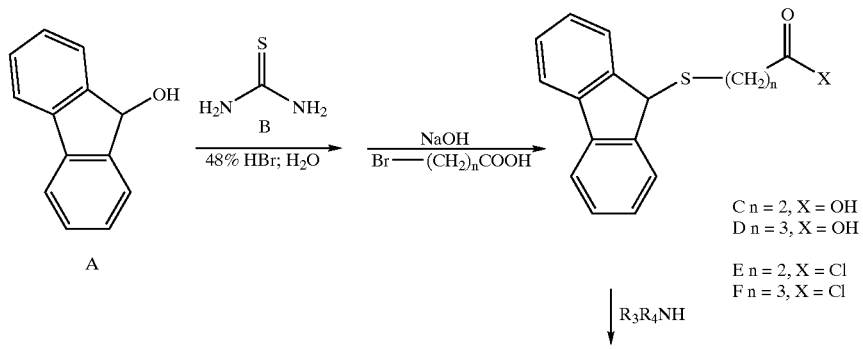

Scheme 1

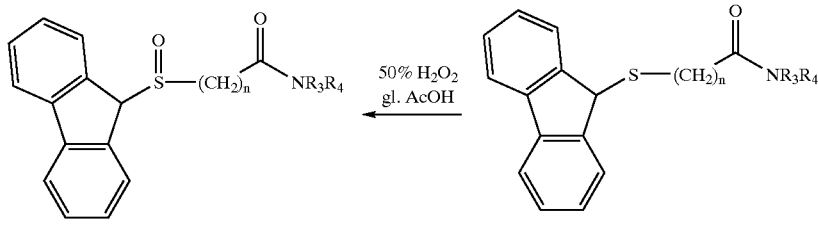

II-1 n = 2, R$_3$, R$_4$ = H
II-2 n = 2, R$_3$, R$_4$ = Me
II-3 n = 3, R$_3$, R$_4$ = H

G n = 2, R$_3$, R$_4$ = H
H n = 2, R$_3$, R$_4$ = Me
I n = 3, R$_3$, R$_4$ = H

Preparation of Compound C:

To a vigorously stirred mixture of thiourea (compound B, 5 g, 0.066 mol), 48% HBr (30 mL) and water (5 mL) at 70–75° C. was added 9-hydroxyfluorene (compound A, 9.28 g, 0.051 mol) in small portions, followed by additional amount of water (30 mL). The reaction mixture was then heated to 100–105° C. (bath temperature), maintained there for another 30 min and cooled to room temperature. The precipitated solid was filtered, washed with water and ether, successively and dried under vacuum to generate 14 g of the corresponding thiouronium salt that was used in the next step without any further purification.

To a vigorously stirred mixture of the above-mentioned thiouronium salt (10.47 g,) in 10 N NaOH (10.26 mL) and water (25 mL) at 60–65° C. was slowly added 3-bromopropionic acid (5.24 g, 0.034 mol) in water (20 mL). The reaction mixture was then heated to 105–110° C. (bath temperature), maintained there for another 30 min, cooled to room temperature, diluted with water (25 mL), and washed with ether (3×50 mL). The basic aqueous layer was acidified (pH 23) with conc. HCl and extracted into ethyl acetate (3×100 mL). The combined organic layer was dried (MgSO$_4$) and concentrated to generate 7.80 g of compound C that was used in the next step without any further purification; $^1$H-NMR (CDCl$_3$) δ 7.80 (m, 4H), 7.30 (m, 4H), 4.90 (s, 1H), 2.10 (m, 4H).

Preparation of Compound D:

This compound was prepared from compound A, following the same procedure as described above for the synthesis of compound D, except that 4-bromobutyric acid was used in place of 3-bromopropionic acid in the alkylation step; $^1$H-NMR (CDCl$_3$) δ 7.70 (m, 4H), 7.40 (m, 4H), 4.80 (s, 1H), 2.20 (t, 2H), 2.00 (t, 2H), 1.40 (m, 2H).

Preparation of Compound E:

To a refluxing solution of compound C (7.8 g, 0.029 mol) in benzene (40 mL) was slowly added thionyl chloride (5.3 mL). The mixture was refluxed for another 2 h, cooled, filtered and concentrated under reduced pressure to generate 8 g of compound E that was immediately taken into next step without any further purification.

Preparation of Compound F:

This compound was prepared from compound D, following the same procedure as described above for the synthesis of compound E from compound C.

Example 1

Synthesis of Compound G

Compound E (8 g) from previous step was dissolved in methylene chloride (20 mL) and added to a vigorously stirred, cooled (0° C.) 28% NH$_4$OH solution (50 mL). The ice-bath was removed and stirring was continued for another hour. The reaction mixture was diluted with water (30 mL) and extracted into methylene chloride (2×30 mL). The combined organic layer was washed with water (2×20 mL), 3% NaHCO$_3$ solution (2×30 mL), brine (1×30 mL), dried (Na$_2$SO$_4$) and concentrated to give a residue that was triturated with ether to generate 6.30 g of compound G; $^1$H-NMR (DMSO-d$_6$) δ 7.90 (d, 2H), 7.70 (d, 2H), 7.40 (m, 4H), 7.30 (broad, 1H), 6.80 (broad, 1H), 5.20 (s, 1H), 2.30 (t, 2H), 2.10 (t, 2H).

Example 2

Synthesis of Compound H

This compound was prepared from compound E, following the same procedure as described above for the synthesis of compound G, except that dimethylamine was used in place of 28% NH$_4$OH in the amination step; $^1$H-NMR (DMSO-d$_6$) δ 7.90 (d, 2H), 7.60 (d, 2H), 7.40 (m, 4H), 5.20 (s, 1H), 2.70 (2 singlets, 6H), 2.20 (m, 4H).

Example 3

Synthesis of Compound I

This compound was prepared from compound F, following the same procedure as described above for the synthesis of compound G from compound E; $^1$H-NMR (DMSO-d$_6$) δ 7.80 (d, 2H), 7.60 (d, 2H), 7.40 (m, 4H), 7.10 (broad, 1H), 6.70 (broad, 1H), 5.10 (s, 1H), 2.10 (t, 2H), 2.00 (t, 2H), 1.50 (m, 2H).

Example 4

Synthesis of Compound II-1

To a solution of compound G (5.15 g, 0.019 mol) in glacial acetic acid (20 mL) at room temperature was slowly added 50% H$_2$O$_2$ (1.2 eqv). The mixture was stirred for 1 h, poured into ice-water and filtered. The precipitated solid was thoroughly washed with water, followed by ether and dried under high vacuum to generate 4.42 g of compound II-1; white solid; mp 163–164° C.; R$_t$ 7.57 min. $^1$H-NMR (DMSO-d$_6$) δ 8.10–7.50 (a series of m, 8H), 7.40 (broad, 111), 6.90 (broad, 1H), 5.70 (s, 1H), 2.30 (m, 4H).

Example 5

Synthesis of Compound II-2

This compound was prepared from compound H, following the same procedure as described above for the synthesis of compound II-1 from compound G; white solid; mp 110–112° C.; R$_t$ 8.64 min. $^1$H-NMR (DMSO-d$_6$) δ 8.00 (t, 2H), 7.70 (d, 1H), 7.60 (d, 1H), 7.50 (m, 2H), 7.40 (q, 2H), 5.60 (s, 1H), 2.80 (s, 3H), 2.70 (s, 3H), 2.60–2.20 (a series of m, 4H).

Example 6

Synthesis of Compound II-3

This compound was prepared from compound I, following the same procedure as described above for the synthesis of compound II-1 from compound G; white solid; mp 161–162° C.; $R_t$ 7.61 min. $^1$H-NMR (DMSO-$d_6$) δ 8.20–7.60 (a series of m, 8H), 7.40 (broad, 1H), 6.90 (broad, 1H), 5.80 (s, 1H), 2.30 (m, 4H), 1.80 (m, 2H).

The following Examples 7–8 were synthesized according to Scheme 2.

0.0105 mol) in dry DMF (5 mL). The cooling bath was removed and the mixture was stirred for another 2 h. It was then poured into cold water (25 mL) and extracted into ethyl acetate (3×50 mL). The combined organic layer was washed with water, 2% citric acid, 3% sodium bicarbonate, water and brine, successively. Drying (MgSO$_4$) and solvent evaporation produced a residue that on trituration with cold ether generated 1.93 g of compound J; $^1$H-NMR (DMSO-$d_6$) δ 770 (m, 3H), 7.50 (d, 2H), 7.20 (m, 4H), 7.10 (broad, 1H), 6.80 (broad, 1H), 5.00 (s, 1H), 4.00 (m, 1H), 2.10 (m, 2H), 2.00 (m, 2H), 0.90 (d, 3H).

Scheme 2

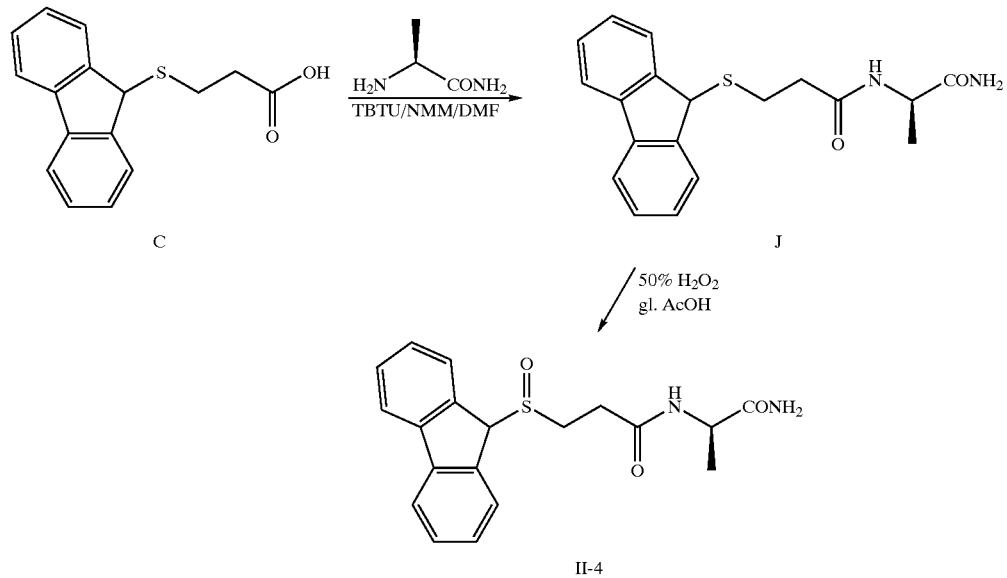

Example 7

Synthesis of Compound J

To a stirred solution of compound C (1.9 g, 0.007 mol) in dry DMF (20 mL) at 0° C. was added N-methylmorpholine ("NMM")(1.92 mL), followed by 2-(1H-Benzotriazol-1-yl)-1,1,3,3-tetramethyluronium tetrafluoroborate ("TBTU") (3.38 g. 0.0105 mol). The mixture was stirred for 10 min and to it added (L)-alaninamide (as hydrochloride salt) (1.3 g,

Example 8

Synthesis of Compound II-4

This compound was prepared from compound J, following the same procedure as described above for the synthesis of compound II-1 from compound G (Scheme 1); white solid (diastereomeric mixture); $R_t$ 7.16 min. $^1$H-NMR (DMSO-$d_6$) δ 8.30 (2 overlapping d, 1H), 8.20–7.60 (a series of m, 8H), 7.50 (d, 1H), 7.10 (d, 1H), 5.80 (s, 1H), 4.20 (m 1H), 2.60–2.40 (2 sets of m, 4H), 1.30 (2 overlapping d, 3H).

The following Examples 9–18 were synthesized according to Scheme 3.

Scheme 3

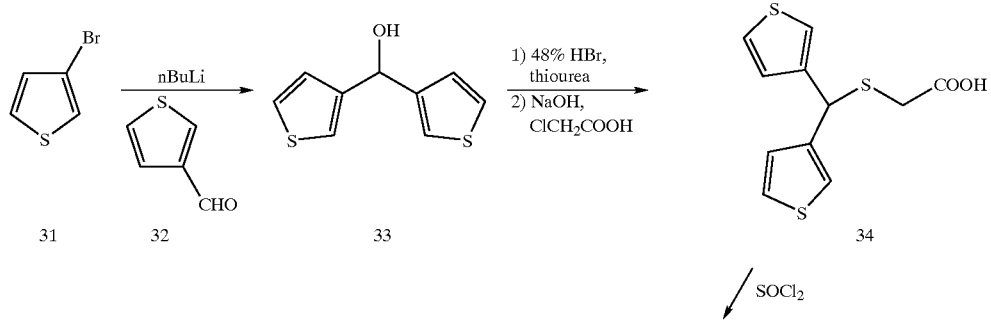

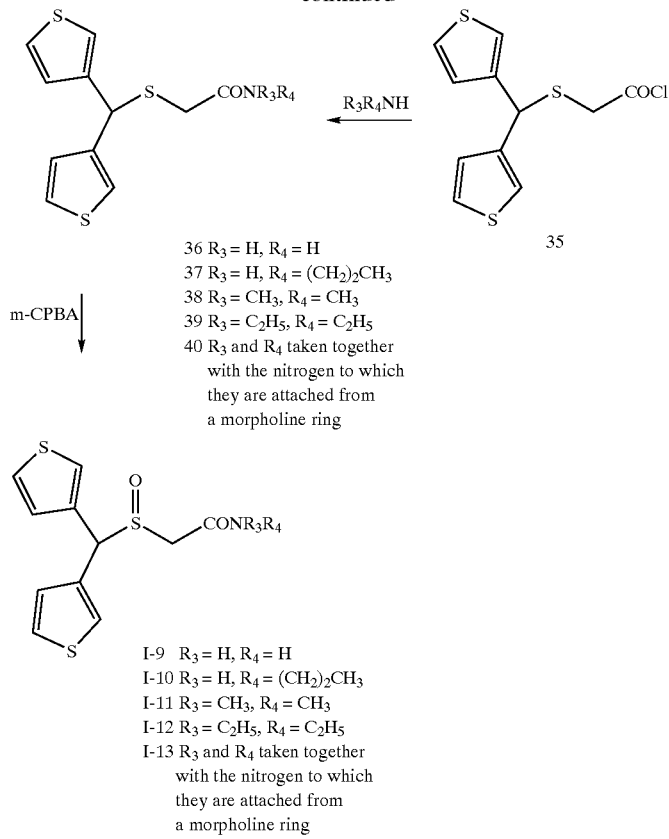

36 $R_3 = H, R_4 = H$
37 $R_3 = H, R_4 = (CH_2)_2CH_3$
38 $R_3 = CH_3, R_4 = CH_3$
39 $R_3 = C_2H_5, R_4 = C_2H_5$
40 $R_3$ and $R_4$ taken together with the nitrogen to which they are attached from a morpholine ring I-9 $R_3 = H, R_4 = H$
I-10 $R_3 = H, R_4 = (CH_2)_2CH_3$
I-11 $R_3 = CH_3, R_4 = CH_3$
I-12 $R_3 = C_2H_5, R_4 = C_2H_5$
I-13 $R_3$ and $R_4$ taken together with the nitrogen to which they are attached from a morpholine ring Preparation of Compound 33:
Scheme 3, Step 1:

In step 1a, 3-bromothiophene (10.22 g)(compound 31) in dry ether at a temperature −70° C. to −78° C. was reacted with n-butyllithium (25 ml of 2.5 M, 1.1 equivalents). After stirring for an additional period of time to allow for the completion of the halogen-metal exchange reaction, 3-thiophenecarboxaldehyde (6.39 g)(compound 32) in ether was slowly added to the reaction flask. Stirring was continued for an additional 2–3 h at the low temperature. The cooling bath was removed and the reaction mixture was slowly allowed to come to ambient temperature, followed by quenching, preferably by 50% aqueous $NH_4Cl$ solution. The mixture was extracted into an organic solvent (ether or ethyl acetate). The organic layer was washed with brine, dried ($MgSO_4$ or $Na_2SO_4$) and concentrated to give a crude product. Purification may be achieved by employing known purification techniques (preferably by column chromatography and/or recrystallization) to provide pure compound 33; $^1$H-NMR (CDCl$_3$) δ 7.40 (d, 2H), 7.30 (s, 2H), 7.10 (d, 2H), 6.00 (d, 1H), 2.20 (d, 2H). The method was an adaptation from a procedure previously described by Gronowitz, S.; Eriksson, B. *Arkiv Kemi* 1963, 335, incorporated herein by reference in its entirety.

Preparation of Compound 34:
Scheme 3, Step 2:

In the first step, thiourea (5 g, 1.3 equivalents) was taken into 48% HBr and water. The mixture was warmed (preferably to 60°–70° C.), followed by addition of compound 33 (10 g). The temperature of the reaction mixture was elevated (preferably to 90°–95° C.) and stirring was continued for an additional period of time for completion of the reaction. The reaction mixture was then cooled to room temperature (in some cases, an ice-bath might be needed) and the precipitated solid was filtered and thoroughly washed with water.

The wet solid was then taken into additional water and treated with an aqueous base, preferably sodium hydroxide solution. The mixture was warmed (preferably to 70°–80° C., but in some cases, a higher temperature might be needed) and to it chloroacetic acid (4.8 g, 1.1 equivalents) in water was added. The reaction mixture was maintained at an elevated temperature (preferably 100°–110° C.) for an appropriate period of time, cooled, taken into water and washed with an organic solvent (preferably ether). The basic aqueous layer was acidified with an inorganic acid solution (e.g. aqueous HCl solution). The aqueous (acidic) solution was then extracted several times into an organic solvent (e.g. ether or ethyl acetate). The combined organic layer was washed with brine, dried ($MgSO_4$ or $Na_2SO_4$) and concentrated to give the crude product 34 that may be used directly in the next step. However, purification may also be achieved by employing known purification techniques (e.g. recrystallization) to provide pure compound 34; $^1$H-NMR (CDCl$_3$) δ 7.30 (d, 2H), 7.20 (s, 2H), 7.10 (d, 2H), 5.40 (s, 1H), 3.10 (s, 2H).

The method is an adaptation from a procedure previously described in U.S. Pat. No. 4,177,290 (issued on Dec. 4, 1979) that is incorporated by reference herein in its entirety.

Preparation of Compound 35:
Scheme 3, Step 3:

A solution of the thioacid 34 (9.0 g) in benzene was brought to reflux temperature and to it was slowly added 1.1 equivalents of thionyl chloride. The mixture was refluxed until the disappearance of the starting material (as evidenced by analytical techniques), cooled and the solvent removed to give the crude product 35 that may be used directly in the next step. However, purification may also be achieved by employing known purification techniques (e.g. recrystallization) to provide pure compound 35.

Example 9

Synthesis of Compound 36

Scheme 3, Step 4:

The resulting thioacid chloride 35 (9.5 g) from the previous step was taken into an appropriate organic solvent (preferably tetrahydrofuran or methylene chloride) and treated with ammonia gas (or 28% aqueous solution). The reaction mixture is then partitioned between water and ethyl acetate. The separated organic layer is washed with water, dilute acid, and brine, dried over a drying agent (e.g. $MgSO_4$ or $Na_2SO_4$) and concentrated to produce 6.40 g of compound 36. Analytical Data: white solid; mp 88.5–89.5° C.; $R_t$ 9.61 min. $^1$H-NMR ($CDCl_3$) δ 7.40 (d, 2H), 7.30 (s, 2H), 7.20 (d, 2H), 6.40 (broad, 1H), 5.50 (broad, 1H), 5.40 (s, 1H), 3.10 (s, 2H).

Example 10

Synthesis of Compound 37

In a procedure similar to that of Example 9, treatment of 2.15 g of freshly prepared compound 35 with 2.2 g of n-propylamine generated a crude material that was purified by flash column chromatography (eluent: 30% ethyl acetate in hexanes) to generate 1.71 g of compound 37. Analytical Data: viscous oil, $R_t$ 12.30 min. $^1$H-NMR (DMSO-$d_6$) δ 7.90 (t, 1H), 7.50 (d, 2H), 7.40 (s, 1H), 7.10 (d, 2H), 5.60 (s, 1H), 3.30 (d, 1H), 3.10 (m, 3H), 1.30 (m, 2H), 0.80 (t, 3H).

Example 11

Synthesis of Compound 38

In a procedure similar to that of Example 9, treatment of 2.56 g of freshly prepared compound 35 with dimethylamine gas generated a crude material that was purified by flash column chromatography (eluent: 30% ethyl acetate in hexanes) to produce 1.96 g of compound 38. Analytical Data: white solid; mp 71–72° C.; $R_t$ 11.08 min. $^1$H-NMR ($CDCl_3$) δ 7.30–7.10 (m, 6H), 5.50 (s, 1H), 3.20 (s, 2H), 3.00 and 2.90 (2 sets of s, 6H).

Example 12

Synthesis of Compound 39

In a procedure similar to that of Example 9, treatment of 2.15 g of freshly prepared compound 35 with 2.74 g of diethylamine generated a crude product that was purified by flash column chromatography (eluent: 25% ethyl acetate in hexanes) to generate 1.56 g of compound 39. Analytical Data: white solid; mp 83–84° C.; $R_t$ 13.37 min. $^1$H-NMR ($CDCl_3$) δ 7.30–7.10 (m, 6H), 5.60 (s, 1H), 3.40 (q, 2H), 3.30 (q, 2H), 3.20 (s, 2H), 1.10 (2 overlapping t, 6H).

Example 13

Synthesis of Compound 40

In a procedure similar to that of Example 9, treatment of 2.15 g of freshly prepared compound 35 with 4 g of morpholine generated a crude product that was purified by flash column chromatography (eluent: 50% ethyl acetate in hexanes) to generate 2.02 g of compound 40. Analytical Data: white solid; mp 75.5–78° C.; $R_t$ 11.21 min. $^1$H-NMR ($CDCl_3$) δ 7.40–7.20 (2 sets of m, 6H), 5.50 (s, 1H), 3.70 (m, 4H), 3.60 (m, 2H), 3.40 (m, 2H), 3.20 (s, 2H).

Example 14

Synthesis of Compound I-9

To a cooled (–15° C. to –25° C.) solution of compound 36 (5.50 g) in either methylene chloride or chloroform, 1 equivalent of the oxidizing agent m-chloroperoxybenzoic acid (m-CPBA) in the same solvent was slowly added. Stirring was continued at the low temperature until the disappearance of the starting material, as evidenced by various analytical techniques. The reaction mixture was then thoroughly washed with a saturated sodium bicarbonate solution, water and brine, respectively, dried over a drying agent (e.g. $MgSO_4$ or $Na_2SO_4$) and concentrated. The resulting material was then purified by column chromatography and/or recrystallization to give compound I-9 (5.50 g). Analytical Data: white solid, mp 131–130° C. $^1$H-NMR ($CDCl_3$) δ 7.40 (m, 4H), 7.25 (d, 1H), 7.15 (d, 1H), 6.90 (broad, 1H), 5.60 (broad, 1H), 5.45 (s, 1H), 3.45 (d, 1H), 3.10 (d, 1H).

Example 15

Synthesis of Compound I-10

In a procedure similar to that of Example 14, compound 37 (1.67 g) was oxidized with 1 equivalent of the oxidizing agent m-chloroperoxybenzoic acid (m-CPBA), and then purified to give compound I-10 (1.40 g). Analytical Data: semi-solid; $R_t$ 8.95 min. $^1$H-NMR (DMSO-$d_6$) δ 8.00 (t, 1H), 7.40 (m, 4H), 7.10 (m, 2H), 5.30 (s, 1H), 3.20 (d, 1H), 3.10 (m, 1H), 3.00 (d, 1H), 2.90 (m, 1H), 1.20 (m, 2H), 0.80 (t, 3H).

Example 16

Synthesis of Compound I-11

In a procedure similar to that of Example 14, compound 38 (1.91 g) was oxidized with 1 equivalent of the oxidizing agent m-chloroperoxybenzoic acid (m-CPBA), and then purified to give compound I-11 (1.63 g). Analytical Data: white solid; mp 93–96° C; $R_t$ 7.79 min. $^1$H-NMR ($CDCl_3$) δ 7.50–7.30 (m, 6H), 5.70 (s, 1H), 3.60 (d, 1H), 3.40 (d, 1H), 3.10 and 2.90 (2 sets of s, 6H).

Example 17

Synthesis of Compound I-12

In a procedure similar to that of Example 14, compound 39 (1.53 g) was oxidized with 1 equivalent of the oxidizing agent m-chloroperoxybenzoic acid (m-CPBA), and then purified to give compound I-12 (1.35 g). Analytical Data: white solid; mp 93–95° C; $R_t$ 9.70 min. $^1$H-NMR ($CDCl_3$) δ 7.40–7.20 (m, 6H), 5.70 (s, 1H), 3.60 (d, 1H), 3.40 (m, 2H), 3.30 (d, 1H), 3.20 (m, 2H), 1.20 (t, 3H), 1.10 (t, 3H).

Example 18

Synthesis of Compound I-13

In a procedure similar to that of Example 14, compound 40 (2.00 g) was oxidized with 1 equivalent of the oxidizing agent m-chloroperoxybenzoic acid (m-CPBA), and then purified to give compound I-13 (1.60 g). Analytical Data: white solid; mp 59–73° C; $R_t$ 8.03 min. $^1$H-NMR ($CDCl_3$) δ 7.40–7.20 (2 sets of m, 6H), 5.60 (s, 1H), 3.80–3.20 (a series of m, 10H).

Example 19

Synthesis of Compound I-22

Compound I-22 was prepared following the same multi-step general method as described in Scheme A, utilizing 3-bromothiophene and benzaldehye in step 1. (M+H)=280.

Examples 20–39

Synthesis of Compounds I-1 Through 1–7 and 1–26 Through 1–38

Compounds I-1 through 1–7 and 1–26 through 1–38 were prepared following the same multistep general method as described in Scheme A utilizing the appropriately substituted amine $NHR_3R_4$ in step 3b. The analytical data is represented by each compound's mass spectrum (M+H) as shown in the following Table 3.

TABLE 3

| Example | Compound | (M + H) |
|---|---|---|
| 20 | I-1 | 300 |
| 21 | I-2 | 328 |
| 22 | I-3 | 328 |
| 23 | I-4 | 371 |
| 24 | I-5 | 328 |
| 25 | I-6 | 362 |
| 26 | I-7 | 356 |
| 27 | I-26 | 330 |
| 28 | I-27 | 397 |
| 29 | I-28 | 399 |
| 30 | I-29 | 322 (M + Na) |
| 31 | I-30 | 377 |
| 32 | I-31 | 377 |
| 33 | I-32 | 377 |
| 34 | I-33 | 384 |
| 35 | I-34 | 340 |
| 36 | I-35 | 355 |
| 37 | I-36 | 294 |
| 38 | I-37 | 376 |
| 39 | I-38 | 348 |

The following Examples 40–41 were synthesized according to Scheme 4.

Preparation of Compound 43:

A mixture of compound 41 (0.75 g)(Dondoni, A. et. al. *J. Org. Chem.* 1988, pp. 1748–1761), acetic anhydride (3 equivalents) and anhydrous pyridine (2–3 ml/mmol of alcohol) was stirred overnight at room temperature, or until the reaction was complete by thin layer chromatography. The reaction mixture was then poured into cold water and extracted into ethyl acetate (3×25 mL). The combined organic phase was successively washed with saturated sodium bicarbonate solution, water, brine, dried (sodium sulfate) and concentrated to generate the desired product compound 43 (0.84 g). Analytical Data: $R_f$=0.6 (2.5% methanol/ethyl acetate); $^1$H-NMR (CDCl$_3$) δ 7.72 (s, 1H), 7.47 (m, 1H), 7.38–7.22 (m, 5H), 7.11 (s, 1H), 2.17 (s, 3H).

Preparation of Compound 44:

Compound 42 (0.92 g) was reacted in a manner similar to that described above in the preparation of compound 41. The resulting crude ester was purified by flash chromatography (eluent: 4:1 hexane/ethyl acetate) to give 0.41 g of compound 44. Analytical Data: $R_f$=0.32 (4:1 hexane/ethyl acetate); $^1$H-NMR (CDCl$_3$) δ 7.83 (s, 1H), 7.42 (s, 1H), 7.36 (m, 1H), 7.17 (m, 1H), 7.00 (m, 1H), 2.19 (s, 3H).

Preparation of Compound 45:

To a stirring solution of compound 43 (0.84 g) and methyl thioglycolate (1.2 equivalents) in anhydrous dichloromethane (4–5 mL/mmol) at 0° C. under argon was added trimethylsilyl trifluoromethane (TMS-triflate, 1 equivalent). The reaction mixture was allowed to warm to room temperature and stirred until complete (2–6 h). It was then diluted with dichloromethane, washed with saturated sodium bicarbonate solution, dried (sodium sulfate), concentrated and dried under high vacuum to give compound 45 (1.01 g) that was used directly in the next step without any further purification. Analytical Data: $R_f$=0.62 (2.5% methanol/ethyl acetate); $^1$H-NMR (CDCl$_3$) δ 7.75 (s, 1H), 7.5 (d, 1H), 7.38–7.27 (m, 5H), 5.72 (s, 1H), 3.69 (s, 3H), 3.25 (q, 2H).

Preparation of Compound 46:

Compound 44 (0.41 g) was reacted in a manner similar to that described above in the preparation of compound 45 to give compound 46 (0.30 g). Analytical Data: $R_f$=0.62 (2.5% methanol/ethyl acetate); $^1$H NMR (CDCl$_3$) δ 7.75 (s, 1H), 7.39 (s, 1H), 7.36 (m, 1H), 7.17 (broad, 1H), 6.94 (m, 1H), 6.07 (s, 1H), 3.72 (s, 3H), 3.30 (q, 2H).

Scheme 4

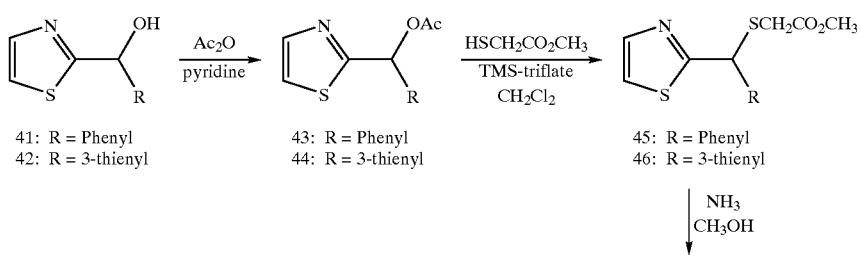

41: R = Phenyl
42: R = 3-thienyl

43: R = Phenyl
44: R = 3-thienyl

45: R = Phenyl
46: R = 3-thienyl

| NH$_3$
| CH$_3$OH

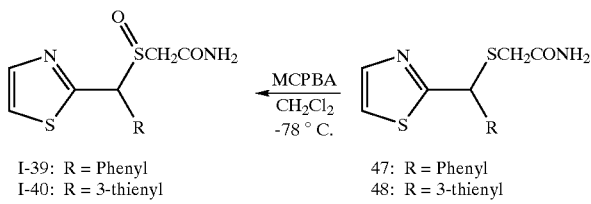

I-39: R = Phenyl
I-40: R = 3-thienyl

47: R = Phenyl
48: R = 3-thienyl

Preparation of Compound 47:

Anhydrous ammonia was bubbled into a stirring solution of compound 45 (1.0 g) in methanol (10 mL/mmol) at 0° C. for 5–10 minutes. The reaction mixture was allowed to warm to room temperature, stirred for additional 5–7 h, concentrated under reduced pressure and dried under vacuum. The crude product was purified by flash chromatography (eluent: 5% methanol/ethyl acetate) to give 0.48 g of compound 47. Analytical Data: $R_f$=0.20 (5% methanol/ethyl acetate); $^1$H-NMR (CDCl$_3$) δ 7.77 (s, 1H), 7.47 (d, 1H), 7.44–7.27 (m, 5H), 5.53 (broad, 1H), 3.22 (q, 2H).

Preparation of Compound 48:

Compound 46 (0.30 g) was reacted in a manner similar to that described above in the preparation of compound 47 to give compound 48 (0.25 g). Analytical Data: $R_f$=0.20 (5% methanol/ethyl acetate); $^1$H-NMR (CDCl$_3$): δ 7.72, (s, 1H), 7.31 (s, 1H), 7.28 (m, 1H), 7.17 (s, 1H), 6.97 (m, 1H), 6.84 (broad, 1H), 6.11 (broad, 1H), 5.86 (s, 1H), 3.25 (q, 2H).

Example 40

Synthesis of Compound I-39

To a stirring solution of compound 47 (0.48) in anhydrous dichloromethane (10 mL/mmol) at −78° C. was added a solution of m-CPBA (1.0 equivalent) in dichloromethane (5–8 mL/mmol). After an additional stirring for 1 h, the reaction mixture was allowed to warm to −30 to −40° C. and quenched with 10% aqueous Na$_2$S$_2$O$_3$ solution. Separated organic phase was successively washed with saturated sodium bicarbonate solution, water and brine, dried (sodium sulfate), and concentrated to generate compound I-37 (0.31 g). Analytical Data: $R_f$=0.13 (5% methanol/ethyl acetate); $^1$H-NMR (CDCl$_3$) major diastereomer: δ 7.92 (s, 1H), 7.61 (m, 2H), 7.44–7.36 (m, 5H), 7.00 (broad, 1H), 5.61 (s, 1H), 3.42 (q, 2H); minor diastereomer: δ 7.86 (s, 1H), 7.55 (m, 2H), 7.44–7.36 (m, 5H), 6.83 (broad, 1H), 5.55 (s, 1H), 3.61 (q, 2H).

Example 41

Synthesis of Compound I-40

Compound 48 (0.25 g) was reacted in a manner similar to that described above in the preparation of compound 47 to give compound I-39 (0.105 g) (diastereomeric mixture). Analytical Data: $^1$H-NMR (DMSO-d$_6$) major diastereomer: δ 8.03 (s, 1H), 7.92 (s, 1H), 7.78 (broad, 1H), 7.68 (s, 1H), 7.36 (broad, 1H)), 7.17 (m, 1H), 6.50 (s, 1H), 3.47 (q, 2H); minor diastereomer: δ 7.97 (s, 1H), 7.86 (s, 1H), 7.78 (broad, 1H), 7,72 (s, 1H), 7.36 (broad, 1H), 7.22 (m, 1H), 6.39 (s, 1H), 3.36 (q, 2H).

Example 42

Synthesis of Compound II-9

Starting with 9-hydroxyfluorene, this compound was prepared following the same multistep general method as described in Scheme 3 above, and utilizing L-Alanine-NH$_2$ in the amination step. Analytical Data: white solid (diastereomeric mixture); $R_t$ 7.27 min and 7.41 min. $^1$H-NMR (DMSO-d$_6$) δ 8.40–7.00 (a series of m and d, 11H), 5.60 and 5.70 (2 sets of s, 1H), 4.20 (m, 1H), 3.20 and 3.00 (2 sets of dd, 2H), 1.20 (2 overlapping doublets, 3H).

Example 43

Synthesis of Compound II-23

Starting with 9-hydroxyfluorene, this compound was prepared following the same multistep general method as described in Scheme 3 above, and utilizing 28% aqueous ammonia in the amination step. Analytical Data: white solid; mp 178.5–180° C.; $R_t$ 7.48 min. $^1$H-NMR (CDCl$_3$) δ 7.90–7.40 (a series of m, 8H), 6.60 (broad, 1H), 5.40 (s, 1H), 5.30 (broad, 1H), 2.80 (d, 1H), 2.60 (d, 1H).

Example 44

Synthesis of Compound II-25

Starting with dibenzosuberol, this compound was prepared following the same multistep general method as described in Scheme 3 above, and utilizing 28% aqueous ammonia in the amination step. Analytical Data: white solid; mp 182–190° C.; $R_t$ 8.43 min. $^1$H-NMR (DMSO-d$_6$) δ 7.80 (d, 1H), 7.60 (d, 1H), 7.40 (m, 8H), 5.50 (s, 1H), 3.60 (m, 2H), 3.50 (d, 1H), 3.40 (d, 1H), 2.90 (m, 2H).

Example 45

Synthesis of Compound II-26

Starting with dibenzosuberol, this compound was prepared following the same multistep general method as described in Scheme 3 above, utilizing dimethylamine in the amination step. Analytical Data: white solid; mp 112.5–115° C.; $R_t$ 10.36 min. $^1$H-NMR (DMSO-d$_6$) δ 7.60 (d, 1H), 7.40 (m, 7H), 5.50 (s, 1H), 4.00 (d, 1H), 3.60 (d, 1H), 3.50 (m, 2H), 2.90 (s, 3H), 2.80 (m, 2H), 2.70 (s, 3H).

Examples 46–91

Synthesis of Compounds II-6 Through II-8, II-10 Through II-15, II-24, II-27, II-30 Through II-54, II-56 Through II-91

Compounds II-6 through II-8, II-10 through II-15, II-24, II-27, II-30 through II-54, II-56 through II-91 were prepared following the same multistep general method as described in Scheme B incorporating the appropriate reactants to form the desired product. The analytical data is represented by each compound's mass spectrum (M+H) as shown in the following Table 4.

TABLE 4

| Example | Compound | (M + H) |
|---|---|---|
| 46 | II-6 | 314 |
| 47 | II-7 | 342 |
| 48 | II-8 | 300 |
| 49 | II-10 | 348 |
| 50 | II-11 | 314 |
| 51 | II-12 | 348 |
| 52 | II-13 | 314 |
| 53 | II-14 | 328 |
| 54 | II-15 | 341 |
| 55 | II-24 | 371 |
| 56 | II-27 | 288 |
| 57 | II-30 | 286 |
| 58 | II-31 | 415 |
| 59 | II-32 | 363 |
| 60 | II-33 | 363 |
| 61 | II-34 | 316 |
| 62 | II-35 | 300 |
| 63 | II-36 | 326 |
| 64 | II-37 | 298 |
| 65 | II-38 | 376 |
| 66 | II-39 | 288 |
| 67 | II-40 | 329 |
| 68 | II-41 | 343 |
| 69 | II-42 | 318 |
| 70 | II-43 | 328 |

TABLE 4-continued

| Example | Compound | (M + H) |
|---------|----------|---------|
| 71 | II-44 | 343 |
| 72 | II-45 | 376 |
| 73 | II-46 | 330 |
| 74 | II-47 | 358 |
| 75 | II-48 | 343 |
| 76 | II-49 | 343 |
| 77 | II-50 | 371 |
| 78 | II-51 | 359 |
| 79 | II-52 | 373 |
| 80 | II-53 | 369 |
| 81 | II-54 | 286 |
| 82 | II-56 | 316 |
| 83 | II-57 | 359 |
| 84 | II-58 | 314 |
| 85 | II-59 | 328 |
| 86 | II-60 | 334 |
| 87 | II-61 | 340 |
| 88 | II-62 | 385 |
| 89 | II-63 | 384 |
| 90 | II-64 | 338 |
| 91 | II-65 | 384 |

The following Example 92 was synthesized according to Scheme 5.

Preparation of Compound M:

A mixture of dimethyl phthalate (compound K, 10 g, 0.51 mol), 3,4-dimethoxyacetophenone (compound L, 9.74 g, 0.054 mol), and powdered sodium methoxide (2.76 g, 0.051 mol) was heated at reflux overnight, cooled to room temperature, and concentrated in vacuo. The yellow slurry was suspended in water (100 mL), stirred for 10 min, acidified with 6N HCl (pH 1–2), and filtered. The residue was placed in ethanol (200 mL), heated to reflux for 30 min, cooled to room temperature, and filtered. The residue was washed with cold ethanol and dried in vacuo to generate compound M as a bright yellow fluffy solid (4.1 g) that was used without any further purification. Analytical Data: $^1$H-NMR (CDCl$_3$) δ 3.99 (s, 3H), 4.02 (s, 3H), 6.99 (d, 1H), 7.68–7.75 (m, 2H), 7.85 (m, 2H), 8.07 (d, 1H), 8.09 (s, 1H); MS: (M+H)$^+$=311.

Preparation of Compound N:

A mixture of compound M (3.37 g, 0.011 mol), hydrazine (0.41 mL, 0.013 mol) and ethanol (250 mL) under nitrogen was heated to reflux for 6 h, cooled to room temperature and filtered. The residue was washed with ethanol and dried to give compound N as a yellow solid (2.0 g). Analytical Data: $^1$H NMR (CDCl$_3$) δ 3.85 (s, 3H), 3.89 (s, 3H), 7.17 (d, 1H), 7.38–7.43 (m, 1H), 7.55 (m, 2H), 7.60 (d, 1H), 7.85 (d, 1H), 7.95 (s, 1H); MS: (M+H)$^+$=307.

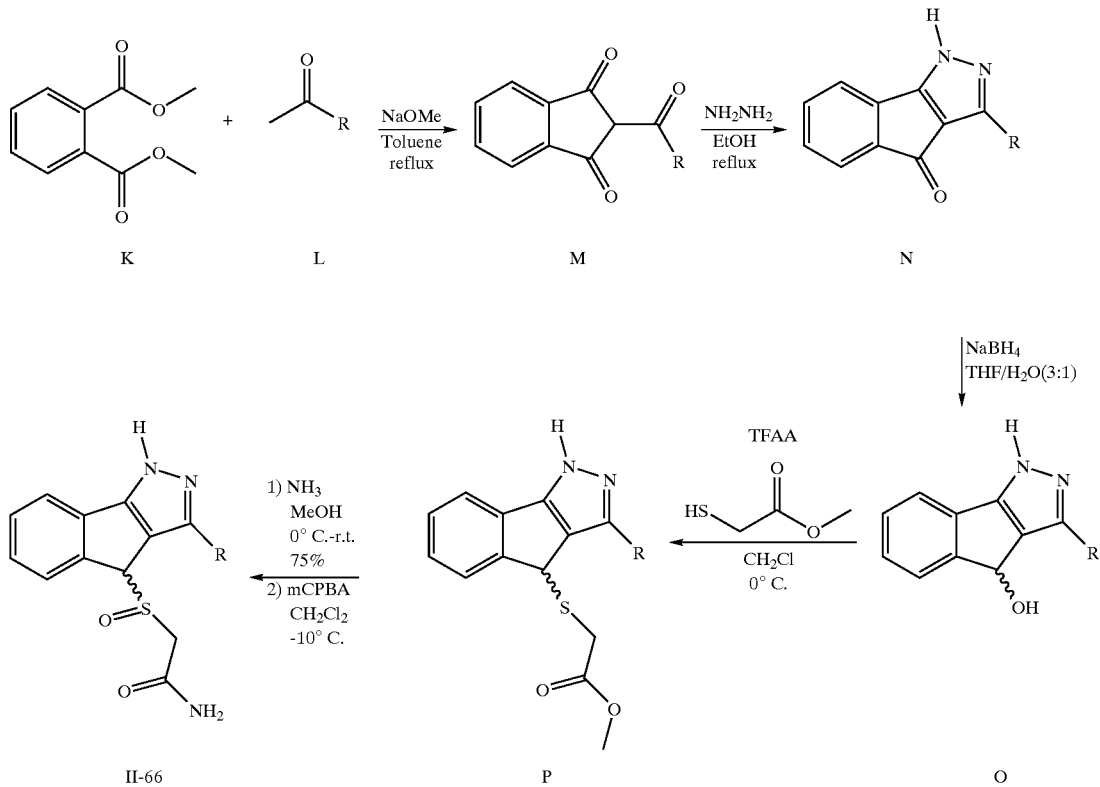

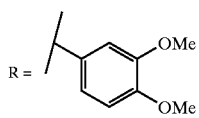

Preparation of Compound O:

To a stirred solution of compound N (0.084 g, 0.27 mmol) in THF/H$_2$O (3:1, 8 mL) at room temperature under nitrogen was added solid sodium borohydride (0.029 g, 0.63 mmol) in one portion. The reaction mixture was cooled to 0° C., stirred for 1 h, warmed to room temperature, diluted with ethyl acetate and washed with water. The organic phase was dried (magnesium sulfate) and concentrated in vacuo. The residue, on trituration with ether, generated compound O (0.077 g) as a yellow solid that was used without further purification. Analytical Data: $^1$H NMR (CDCl$_3$) δ 3.86 (s, 3H), 3.87 (s, 3H), 5.53 (s, 1H), 6.79 (d, 1H), 7.29 (t, 2H), 7.46 (d, 1H), 7.50 (s, 2H), 7.58 (t, 1H); MS: (M+H)$^+$=309.

Preparation of Compound P:

To a stirred solution of compound O (1.55 g, 0.005 mol) in CH$_2$Cl$_2$ (40 mL) under nitrogen at 0° C. was added methyl thioglycolate (0.54 mL, 0.006 mmol). Next, trifluoroacetic anhydride (1.42 mL, 0.01 mol) was added dropwise to the reaction mixture. The reaction mixture was stirred at 0° C. for 0.5 h, warmed to room temperature, stirred overnight, quenched with saturated aqueous sodium bicarbonate and extracted into ethyl acetate (3×25 mL). The organic layer was washed with water, brine, dried (magnesium sulfate), and concentrated in vacuo to generate compound P as a yellow solid (1.75 g) that was used without any further purification. Analytical Data: $^1$H NMR (CDCl$_3$) δ 2.77 (q, 2H), 3.33 (s, 3H), 3.93 (s, 3H), 4.00 3H), 4.99 (s, 1H), 6.96 (d, 1H), 7.23–7.42 (m, 2H), 7.47 (d, 1H), 7.49 (d, 1H), 7.64 (d, 1H), 7.69 (d, 1H), 7.72 (d, 1H); MS: (M+H)$^+$=397.

Example 92

Synthesis of Compound II-66

Starting from compound P, this compound was generated following the procedure as described above for the preparation of compound 47, and in Example 35 for the synthesis of compound I-37. Thus, 0.050 mg of compound P, on treatment with ammonia in the first step, followed by oxidation with m-CPBA in the next step, generated 0.011 g of compound II-66. Analytical Data: $^1$H-NMR (CDCl$_3$) δ 2.75 (d, 1H), 2.88 (d, 1H), 3.92 (s, 3H), 3.96 (s, 3H), 5.67 (s, 1H), 6.80 (s, 1H), 6.94 (d, 1H), 7.37 (t, 1H), 7.45–7.52 (m, 2H), 7.58 (d, 1H), 7.64 (s, 1H), 7.79 (d, 1H); MS: (M+H)$^+$=420.

Compounds of formula (VI) and (VII) (Tables 2A and 2B) are readily prepared using the appropriate cyclic maleimides. For example, the cyclic maleimides used in the preparation compounds VI-1, 2, 6, 7, 8 (Table 2A) and VIII-1, 2, 6, 8 (Table 2B) are commercially available. Other cyclic maleimides are known in the literature (see, for example, Bayer et al. Montash. Chem. 1997, 91 and Kakiuchi et al. Chem. Lett. 1998, 1001, both of which are incorporated by reference herein in their entirety).

In addition, a general synthetic scheme is set forth in Scheme 6 for preparation of cyclic imides (C3 and C4) utilized in the synthesis of compounds VI-3, 5 (Table 2A) and VIII-3, 4 (Table 2B).

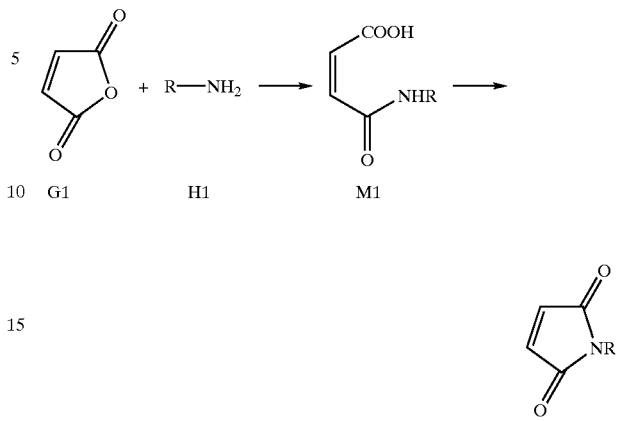

Scheme 6

C3: R = (CH$_2$)$_2$OMe
C4: R = (s)-CH(Me)CH$_2$OH

In Scheme 6, the reaction of maleic anhydride (compound G1) with an appropriate amine (compound H1, wherein R is —(CH$_2$)$_2$OMe or (s)-CH(Me)CH$_2$OH) generates the corresponding maleimic acid (compound M1). Cyclization of compound M1 in presence of Ac$_2$O/NaOAc at room temperature or in toluene/triethylamine under reflux conditions generates compounds C3 and C4.

Preparation of Compound C3:

To a solution of maleic anhydride (compound G1, 1 equiv.) in acetic acid was added 2-methoxyethylamine (compound H1, R=(CH$_2$)$_2$OMe, 1 equiv.) in a dropwise fashion. After stirring overnight at room temperature, the reaction mixture was concentrated to generate crude compound M1 that was taken in a mixture of acetic anhydride and NaOAc (0.6 equiv.). The resulting mixture was stirred at 90° C. for 2 h, cooled to room temperature, quenched with cold water and extracted into ether. The combined organic layers were washed with brine, dried (magnesium sulfate) and concentrated to generate compound C3, which was directly used without further purification; $^1$H-NMR (DMSO-d$_6$): δ 7.02 (s, 2H), 3.54 (m, 2H), 3.44 (m, 2H), 3.20 (s, 3H).

Preparation of Compound C4:

A solution of (S)-2-aminopropanol (compound H1, R=(s)-CH(Me)CH$_2$OH, 1 equiv.) in absolute ethanol was slowly added to a solution of maleic anhydride (compound G1, 1 equiv.). The resulting mixture was stirred at room temperature overnight. The separated solid was filtered, washed with ether, taken into toluene and treated with triethylamine. The resulting mixture was refluxed for 4 h under a Dean-Stark trap, cooled to room temperature, concentrated and passed through a pad of silica gel (eluent: ethyl acetate) to give compound C4; $^1$H-NMR (Acetone-d$_6$): δ 6.80 (s, 2H), 4.20 (m, 1H), 3.91 (m, 2H), 3.64 (m, 1H), 1.29 (d, 3H).

The following Examples 92a–92q were synthesized following the procedures outlined in Scheme 7.

Scheme 7

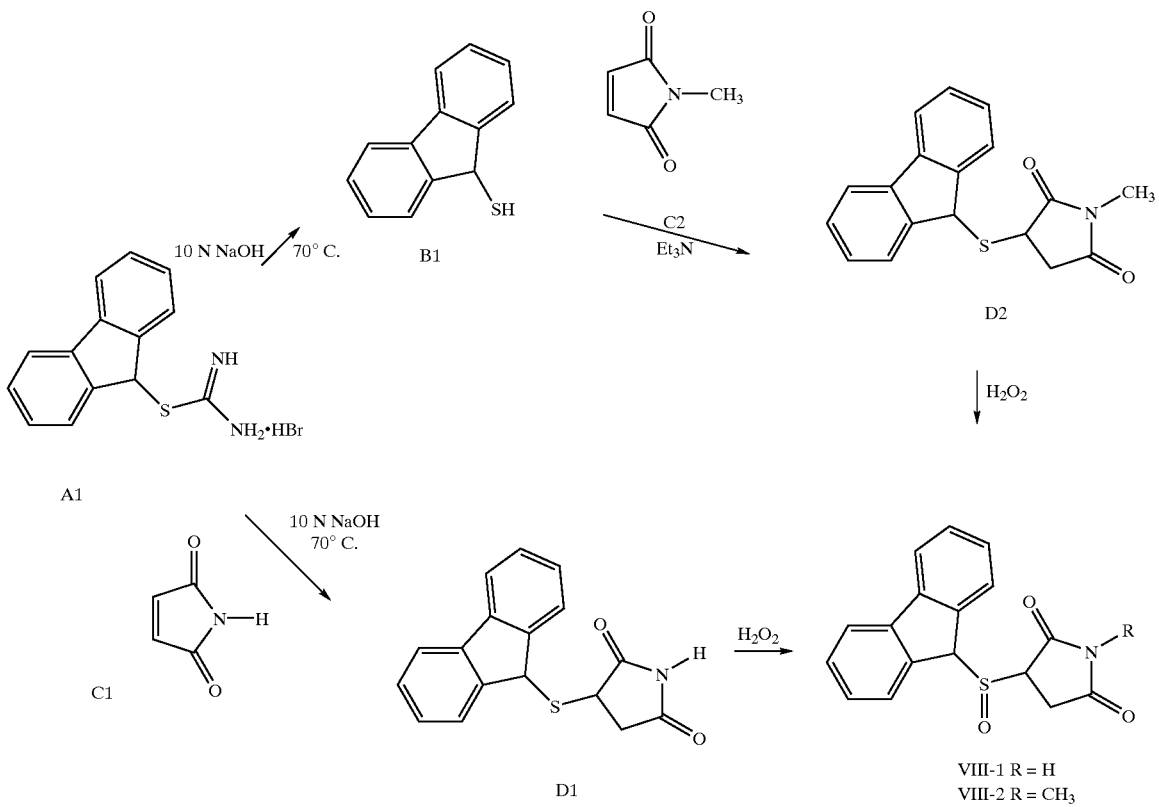

In Scheme 7, the reaction of an appropriate thiol (generated from corresponding thiouronium salt), with an appropriate cyclic imide in presence of a base generates the corresponding thioether. The thioether may be oxidized to give the corresponding sulfoxide. For example, thiol B1, generated from its corresponding thiouronium salt A1 (prepared from compound A as disclosed in Scheme 1), reacts with N-methylmaleimide (compound C2) in presence of triethylamine to generate thioether D2 that on subsequent oxidation with hydrogen peroxide in glacial acetic acid produces the corresponding sulfoxide, compound VIII-2 (Table 2B). Alternatively, the thioether may be directly produced by reacting the appropriate thiouranium salt with the appropriate cyclic imide in the presence of a base. Thus, thioether D1 was directly produced from the reaction of its corresponding thiouranium salt A1 with maleimide (C1), in presence of 10 N NaOH. Oxidation of D1 generated the corresponding sulfoxide VIII-1 (Table 2B).

Example 92a

Synthesis of Compound VIII-1

A mixture of compound A1 (4 g, 12.46 mmol.), 10 N NaOH (4 mL) and water (10 mL) was stirred at 70° C. for 0.5 h. Maleimide (compound C1, 1.2 g, 12.37 mmol.) in ethanol (20 mL) was then added to the reaction mixture and stirring was continued at 70° C. for another 2 h. After cooling to room temperature, the separated solid was filtered, washed successively with water, hexane and ether. The filtrate containing the desired product was extracted into ethyl acetate. The combined organic layers were washed successively with water and brine, dried ($MgSO_4$), and concentrated to furnish the crude product that was purified by flash chromatography (hexane:ethyl acetate 1:1) to give 0.510 g of compound D1; $^1$H-NMR (DMSO-$d_6$): δ 11.33 (s, 1H), 7.90–7.32 (a series of m, 8H), 5.49 (s, 1H), 3.79 (dd, 1H), 2.64 (dd, 1H), 2.24 (dd, 1H).

Oxidation of compound D1 with hydrogen peroxide, as described above, generated the title compound as a mixture of diastereomers; $R_t$=10.16 min; $^1$H-NMR (DMSO-$d_6$): δ 11.82 (s, 0.11H), 11.44 (s, 0.89H), 8.03–7.39 (a series of m, 8H), 5.99 (s, 0.1H), 5.72 (s, 0.89H), 4.58 (m, 0.11H), 3.22 (dd, 0.891H), 2.79 (dd, 3.32, 0.11H), 2.55 (dd, 0.89H), 1.67 (dd, 0.89H). MS: 312 (M+H), 334 (M+Na).

Example 92b

Synthesis of Compound VIII-2

A mixture of compound A1 (1 equiv) in water and 10 N NaOH (4–5 equiv) was stirred at 70° C. for 3–5 h. The mixture was cooled to 0° C., acidified with dil HCl and extracted into ether. The combined organic layers were washed with brine, dried (magnesium sulfate), and concentrated to furnish compound B1 that was used without further purification; $^1$H-NMR (DMSO-$d_6$): δ 7.87–7.35 (a series of m, 8H), 5.21 (d, 1H), 3.55 (d, 1H).

A mixture of compound B1 (1 equiv.), compound C2 (1 equiv.), and triethylamine in ethyl acetate:methanol (4:1) was stirred at room temperature for 2–5 h, concentrated and purified by flash chromatography (hexane:ethyl acetate 2:1) to give compound D2; $^1$H-NMR (DMSO-$d_6$): δ 7.90–7.35 (series of m, 8H), 5.49 (s, 1H), 3.76 (m, 1H), 2.73 (s, 3H), 2.61(dd, 1H), 2.24 (dd, 1H).

Oxidation of compound D2 with hydrogen peroxide, as described above, generated the title compound as a mixture of diastereomers; $R_t$ 10.30 min; $^1$H-NMR (DMSO-d,): δ 8.04–7.37 (a series of m, 8H), 5.98 (s, 0.08H), 5.77 (s, 0.92H), 4.61 (m, 0.08H), 3.31–2.50 (a series of m and dd, 5.08l1), 1.58 (dd, 0.92H). MS: 348 (M+Na).

Example 92c

Synthesis of Compound VI-1

The title compound was prepared using the appropriate starting materials and following the methodologies described above. Analytical data: $R_t$ 9.20 min. and 9.41 min (diastereomers); $^1$H-NMR (DMSO-d$_6$): δ 11.62 and 11.53 (2 singlets, 1H), 7.57–7.32 (a series of m, 10l1), 6.07 (s, 0.4H), 5.33 (s, 0.6H), 3.74 (m, 0.6H), 3.55 (m, 0.4H), 3.14 (dd, 0.4H), 2.96 (dd, 0.6H), 2.82 (dd, 0.4H), 2.57 (dd, 0.6H). MS: 312 (M–H).

Example 92d

Synthesis of Compound VI-2

The title compound was prepared using the appropriate starting materials and following the methodologies described above. Analytical data: $R_t$ 8.05 min. and 8.17 min (diastereomers). $^1$H-NMR (DMSO-d$_6$): δ 7.58–7.26 (a series of m, 10H), 6.04 (s, 1H), 3.31–2.49 (a series of m, 6H). MS: 350 (M+Na).

Example 92e

Synthesis of Compound VI-3

The title compound was prepared using the appropriate starting materials and following the methodologies described above. Analytical data: $R_t$ 8.38 min and 8.46 min (diastereomers); $^1$H-NMR (DMSO-d$_6$): δ 7.58–7.01 (a series of m, 10H), 6.03 (s, 0.23H), 5.38 (s, 0.77H), 3.84–3.01 (a series of m, 9.23H), 2.61 (dd, 0.77H). MS: 394 (M+Na).

Example 92f

Synthesis of Compound VI-4

The title compound was prepared using the appropriate starting materials and following the methodologies described above. Analytical data: $R_t$ 7.38 min. (overlapping diastereomers); $^1$H-NMR (DMSO-d$_6$): δ 7.58–7.33 (a series of m, 10H), 6.02 (s, 0.33H), 5.38 (s, 0.67H), 4.67 (m, 1H), 3.79–2.94 (a series of m, 5.33H), 2.60 (dd, 0.67H). MS: 380 (M+Na).

Example 92g

Synthesis of Compound VI-5.

The title compound was prepared using the appropriate starting materials and following the methodologies described above. Analytical data: $R_t$ 7.98 min, 8.16 min, and 10.42 min (diastereomers); $^1$H-NMR (DMSO-d$_6$): δ 7.58–7.35 (a series of m, 8H), 6.03 and 6.02 (two overlapping s, 0.46H), 5.36 (s, 0.54H), 4.70 (m, 0.54H), 4.14–2.50 (series of m, 6H), 1.22–1.12 (overlapping d, 3H). MS: 372(M+H), 394 (M+Na).

Example 92h

Synthesis of Compound VI-6

The title compound was prepared using the appropriate starting materials and following the methodologies described above. Analytical data: $R_t$ 7.78 min and 7.88 min (diastereomers); $^1$H-NMR (DMSO-d$_6$): δ 7.63–7.22 (two m, 8H), 6.06 (s, 0.66H), 5.47 (s, 0.34l1), 3.82 (m, 0.34H), 3.69(m, 0.66H), 3.14(dd, 0.66H), 2.95(m, 1H), 2.84 and 2.81 (two s, 3H), 2.9 (dd, 0.34H). MS: 386 (M+Na).

Example 92i

Synthesis of Compound VI-7

The title compound was prepared using the appropriate starting materials and following the methodologies described above. Analytical data: $R_t$ 8.48 min and 8.70 min (diastereomers); $^1$H-NMR (DMSO-d$_6$): δ 11.52 (br, 1H), 7.69–7.60 (m, 4H), 7.29 (m, 2H), 6.32 (s, 0.11H), 5.60 (s, 0.9H), 3.75 (m, 1H), 3.81 (dd, 1H), 2.66–2.32 (m, 1H). MS: 348 (M+Na).

Example 92j

Synthesis of Compound VI-8

The title compound was prepared using the appropriate starting materials and following the methodologies described above. Analytical data: $R_t$ 8.70 min (overlapping diastereomers). $^1$H-NMR (DMSO-d$_6$): δ 11.62 and 11.53 (two br, 1H), 7.74–7.25 (m, 8H), 6.18 and 6.13 (two s, 0.4H), 5.47 and 5.45 (two singlets, 0.6H), 3.78–2.49 (a series of m, 3H). MS: 342 (M+Na).

Example 92k

Synthesis of Compound VIII-3

The title compound was prepared using the appropriate starting materials and following the methodologies described above. Analytical data: $R_t$ 10.79 min. and 10.98 min (diastereomers). $^1$H-NMR (DMSO-d$_6$): δ 8.04–7.37 (a series of m, 8H), 5.97 (s, 0.5H), 5.75 (s, 0.5H), 4.65 (m, 0.5H), 3.69–2.55 (a series of m, 2.08l), 1.65 (dd, 0.5H). MS: 392 (M+Na).

Example 92l

Synthesis of Compound VIII-4

The title compound was prepared using the appropriate starting materials and following the methodologies described above. Analytical data: $R_t$ 9.18 min and 9.30 min (diastereomers); $^1$H-NMR (DMSO-d$_6$): δ 8.05–7.37 (a series of m, 8H), 5.96 (s, 0.09H), 5.77 (s, 0.91H), 4.80 and 4.48 (two m, 1H), 3.57–2.49 (a series of m, 5.09H), 1.51 (dd, 0.91H). MS: 378 (M+H), 403 (M+Na).

Example 92m

Synthesis of Compound VIII-5

The title compound was prepared using the appropriate starting materials and following the methodologies described above. Analytical data: $R_t$ 10.03 min, 10.30 min, 10.42 min and 11.11 min (diastereomers). $^1$H-NMR (DMSO-d$_6$): δ 8.05–7.37 (a series of m, 8H), 5.95 and 5.94 (two overlapping singlets, 0.36H), 5.76 (s, 0.64H), 4.85–2.49 (a series of m, 6H), 1.29 and 1.08 (two sets of overlapping d, 3H). MS: 370 (M+H), 392 (M+Na).

Example 92n

Synthesis of Compound VIII-6

The title compound was prepared using the appropriate starting materials and following the methodologies described above. Analytical data: $R_t$ 7.22 min (overlapping diastereomers); $^1$H-NMR (DMSO-d$_6$): δ 11.23 and 10.89 (two singlets, 1H), 8.04–7.38 (a series of m, 8H), 6.00 (s, 0.37H), 5.77 (s, 0.63H), 4.65 (m, 0.37H), 3.32 (m, 0.63H), 3.22 (dd, 0.37H), 2.86 (dd, 0.37H), 2.59 (dd, 0.63H), 1.76 (dd, 0.6311). MS: 328 (M+H), 350 (M+Na).

Example 92o

Synthesis of Compound VIII-7

The title compound was prepared using the appropriate starting materials and following the methodologies described above. Analytical data: $R_t$ 13.90 min and 14.12 min (diastereomers); $^1$H-NMR (DMSO-d$_6$): δ 8.04–6.80 (a series of m, 12H), 5.98 (s, 0.111H), 5.76 (s, 0.89H), 4.65 (d, 0.22H), 4.37 (s, 1.78H), 3.69 (s, 3H), 3.31 (m, 1H), 2.93 (m, 0.111H), 2.63 (dd, 0.89H), 1.78 (dd, 1H). MS: 554 (M+Na).

Example 92p

Synthesis of Compound VIII-8

The title compound was prepared using the appropriate starting materials and following the methodologies described above. Analytical data: $R_t$ 9.48 min and 9.62 min (diastereomers); $^1$H-NMR (DMSO-d$_6$): δ 8.04–7.09 (a series of m, 13H), 5.97 (s, 0.1H), 5.84 (s, 0.9H), 4.70 (m, 0.11H), 3.38–3.24 (m, 1H), 3.04 (m, 0.11H), 2.72 (dd, 0.9H), 1.63 (dd, 0.9H). MS: 388 (M+H), 410 (M+Na).

Example 92q

Synthesis of Compound VII-1

The title compound was prepared from compound A1(Scheme 7) following the similar procedure as described for the synthesis of compound VIII-1 with the exception of utilizing 3-bromo-1-phenyl-pyrrolidin-2-one in place of maleimide in the first step. Analytical data: $R_t$ 9.36 min and 9.72 min (mixture of diastereomers); $^1$H-NMR (DMSO-d$_6$): δ 8.03–7.12 (a series of m, 13H), 6.19 (s, 0.11H), 5.66 (s, 0.9H), 3.71–3.28 (three m, 3H), 2.32 (m, 1H), 1.30 (m, 1H). MS: 374 (M+H), 396 (M+Na).

The following Examples 92r–92s were synthesized according to Scheme 8.

Scheme 8

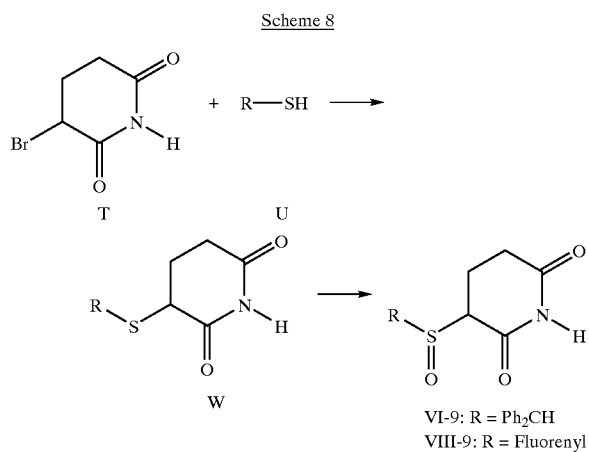

VI-9: R = Ph$_2$CH
VIII-9: R = Fluorenyl

In Scheme 8, the reaction of an appropriate thiol (compound U) with 3-bromo-glutarimide (T), in presence of a base, generated corresponding compound W. Oxidation of appropriate compound W produced compounds VI-9 and VIII-9, respectively. 3-Bromoglutarimide was prepared from procedures described in Japanese Patent Application No. 8308, 1961 and Japanese Patent Application No. 5277, 1960, both of which are incorporated by reference herein in their entirety.

Example 92r

Synthesis of Compound VI-9

To a cooled (0° C.) solution of diphenylmethylthiol (1 equiv.) and 3-bromo-glutarimide (1 equiv.) in dry tetrahydrofuran, DBU (1,8-Diazabicyclo[5.4.0]undec-7-ene)(1.05 equiv.) was added dropwise. The cooling bath was removed and the mixture was stirred at room temperature for 1–2 h, diluted with hexane:ethyl acetate (1:1) and washed successively with water and brine. Drying (magnesium sulfate) and solvent evaporation gave a crude product that was triturated with ethyl acetate to generate intermediate compound W (where R=Ph$_2$CH); $^1$H-NMR (DMSO-d$_6$): δ 10.81(s, 1H), 7.53–7.22 (a series of m, 10H), 5.52 (s, 1H), 3.3–1.81 (a series of m, 5H).

Oxidation of above-prepared compound W with hydrogen peroxide, following previously disclosed methodology, generated the title compound as a mixture of diastereomers; $R_t$ 9.20 min and 9.44 min; $^1$H-NMR (DMSO-d$_6$): δ 11.17 & 11.12 (two singlets, 1H), 7.57–7.33 (a series of m, 10H), 5.75 (s, 0.35H), 5.43 (s, 0.65H), 3.45–2.53 (a series of m, 5H). MS: 350 (M+Na).

Example 92s

Synthesis of Compound VIII-9

Following the same procedures as described above for the synthesis of VI-9, the title compound, starting from 9-fluorenylthiol, was also prepared as a diastereomeric mixture; $R_t$ 7.18 min and 7.47 min; $^1$H-NMR (DMSO-d,): 11.32 and 11.16 (two singlets, 1H), 7.99–7.35 (a series of m, 8H), 5.79 and 5.66 (two singlets, 1H), 4.26 and 4.07 (two multiplets, 1H), 2.70–2.10 (a series of m, 4H). MS: 326 (M+H), 348 (M+Na).

Example 93

Demonstration of Wake-Promoting Activity of Compound I-9

The methodology utilized is as described by Edgar and Seidel, Journal of Pharmacology and Experimental Therapeutics, 283:757–769, 1997, incorporated herein in its entirety by reference.

Animal Surgery.

Adult, male Wistar rats (275–320 g from Charles River Laboratories, Wilmington, Mass.) were anesthetized (Nembutal, 60 mg/kg, ip) and surgically prepared with implants for recording of chronic EEG and EMG recording. The EEG implants consisted of stainless steel screws (2 frontal (+3.9 AP from bregma, ±2.0 ML) and 3 occipital (−6.4 AP, ±5.5 ML). Two Teflon-coated stainless steel wires were positioned under the nuchal trapezoid muscles for EMG recording. All leads were soldered to a miniature connector (Microtech, Boothwyn, Pa.) and gas sterilized with ethylene oxide before surgery. The implant assembly was affixed to the skull by the combined adhesion of the EEG recording screws, cyanoacrylate applied between the hermetically sealed implant connector and skull and dental acrylic. An antibiotic (Gentamycin) was administered for 3 to 5 days postsurgery. At least 3 weeks were allowed for postsurgical recovery.

Recording Environment.

Rats were housed individually within specially modified Nalgene microisolator cages equipped with a low-torque slip-ring commutator (Biella Engineering, Irvine, Calif.) and a custom polycarbonate filter-top riser. These cages were isolated in separate, ventilated compartments of a stainless steel sleep-wake recording chamber. Food and water were available ad libitum and ambient temperature was 24±1° C. A 24-h light-dark cycle (light/dark 12-12-) was maintained throughout the study by 4-watt fluorescent bulbs located approximately 5 cm from the top of each cage. Light intensity was 30 to 35 lux at midlevel inside the cage. Animals were undisturbed for 3 days both before and after the treatments.

Automated Data Collection.

Sleep and wake stages were determined with SCORE, a microcomputer-based sleep-wake and physiological monitoring system. SCORE™design features, validation in rodents and utility in preclinical drug evaluation have been reported elsewhere (Van Gelder, et al., 1991; Edgar, et al., 1991, 1997; Seidel, et al, 1995, incorporated by reference herein in their entirety). In the present study, the system monitored amplified (X 10,000) EEG (bandpass, 1–30 Hz; digitization rate, 100 Hz) and integrated EMG (bandpass, 10–100 Hz, root mean square integration). Arousal states were classified on-line as NREM sleep, REM sleep, wake or theta-dominated wake every 10s by use of EEG period and amplitude feature extraction and ranked membership, algorithms. Individually taught EEG-arousal-state templates and EMG criteria differentiated REM sleep from theta-dominated wakefulness (Welsh, et al., 1985, incorporated by reference herein in its entirety). Data quality was assured by frequent on-line inspection of the EEG and EMG signals. Raw data quality and sleep-wake scoring was scrutinized further by a combination of graphical and statistical assessments of the data as well as visual examination of the raw EEG wave forms and distribution of integrated EMG values.

Drug Administration and Study Design.

Compound I-9 was suspended in sterile 0.25% methylcellulose (pH=6.2; Upjohn Co., Kalamazoo, Mich.) or methylcellulose vehicle alone was injected intraperitoneally in a volume of 1 ml/kg. Sample size (n) was 13 animals per treatment group.

EEG Spectral Analysis.

Each 10-s epoch of raw EEG signal was digitized (100 Hz) for 24 h and wakefulness was scored as described previously by Edgar and Seidel (1996), incorporated by reference herein in its entirety.

Data Analysis and Statistics.

The principal variable recorded was minutes per hour of wake. Treatment groups were compared post-treatment by repeated-measures ANOVA. In the presence of a significant main effect, Dunnett's contracts (a=0.05) assessed differences between active treatment groups and vehicle controls, unless otherwise specified.

Results.

FIG. 1 illustrates degree of wakefulness in rats treated at time zero with either 100 mg/kg, ip of compound I-9 (solid line) or methylcellulose vehicle (stippled line). Compound I-9 produced wakefulness beyond that observed in vehicle-treated animals that lasted until approximately 110 minutes following administration.

Example 94

Demonstration of Wake-Promoting Activity of Compound II-23

The methodology utilized is based on that described by Edgar and Seidel, Journal of Pharmacology and Experimental Therapeutics, 283:757–769, 1997, and incorporated herein in its entirety by reference.

Animal Surgery.

Adult, male Wistar rats (275–320 g from Charles River Laboratories, Wilmington, Mass.) were anesthetized (Nembutal, 45 mg/kg, ip) and surgically prepared with implants for recording of chronic EEG and EMG recording. The EEG implants were made from commercially available components (Plastics One, Roanoke, Va.). EEG's were recorded from stainless steel screw electrodes (2 frontal (+3.0 mm AP from bregma, ±2.0 mm ML) and 2 occipital (−4.0 mm AP, ±2.0 mm ML)). Two Teflon-coated stainless steel wires were positioned under the nuchal trapezoid muscles for EMG recording. All electrode leads were inserted into a connector pedestal and the pedestal, screws, and wires affixed to the skull by application dental acrylic. Antibiotic was administered post surgically and antibiotic cream was applied to the wound edges to prevent infection. At least 1 week elapsed between surgery and recording. Animals are tested for approximately 6–8 weeks and then sacrificed.

Recording Environment.

Postsurgically, rats were housed individually in an isolated room. At least 24 hrs. prior to recording, they were placed in Nalgene containers (31×31×31 cm) with a wire-mesh top, and entry to the room was prohibited until after recording had ended except for dosing. The containers were placed on a 2-shelf rack, 4 per shelf. Food and water were available ad libitum, ambient temperature was 21° C., and humidity was 55%. White-noise was provided in the background (68 db inside the containers) to mask ambient sounds. Fluorescent overhead room lights were set to a 24 hr. light/dark cycle (on at 7 AM, off at 7 PM). Light levels inside the containers were 38 and 25 lux for the top and bottom shelves respectively.

Data Acquisition.

EEG and EMG signals were led via cables to a commutator (Plastics One) and then to pre-amplifiers (model 1700, A-M Systems, Carlsborg, Wash.). EEG and EMG signals were amplified (10K and 1K respectively) and bandpass filtered between 0.3 and 500 Hz for EEG, and between 10 and 500 Hz for EMG. These signals were digitized at 128 samples per second using ICELUS sleep research software (M. Opp, U. Texas; see Opp, Physiology and Behavior 63:67–74, 1998, and Imeri, Mancia, and Opp, Neuroscience 92:745–749, 1999, incorporated by reference herein in their entirety) running under Labview 5.1 software and data acquisition hardware (PCI-MIO-16E-4; National Instruments, Austin, Tex.). On the day of dosing, data was recorded from 11 AM to 6 PM.

Sleep/Wake Scoring.

Sleep and wake stages were determined manually using ICELUS software. This program displays the EEG and EMG data in blocks of 6 sec. along with the EEG-FFT. Arousal state was scored as awake (WAK), rapid eye-movement (REM), or slow-wave or non-REM sleep (NREM) according to visual analysis of EEG frequency and amplitude characteristics and EMG activity (Opp and Krueger, American Journal of Physiology 266:$R_{688}$-95, 1994; Van Gelder, et al., 1991; Edgar, et al., 1991, 1997; Seidel, et al, 1995, incorporated by reference herein in their entirety). Essentially, waking activity consists of relative low-amplitude EEG activity with relatively lower power in the lower frequency bands from 0.5–6 Hz, accompanied by moderate to high level EMG activity. In a particular waking state ("theta-waking"), EEG power can be relatively focused in the 6–9 Hz (theta) range, but significant EMG activity is always present. NREM sleep is characterized by relative high-amplitude EEG activity with relatively greater power in the low frequency bands from 0.5–6 Hz, accompanied by little or no EMG activity. REM sleep is characterized by moderate and constant amplitude EEG focused in the theta (6–9 Hz range), similar to waking theta, but with no EMG activity.

Drug Administration and Study Design.

Compounds were evaluated on groups of 4 or 8 rats which were tested in 2 sessions at least 2 days apart. Initial studies used a crossover design, such that rats received either vehicle or test compound during each session. Animals were pseudo-randomized so that they did not receive the same drug twice. Compound II-23 was suspended in sterile 0.25% methylcellulose (pH=6.2; Upjohn Co., Kalamazoo, Mich.) at 30 mg/ml. This study was carried out on 8 rats which were tested in 2 sessions 5 days apart (overall, 7 rats received compound II-23 and 6 methylcellulose vehicle). Dosing was carried out at noon, while the rats were predominantly asleep. Each rat was lifted out of its container, given an intraperitoneal. injection in a volume of 3.33 ml/kg, and replaced. Dosing required approximately 8 minutes.

Data Analysis and Statistics.

The principal outcome measure was minutes per hour of wakefulness. The primary outcome measure for purposes of determining activity in these experiments consists of the total integrated wake time for the first 3 hours post dosing relative to vehicle control. Thus, vehicle treated animals typically average 20% wake time during the recording period, or a total of 0.2*180=36 min. A 2-tailed, unpaired t-test (Statview 5.0, SAS Institute, Inc., Cary, N.C.) was performed on the wake time values for drug and vehicle treated animals, and compounds with p<0.05 were deemed significantly wake-promoting. Waking activity was also evaluated for successive half-hour periods beginning with the time of dosing, and individual t-tests performed at each time point to establish the duration of significant wake-promoting activity.

Results.

Figure 2:
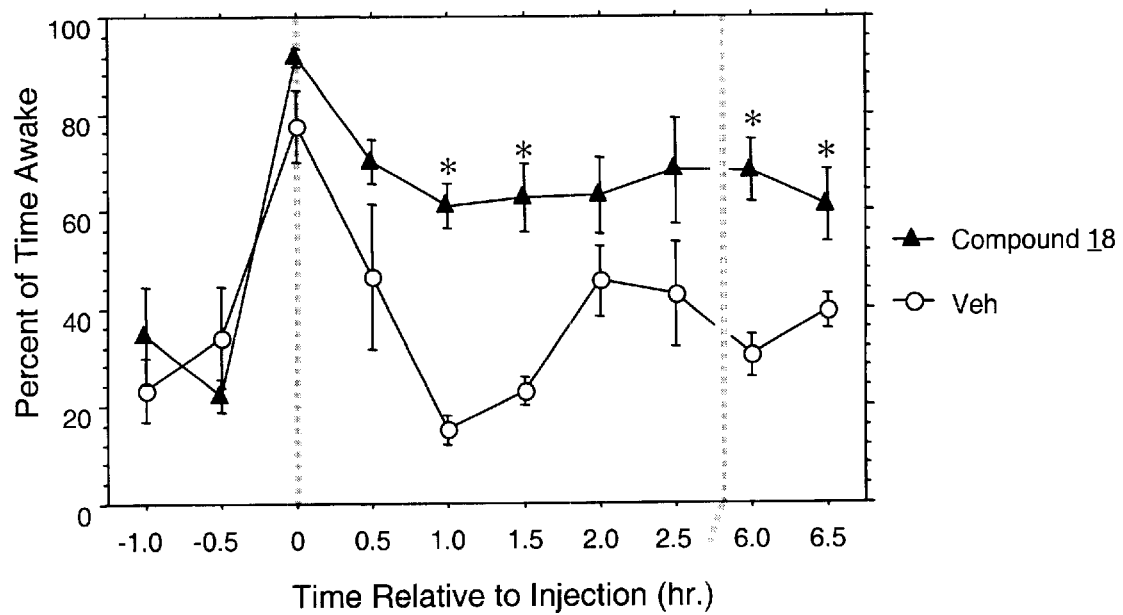
FIG. 2 is a graph of data indicating EEG-determined wakefulness in rats treated with compound II-23 (100 mg/kg, ip; solid triangles) or methylcellulose vehicle (open circles). Each point represents the mean percent of time awake for the succeeding half hour. *$p<0.05$ vs. vehicle treated animals.

FIG. 2 illustrates degree of wakefulness in rats treated at noon with either 100 mg/kg, ip. of compound II-23 (solid triangles) or methylcellulose vehicle (open circles). Each point represents the mean percent of time awake for the succeeding half hour. The dosing procedure produced a transient (~20 min.) period of elevated wakefulness in both treatment groups compared to pre-dosing baseline activity. Compound II-23 produced significantly greater wakefulness than that observed in vehicle-treated animals (p<0.05).

REFERENCES

The following references, to the extent that they provide exemplary procedural or other details supplementary to those set forth herein, are specifically incorporated in their entirety herein by reference:

Touret, et al., *Neuroscience Letters*, 189:43–46, 1995.
Van Gelder, R. N. et al., *Sleep* 14:48–55, 1991.
Edgar, D. M., *J. Pharmacol. Exp.Ther.* 282:420–429, 1997.
Edgar and Seidel, *J. Pharmacol. Exp. Ther.*, 283:757–69, 1997.
Hernant et al., *Psychopharmacology*, 103:28–32, 1991.
Lin et al., *Brain Research*, 591:319–326, 1992.
Opp and Krueger, *American Journal of Physiology* 266:$R_{688}$-95, 1994
Panckeri et al., *Sleep*, 19(8):626–631, 1996.
Seidel, W. F., et al., *J. Pharmacol. Exp. Ther.* 275:263–273, 1995.
Shelton et al., *Sleep* 18(10):817–826, 1995.
Welsh, D. K., et al., *Physiol. Behav.* 35:533–538, 1985.

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

What is claimed is:

1. A compound of the formula (II-A):

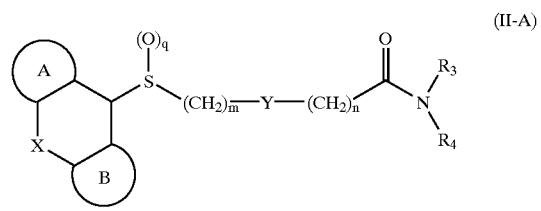

wherein

X is a bond, —$CH_2CH_2$—, —O—, —$S(O)_y$—, —$N(R_8)$—, —$CHN(R_8)$—, —CH=CH—, —$CH_2$—CH=CH—, C(=O), —$C(R_8)$=N—, —N=$C(R_8)$—, —C(=O)—$N(R_8)$—, or —$NR_8$—C(=O)—;

Rings A and B, together with the carbon atoms to which they are attached, are each independently selected from:
(a) a 6-membered aromatic carbocyclic ring in which from 1 to 3 carbon atoms may be replaced by hetero atoms selected from oxygen, nitrogen and sulfur; and
b) a 5-membered aromatic carbocyclic ring in which either:
i) one carbon atom is replaced with an oxygen, nitrogen, or sulfur atom;
ii) two carbon atoms are replaced with a sulfur and a nitrogen atom, an oxygen and a nitrogen atom, or two nitrogen atoms; or
iii) three carbon atoms are replaced with three nitrogen atoms, one oxygen and two nitrogen atoms, or one sulfur and two nitrogen atoms;

wherein Ring A and Ring B may each be independently substituted with 1–3 substituents selected from:
a) H, $C_6$–$C_{10}$ aryl, heteroaryl, F, Cl, Br, I, —CN, —$CF_3$, —$NO_2$, —OH, —$OR_7$, —$O(CH_2)_pNR_9R_{10}$, —OC(=O)$R_7$, —OC(=O)$NR_9R_{10}$, —$O(CH_2)_p$ $OR_8$, —$CH_2OR_8$, —$NR_9R_{10}$, —$NR_8S(=O)_2R_7$, —$NR_8C(=O)R_7$, or —$NR_8C(=S)R_7$;
b) —$CH_2OR_{11}$;
c) —$NR_8C(=O)NR_9R_{10}$, —$NR_8C(=S)NR_9R_{10}$, —$CO_2R_{12}$, —C(=O)$R_{13}$, —C(=O)$NR_9R_{10}$, —C(=S)$NR_9R_{10}$, —CH=$NOR_{12}$, —CH=$NR_7$, —$(CH_2)_pNR_9R_{10}$, —$(CH_2)_pNHR_{11}$, —CH=$NNR_{12}R_{12}A$, —C(=$NR_8$)$NR_{8A}R_{8B}$—$NR_8C(=NH)R_{8A}$, —$NR_8C(=NH)NR_{8A}R_{8B}$,

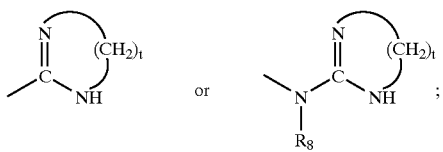

d) —S(O)$_y$R$_7$, —(CH$_2$)$_p$S(O)$_y$R$_7$, —CH$_2$S(O)$_y$R$_7$; and
e) C$_1$–C$_8$ alkyl, C$_2$–C$_8$ alkenyl, or C$_2$–C$_8$ alkynyl, where:
  1) each alkyl, alkenyl, or alkynyl group is unsubstituted; or
  2) each alkyl, alkenyl or alkynyl group is independently substituted with 1 to 3 groups independently selected from C$_6$–C$_{10}$ aryl, heteroaryl, F, Cl, Br, I, CF$_3$, —CN, —NO$_2$, —OH, —OR$_7$, —CH$_2$OR$_8$, —NR$_9$R$_{10}$, —O—(CH$_2$)$_p$—OH, —S—(CH$_2$)$_p$—OH, —X$_1$(CH$_2$)$_p$OR$_7$, X$_1$(CH$_2$)$_p$NR$_9$R$_{10}$, —X$_1$(CH$_2$)$_p$C(=O)NR$_9$R$_{10}$, —X$_1$(CH$_2$)$_p$C(=S)NR$_9$R$_{10}$, —X$_1$(CH$_2$)$_p$OC(=O)NR$_9$R$_{10}$, —X$_1$(CH$_2$)$_p$CO$_2$R$_8$, —X$_1$(CH$_2$)$_p$S(O)$_y$R$_7$, —X$_1$(CH$_2$)$_p$NR$_8$C(=O)NR$_9$R$_{10}$, —C(=O)R$_{13}$, —CO$_2$R$_{12}$, —OC(=O)R$_7$, —C(=O)NR$_9$R$_{10}$, —OC(=O)NR$_{12}$R$_{12A}$, O-tetrahydropyranyl, —C(=S)NR$_9$R$_{10}$, —CH=NNR$_{12}$R$_{12A}$, —CH=NOR$_{12}$, —CH=N$_7$, —CH=NNHCH(N=NH)NH$_2$, —NR$_8$CO$_2$R$_7$, —NR$_8$C(=O)NR$_9$R$_{10}$, —NR$_8$C(=S)NR$_9$R$_{10}$, —NHC(=NH)NH$_2$, —NR$_8$C(=O)R$_7$, —NR$_8$C(=S)R$_7$, —NR$_8$S(=O)$_2$R$_7$, —S(O)$_y$R$_7$, —S(=O)$_2$NR$_{12}$R$_{12A}$, —P(=O)(OR$_8$)$_2$, —OR$_{11}$, and a C$_5$–C$_7$ monosaccharide where each hydroxyl group of the monosaccharide is independently either unsubstituted or is replaced by H, C$_1$–C$_4$ alkyl, C$_1$–C$_4$ alkoxy, or —O—C(=O)R$_7$;

R$_3$ and R$_4$ are the same or different and are each selected from H, C$_1$–C$_6$ alkyl, —OH, —CH(R$_6$)—CONR$_{8A}$R$_{8B}$, provided that R$_3$ and R$_4$ are not both OH, or R$_3$ and R$_4$, together with the nitrogen to which they are attached, form a 3–7 member heterocyclic ring;

R$_6$ is H, C$_1$–C$_4$ alkyl or the side chain of an α-amino acid;

R$_7$ is C$_1$–C$_6$ alkyl, C$_6$–C$_{10}$ aryl, or heteroaryl;

R$_8$, R$_{8A}$ and R$_{8B}$ are each independently H, C$_1$–C$_4$ alkyl, or C$_6$–C$_{10}$ aryl;

R$_9$ and R$_{10}$ are independently selected from H, C$_1$–C$_4$ alkyl, and C$_6$–C$_{10}$ aryl; or R$_9$ and R$_{10}$ together with the nitrogen to which they are attached, form a 3–7 member heterocyclic ring;

R$_{11}$ is the residue of an amino acid after the hydroxyl group of the carboxyl group is removed;

R$_{12}$ and R$_{12A}$ are each independently selected from H, C$_1$–C$_6$ alkyl, cycloalkyl, C$_6$–C$_{10}$ aryl, and heteroaryl; or R$_{12}$ and R$_{12A}$, together with the nitrogen to which they are attached, form a 5–7 member heterocyclic ring;

R$_{13}$ is H, C$_1$–C$_6$ alkyl, cycloalkyl, C$_6$–C$_{10}$ aryl, heteroaryl, —C(=O)R$_7$, —C(=O)NR$_9$R$_{10}$, or —C(=S)NR$_9$R$_{10}$;

X$_1$ is —O—, —S—, —N(R$_8$)—;

Y is selected from C$_1$–C$_4$ alkylene, C$_6$–C$_{10}$ arylene, heteroarylene, C$_3$–C$_8$ cycloalkylene, heterocyclylene, —O—, —N(R$_8$)—, —S(O)$_y$, —CR$_{8A}$=CR$_{8B}$—, —CH=CH—CH(R$_8$)—, —CH(R$_8$)—CH=CH—, or —C≡C—; with the proviso that when Y is —O—, —N(R$_8$)—, or —S(O)$_y$, m and n cannot be 0;

m is 0, 1, 2 or 3;
n is 0, 1, 2 or 3;
p is from 1 to 4;
q is 0, 1, 2;
t is 2, 3, or 4;
y is 0, 1 or 2;

provided that when rings A and B are phenyl, X is —CH$_2$CH$_2$—, q is 0, m and n are 0, and Y is C$_1$–C$_4$ alkylene, then R$_3$ and R$_4$ are the same or different and are each selected from H, —OH, —CH(R$_6$)—CONR$_{8A}$R$_{8B}$, provided that R$_3$ and R$_4$ are not both OH, or R$_3$ and R$_4$, together with the nitrogen to which they are attached, form a 3–7 member heterocyclic ring;

and the stereoisomeric forms, mixtures of stereoisomeric forms, or pharmaceutically acceptable salt and ester forms thereof.

2. The compound of claim 1, wherein q=1.

3. The compound of claim 1, wherein rings A and B, together with the carbon atoms to which they are attached, are each independently selected from phenylene, thienylene, isothiazolylene, pyridylene, oxazolylene, isoxazolylene, thiazolylene, imidazolylene.

4. The compound of claim 3, wherein ring A is phenylene.

5. The compound of claim 4, wherein ring B is phenylene.

6. The compound of claim 1, wherein X is a bond, —CH$_2$CH$_2$—, —O—, —N(CH$_3$)—, or —CH=CH—.

7. The compound of claim 1, wherein Y is phenylene.

8. The compound of claim 1, wherein Y is C$_1$–C$_4$ alkylene.

9. The compound of claim 1, wherein rings A and B are phenylene; X is a bond; Y is C$_1$ alkylene; and m and n=0.

10. The compound of claim 1, wherein the compound is selected in accordance with the following table:

| No. | A | B | X | Y | m | n | NR$_3$R$_4$ |
|---|---|---|---|---|---|---|---|
| II-1 | Bnezo | Benzo | bond | —CH$_2$— | 1 | 0 | NH$_2$ |
| II-2 | Benzo | Benzo | bond | —CH$_2$— | 1 | 0 | NMe$_2$ |
| II-3 | Benzo | Benzo | bond | —CH$_2$— | 1 | 1 | NH$_2$ |
| II-4 | Benzo | Benzo | bond | —CH$_2$— | 1 | 0 | NHCH(CH$_3$)—CONH$_2$ |
| II-5 | Benzo | Benzo | bond | —CH$_2$— | 1 | 0 | morpholino |
| II-6 | Benzo | Benzo | bond | —CH$_2$— | 2 | 1 | NH$_2$ |
| II-7 | Benzo | Benzo | bond | —CH$_2$— | 2 | 1 | NMe$_2$ |
| II-8 | Benzo | Benzo | bond | —CH(CH$_3$)— | 1 | 0 | NH$_2$ |
| II-9 | Benzo | Benzo | bond | —CH$_2$— | 0 | 0 | NHCH(CH$_3$)—CONH$_2$ |

-continued

| No. | A | B | X | Y | m | n | NR₃R₄ |
|---|---|---|---|---|---|---|---|
| II-10 | Benzo | Benzo | bond | 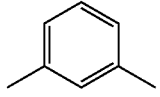 | 1 | 0 | NH₂ |
| II-11 | Benzo | Benzo | bond | —C(CH₃)₂— | 1 | 0 | NH₂ |
| II-12 | Benzo | Benzo | bond | 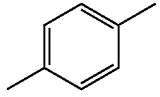 | 1 | 0 | NH₂ |
| II-13 | Benzo | Benzo | —CH₂CH₂— | —CH₂— | 1 | 0 | NH₂ |
| II-14 | Benzo | Benzo | —CH₂CH₂— | —CH(CH₃)— | 1 | 0 | NH₂ |
| II-15 | Benzo | Benzo | bond | 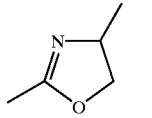 | 1 | 0 | NH₂ |
| II-16 | Benzo | Benzo | bond | 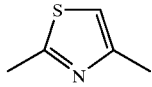 | 1 | 0 | NH₂ |
| II-17 | Benzo | Benzo | bond | 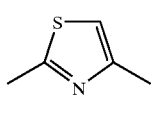 | 1 | 0 | NMe₂ |
| II-18 | Benzo | Benzo | —CH=CH— | —CH₂— | 2 | 1 | NH₂ |
| II-19 | Benzo | Benzo | —CH=CH— | —C(CH₃)₂— | 1 | 0 | NH₂ |
| II-20 | Benzo | Benzo | —O— | —CH₂— | 2 | 1 | NH₂ |
| II-21 | Benzo | Benzo | —O— | —CH(CH₃)— | 1 | 0 | NH₂ |
| II-22 | 2,3-Thieno | 2,3-Thieno | bond | —CH₂— | 0 | 0 | NH₂ |
| II-23 | Benzo | Benzo | bond | —CH₂— | 0 | 0 | NH₂ |
| II-24 | Benzo | Benzo | bond | —CH₂— | 0 | 0 | NHCH(CH₃)—CONMe₂ |
| II-25 | Benzo | Benzo | —CH₂CH₂— | —CH₂— | 0 | 0 | NH₂ |
| II-26 | Benzo | Benzo | —CH₂CH₂— | —CH₂— | 0 | 0 | N(CH₃)₂ |
| II-27 | Benzo | Benzo | —O— | —CH₂— | 0 | 0 | NH₂ |
| II-28 | Benzo | Benzo | —N(CH₃)— | —CH₂— | 0 | 0 | NH₂ |
| II-29 | Benzo | Benzo | —S— | —CH₂— | 0 | 0 | NH₂ |
| II-30 | Benzo | Benzo | bond | —CH₂— | 0 | 0 | NH(CH₃) |
| II-31 | Benzo | Benzo | bond | —CH₂— | 0 | 0 | NH(CH₂CH₂—NH[t-Boc]) |
| II-32 | Benzo | Benzo | bond | —CH₂— | 0 | 0 | NH(CH₂-[2-pyridyl]) |
| II-33 | Benzo | Benzo | bond | —CH₂— | 0 | 0 | NH(CH₂-[3-pyridyl]) |
| II-34 | Benzo | Benzo | bond | —CH₂— | 0 | 0 | NH(CH₂CH₂OH) |
| II-35 | Benzo | Benzo | bond | —CH₂— | 0 | 0 | N(CH₃)₂ |
| II-36 | Benzo | Benzo | bond | —CH₂— | 0 | 0 |  |
| II-37 | Benzo | Benzo | —CH=CH— | —CH₂— | 0 | 0 | NH₂ |
| II-38 | Benzo | Benzo | bond | 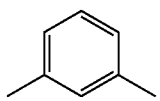 | 1 | 0 | N(CH₃)₂ |
| II-39 | Benzo | Benzo | bond | —CH₂— | 0 | 0 | NHOH |
| II-40 | Benzo | Benzo | bond | —CH₂— | 0 | 0 | NHCH₂CONH₂ |
| II-41 | Benzo | Benzo | bond | —CH₂— | 0 | 0 | NH(CH₂)₂—CONH₂ |
| II-42 | Benzo | Benzo | bond | —CH₂— | 0 | 0 | NH(CH₂)₂F |
| II-43 | Benzo | Benzo | bond | —CH₂— | 0 | 0 | NEt₂ |
| II-44 | Benzo | Benzo | bond | —CH₂— | 0 | 0 | NH—(R)—CH(CH₃)CONH₂ |
| II-45 | Benzo | Benzo | bond | —CH₂— | 0 | 0 | NH—(R)—CH(CH₃)—C₆H₅ |
| II-46 | Benzo | Benzo | bond | —CH₂— | 0 | 0 | NH—(S)—CH(CH₃)—CH₂OH |
| II-47 | Benzo | Benzo | bond | —CH₂— | 0 | 0 | NH—(S)—CH(CH₃)—CO₂Me |
| II-48 | Benzo | Benzo | bond | —CH₂— | 0 | 0 | NH—(S)—CH(CH₃)CONH₂ |
| II-49 | Benzo | Benzo | bond | —CH₂— | 0 | 0 | NH—(S)—CH(CH₃)CONH₂ |

-continued

| No. | A | B | X | Y | m | n | NR₃R₄ |
|---|---|---|---|---|---|---|---|
| II-50 | Benzo | Benzo | bond | —CH₂— | 0 | 0 | NH—(S)—CH(CH₃)CONMe₂ |
| II-51 | Benzo | Benzo | bond | —CH₂— | 0 | 0 | NH—(S)—CH(CH₂OH)CONH₂ |
| II-52 | Benzo | Benzo | bond | —CH₂— | 0 | 0 | NH—(S)—CH[CH(OH)CH₃]CONH₂ |
| II-53 | Benzo | Benzo | bond | —CH₂— | 0 | 0 | (pyrrolidine-2-CONH₂) |
| II-54 | Benzo | Benzo | bond | —CH(CH₃)— | 0 | 0 | NH₂ |
| II-55 | Benzo | Benzo | —O— | —CH₂— | 1 | 0 | NH₂ |
| II-56 | Benzo | Benzo | —O— | —CH₂— | 0 | 0 | N(CH₃)₂ |
| II-57 | Benzo | Benzo | —O— | —CH₂— | 0 | 0 | NH—(S)—CH(CH₃)CONH₂ |
| II-58 | Benzo | Benzo | —CH₂CH₂— | —CH₂CH₂— | 0 | 0 | NH₂ |
| II-59 | Benzo | Benzo | —CH₂CH₂— | —CH(CH₃)— | 1 | 0 | NH₂ |
| II-60 | Benzo | Benzo | bond | (p-xylylene) | 0 | 0 | NH₂ |
| II-61 | Benzo | Benzo | —CH=CH— | —C(CH₃)₂— | 1 | 0 | NH₂ |
| II-62 | Benzo | Benzo | —CH₂CH₂— | —CH₂— | 1 | 0 | NH—CH(CH₃)CONH₂ |
| II-63 | Benzo | Benzo | —CH₂CH₂— | —CH₂— | 1 | 0 | morpholino |
| II-64 | Benzo | Benzo | bond | (2,5-furanyl) | 1 | 0 | NH₂ |
| II-65 | Benzo | Benzo | bond | —CH=CH— | 0 | 0 | NH₂ |
| II-66 | (pyrazole with 3-(3,4-dimethoxyphenyl) substituent) | Benzo | bond | —CH₂— | 0 | 0 | NH₂. |

11. A method of treating diseases or disorders in a subject in need thereof comprising administering a therapeutically effective amount of a compound of claim 1 to said subject.

12. The method of claim 11, wherein the compound is administered for the treatment of sleepiness, tiredness, Parkinson's disease, cerebral ischemia, stroke, sleep apneas, eating disorders, attention deficit hyperactivity disorder, cognitive dysfunction or fatigue; and for the promotion of wakefulness, stimulation of appetite, or stimulation of weight gain.

13. The method of claim 11, wherein the compound is administered for the treatment of disorders associated with hypofunctionality of the cerebral cortex.

14. The method of claim 13, wherein the compound is administered for the treatment of depression, schizophrenia, and chronic fatigue syndrome.

15. A pharmaceutical composition comprising a compound of claim 1 in admixture with one or more pharmaceutically acceptable excipients.

16. The compound of claim 1, wherein the compound is selected in accordance with the following table:

| No. | A | B | X | Y | m | n | NR₃R₄ |
|---|---|---|---|---|---|---|---|
| II-1 | Bnezo | Benzo | bond | —CH₂— | 1 | 0 | NH₂ |
| II-2 | Benzo | Benzo | bond | —CH₂— | 1 | 0 | NMe₂ |
| II-3 | Benzo | Benzo | bond | —CH₂— | 1 | 1 | NH₂ |
| II-4 | Benzo | Benzo | bond | —CH₂— | 1 | 0 | NHCH(CH₃)—CONH₂ |
| II-6 | Benzo | Benzo | bond | —CH₂— | 2 | 1 | NH₂ |
| II-7 | Benzo | Benzo | bond | —CH₂— | 2 | 1 | NMe₂ |
| II-8 | Benzo | Benzo | bond | —CH(CH₃)— | 1 | 0 | NH₂ |

-continued

| No. | A | B | X | Y | m | n | NR₃R₄ |
|---|---|---|---|---|---|---|---|
| II-10 | Benzo | Benzo | bond | 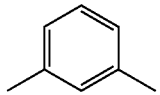 | 1 | 0 | NH$_2$ |
| II-11 | Benzo | Benzo | bond | —C(CH$_3$)$_2$— | 1 | 0 | NH$_2$ |
| II-12 | Benzo | Benzo | bond | 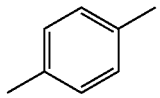 | 1 | 0 | NH$_2$ |
| II-13 | Benzo | Benzo | —CH$_2$CH$_2$— | —CH$_2$— | 1 | 0 | NH$_2$ |
| II-14 | Benzo | Benzo | —CH$_2$CH$_2$— | —CH(CH$_3$)— | 1 | 0 | NH$_2$ |
| II-15 | Benzo | Benzo | bond | 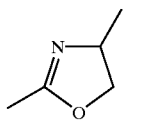 | 1 | 0 | NH$_2$ |
| II-24 | Benzo | Benzo | bond | —CH$_2$— | 0 | 0 | NHCH(CH$_3$)—CONMe$_2$ |
| II-27 | Benzo | Benzo | —O— | —CH$_2$— | 0 | 0 | NH$_2$ |
| II-30 | Benzo | Benzo | bond | —CH$_2$— | 0 | 0 | NH(CH$_3$) |
| II-31 | Benzo | Benzo | bond | —CH$_2$— | 0 | 0 | NH(CH$_2$CH$_2$—NH[t-Boc]) |
| II-32 | Benzo | Benzo | bond | —CH$_2$— | 0 | 0 | NH(CH$_2$-[2-pyridyl]) |
| II-33 | Benzo | Benzo | bond | —CH$_2$— | 0 | 0 | NH(CH$_2$-[3-pyridyl]) |
| II-34 | Benzo | Benzo | bond | —CH$_2$— | 0 | 0 | NH(CH$_2$CH$_2$OH) |
| II-35 | Benzo | Benzo | bond | —CH$_2$— | 0 | 0 | N(CH$_3$)$_2$ |
| II-36 | Benzo | Benzo | bond | —CH$_2$— | 0 | 0 |  |
| II-37 | Benzo | Benzo | —CH=CH— | —CH$_2$— | 0 | 0 | NH$_2$ |
| II-38 | Benzo | Benzo | bond | 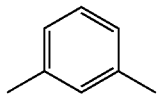 | 1 | 0 | N(CH$_3$)$_2$ |
| II-39 | Benzo | Benzo | bond | —CH$_2$— | 0 | 0 | NHOH |
| II-40 | Benzo | Benzo | bond | —CH$_2$— | 0 | 0 | NHCH$_2$CONH$_2$ |
| II-41 | Benzo | Benzo | bond | —CH$_2$— | 0 | 0 | NH(CH$_2$)$_2$—CONH$_2$ |
| II-42 | Benzo | Benzo | bond | —CH$_2$— | 0 | 0 | NH(CH$_2$)$_2$F |
| II-43 | Benzo | Benzo | bond | —CH$_2$— | 0 | 0 | NEt$_2$ |
| II-44 | Benzo | Benzo | bond | —CH$_2$— | 0 | 0 | NH—(R)—CH(CH$_3$)CONH$_2$ |
| II-45 | Benzo | Benzo | bond | —CH$_2$— | 0 | 0 | NH—(R)—CH(CH$_3$)—C$_6$H$_5$ |
| II-46 | Benzo | Benzo | bond | —CH$_2$— | 0 | 0 | NH—(S)—CH(CH$_3$)—CH$_2$OH |
| II-47 | Benzo | Benzo | bond | —CH$_2$— | 0 | 0 | NH—(S)—CH(CH$_3$)—CO$_2$Me |
| II-48 | Benzo | Benzo | bond | —CH$_2$— | 0 | 0 | NH—(S)—CH(CH$_3$)CONH$_2$ |
| II-49 | Benzo | Benzo | bond | —CH$_2$— | 0 | 0 | NH—(S)—CH(CH$_3$)CONH$_2$ |
| II-50 | Benzo | Benzo | bond | —CH$_2$— | 0 | 0 | NH—(S)—CH(CH$_3$)CONMe$_2$ |
| II-51 | Benzo | Benzo | bond | —CH$_2$— | 0 | 0 | NH—(S)—CH(CH$_2$OH)CONH$_2$ |
| II-52 | Benzo | Benzo | bond | —CH$_2$— | 0 | 0 | NH—(S)—CH[CH(OH)CH$_3$]CONH$_2$ |
| II-53 | Benzo | Benzo | bond | —CH$_2$— | 0 | 0 | 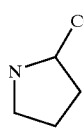 |
| II-54 | Benzo | Benzo | bond | —CH(CH$_3$)— | 0 | 0 | NH$_2$ |
| II-56 | Benzo | Benzo | —O— | —CH$_2$— | 0 | 0 | N(CH$_3$)$_2$ |
| II-57 | Benzo | Benzo | —O— | —CH$_2$— | 0 | 0 | NH—(S)—CH(CH$_3$)CONH$_2$ |
| II-58 | Benzo | Benzo | —CH$_2$CH$_2$— | —CH$_2$CH$_2$— | 0 | 0 | NH$_2$ |
| II-59 | Benzo | Benzo | —CH$_2$CH$_2$— | —CH(CH$_3$)— | 1 | 0 | NH$_2$ |

-continued

| No. | A | B | X | Y | m | n | NR$_3$R$_4$ |
|---|---|---|---|---|---|---|---|
| II-60 | Benzo | Benzo | bond | (p-tolyl) | 0 | 0 | NH$_2$ |
| II-61 | Benzo | Benzo | —CH=CH— | —C(CH$_3$)$_2$— | 1 | 0 | NH$_2$ |
| II-62 | Benzo | Benzo | —CH$_2$CH$_2$— | —CH$_2$— | 1 | 0 | NH—CH(CH$_3$)CONH$_2$ |
| II-63 | Benzo | Benzo | —CH$_2$CH$_2$— | —CH$_2$— | 1 | 0 | morpholino |
| II-64 | Benzo | Benzo | bond | (furan-2,5-diyl) | 1 | 0 | NH$_2$ |
| II-65 | Benzo | Benzo | bond | —CH=CH— | 0 | 0 | NH$_2$ |
| II-66 | 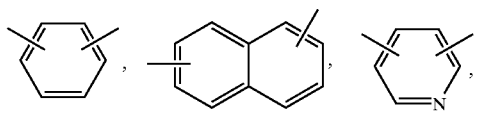 | Benzo | bond | —CH$_2$— | 0 | 0 | NH$_2$. |

17. The compound of claim 1, wherein when rings A and B are phenyl, X is —CH$_2$CH$_2$—, or —CH=CH—, q is 0, and —(CH$_2$)$_m$—Y—(CH$_2$)$_n$— is C$_1$-C$_4$ alkylene, then one of R$_3$ and R$_4$ are the same or different and are each selected from —OH, —CH(R$_6$)—CONR$_{8A}$R$_{8B}$.

18. The compound of claim 1 wherein ring A is unsubstituted phenyl, ring B is unsubstituted, X is a bond, —CH$_2$CH$_2$—, —O—, —S(O)$_n$—, —N(R$_8$)—, —CH=CH—, or —CH$_2$—CH=CH—, wherein R$_8$ is H or C$_1$-C$_4$ alkyl; m and n are 0; Y= —C(R$_1$)(R$_2$), wherein R$_1$ and R$_2$ are each independently selected from H or C$_1$-C$_4$ alkyl; and R$_3$ and R$_4$ are the same or different and are each selected from H, C$_1$-C$_4$ alkyl, —OH, —CH(R$_6$)—CONR$_{8A}$R$_{8B}$, wherein R$_{8A}$ and R$_{8B}$ are each independently H or C$_1$-C$_4$ alkyl, provided that R$_3$ and R$_4$ are not both OH; or R$_3$ and R$_4$, together with the nitrogen to which they are attached, form an unsubstituted 3–7 member heterocyclic ring.

19. The compound of claim 1, wherein Y is —O—, —S(O)$_y$—, or —N(R$_8$)—.

20. The compound of claim 1, wherein Y is —CR$_{8A}$=CR$_{8B}$—, —CH=CH—CH(R$_8$)—, —CH(R$_8$)—CH=CH—, or —(C≡C—.

21. The compound of claim 1, wherein Y is C$_6$-C$_{10}$ arylene or heteroarylene.

22. The compound of claim 1, wherein m=0 or 1 and n=0 or 1, and Y is

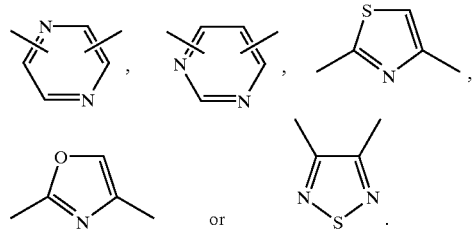

23. The compound of claim 1, wherein Y is C$_3$-C$_8$ cycloalkylene or heterocyclylene.

24. The compound of claim 23, wherein Y is

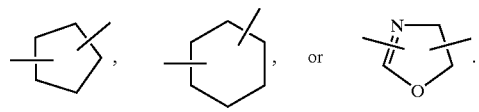

25. The compound of claim 1, wherein at least one of rings A and B are thienylene.

26. The compound of claim 25, wherein ring A is phenylene and ring B is 2,3-thienylene.

27. The compound of claim 6, wherein X is a bond.

28. The compound of claim 1, wherein rings A and B are phenyl, q is 1, m, n are 0, X is a bond, and Y is C$_1$-C$_4$ alkylene or phenylene.

29. The compound of claim 1, wherein rings A and B are phenyl, q is 1, m, n are 0, X is —CH$_2$CH$_2$—, —O—, —N(R$_8$)—, or —CH=CH—, and Y is C$_1$-C$_4$ alkylene or phenylene.

* * * * *

UNITED STATES PATENT AND TRADEMARK OFFICE
CERTIFICATE OF CORRECTION

| | |
|---|---|
| PATENT NO. | : 6,670,358 B2 |
| APPLICATION NO. | : 10/014645 |
| DATED | : December 30, 2004 |
| INVENTOR(S) | : Bacon et al. |

It is certified that error appears in the above-identified patent and that said Letters Patent is hereby corrected as shown below:

Front Page, Section (75) Inventors, remove Rabindranath Tripathy, Landenberg, PA (US).

Signed and Sealed this

Eleventh Day of July, 2006

JON W. DUDAS
*Director of the United States Patent and Trademark Office*

UNITED STATES PATENT AND TRADEMARK OFFICE
CERTIFICATE OF CORRECTION

PATENT NO.        : 6,670,358 B2  
APPLICATION NO. : 10/014645  
DATED             : December 30, 2003  
INVENTOR(S)       : Bacon et al.

It is certified that error appears in the above-identified patent and that said Letters Patent is hereby corrected as shown below:

Front Page, Section (75) Inventors, remove Rabindranath Tripathy, Landenberg, PA (US).

This certificate supersedes Certificate of Correction issued July 11, 2006.

Signed and Sealed this

Twenty-second Day of August, 2006

JON W. DUDAS  
*Director of the United States Patent and Trademark Office*

UNITED STATES PATENT AND TRADEMARK OFFICE
CERTIFICATE OF CORRECTION

PATENT NO.       : 6,670,358 B2
APPLICATION NO.  : 10/014645
DATED            : December 30, 2003
INVENTOR(S)      : Bacon et al.

It is certified that error appears in the above-identified patent and that said Letters Patent is hereby corrected as shown below:

Claim 1; column 78, lines 25 to 31
"provided that when rings A and B are phenyl, X is $-CH_2CH_2-$, q is 0, m and n are 0, and Y is $C_1$-$C_4$ alkylene, then $R_3$ or $R_4$ are the same or different and are each selected from H, $-OH$, $-CH(R_6)-CONR_{8A}R_{8B}$, provided that $R_3$ and $R_4$ are not both OH, or $R_3$ and $R_4$, together with the nitrogen to which they are attached, form a 3-7 member heterocyclic ring;"

should read:

--provided that when rings A and B are phenyl, X is $-CH_2CH_2-$, q is 0, and $-(CH_2)_m-Y-(CH_2)_n-$ is $C_1$-$C_4$ alkylene, then one of $R_3$ or $R_4$ cannot be H, methyl, ethyl, nor can $R_3$ and $R_4$, together with the nitrogen to which they are attached, form piperidyl, piperizinyl, or N-methylpiperizinyl; and also provided that when rings A and B are phenyl, X is $-CH=CH-$, q is 0, and $-(CH_2)_m-Y-(CH_2)_n-$ is $C_1$-$C_4$ alkylene, then one of $R_3$ or $R_4$ cannot be H or methyl;--

Signed and Sealed this

Fourth Day of September, 2007

JON W. DUDAS
*Director of the United States Patent and Trademark Office*